(12) United States Patent
Park et al.

(10) Patent No.: US 11,871,660 B2
(45) Date of Patent: Jan. 9, 2024

(54) COMPOUND AND ORGANIC LIGHT-EMITTING DEVICE INCLUDING THE SAME

(71) Applicant: Samsung Display Co., Ltd., Yongin-si (KR)

(72) Inventors: Hyejeong Park, Yongin-si (KR); Daehyeon Kim, Yongin-si (KR); Myeongsuk Kim, Yongin-si (KR); Jimyoung Ye, Yongin-si (KR); Juwon Lee, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 423 days.

(21) Appl. No.: 16/791,402

(22) Filed: Feb. 14, 2020

(65) Prior Publication Data

US 2021/0020845 A1 Jan. 21, 2021

(30) Foreign Application Priority Data

Jul. 15, 2019 (KR) .......................... 10-2019-0085206

(51) Int. Cl.
*H01L 51/00* (2006.01)
*H10K 85/60* (2023.01)
(Continued)

(52) U.S. Cl.
CPC ......... *H10K 85/654* (2023.02); *C07D 403/14* (2013.01); *C07D 471/04* (2013.01); *C07D 487/14* (2013.01); *C07D 519/00* (2013.01); *H10K 85/6572* (2023.02); *H10K 50/115* (2023.02); *H10K 50/15* (2023.02); *H10K 50/16* (2023.02); *H10K 50/17* (2023.02); *H10K 50/171* (2023.02); *H10K 50/18* (2023.02)

(58) Field of Classification Search
CPC ............. H01L 51/5012; H01L 51/5016; H01L 51/0054; H01L 51/0055; H01L 51/0056; H10K 85/654; H10K 50/11; C07D 401/10; C07D 403/10; C07D 405/10; C07D 409/10
See application file for complete search history.

(56) References Cited

U.S. PATENT DOCUMENTS 9,147,846 B2 * 9/2015 Kim ..................... C07D 213/16
9,255,084 B2 2/2016 Lee et al.
(Continued)

FOREIGN PATENT DOCUMENTS

EP 1 748 045 B1 5/2012
KR 10-2016-0013239 A 2/2016
(Continued)

*Primary Examiner* — Younes Boulghassoul
*Assistant Examiner* — Quinton A Brasfield
(74) *Attorney, Agent, or Firm* — Lewis Roca Rothgerber Christie LLP

(57) ABSTRACT

A compound is represented by Formula 1. An organic light-emitting device includes: a first electrode; a second electrode facing the first electrode; and an organic layer between the first electrode and the second electrode and including an emission layer, wherein the organic layer includes the compound represented by Formula 1. The compound represented by Formula 1 suppresses or reduces the generation of dark spots by chelating metal that migrates from an electrode.

20 Claims, 2 Drawing Sheets

(51) Int. Cl.
*C07D 471/04* (2006.01)
*C07D 519/00* (2006.01)
*C07D 403/14* (2006.01)
*C07D 487/14* (2006.01)
*H10K 50/15* (2023.01)
*H10K 50/16* (2023.01)
*H10K 50/17* (2023.01)
*H10K 50/18* (2023.01)
*H10K 50/115* (2023.01)

(56) References Cited

U.S. PATENT DOCUMENTS

| | | | |
|---|---|---|---|
| 9,673,259 B2 * | 6/2017 | Park | H01L 51/0094 |
| 2012/0138907 A1 | 6/2012 | Murase et al. | |
| 2012/0199817 A1 | 8/2012 | Nishimura et al. | |
| 2013/0032764 A1 * | 2/2013 | Buesing | H05B 33/14 |
| | | | 252/500 |
| 2013/0240796 A1 * | 9/2013 | Parham | C07D 495/02 |
| | | | 544/333 |
| 2015/0349268 A1 | 12/2015 | Zeng et al. | |
| 2016/0164004 A1 * | 6/2016 | Seo | C07D 401/10 |
| | | | 257/40 |
| 2016/0322583 A1 * | 11/2016 | Kim | C09K 11/025 |
| 2018/0006243 A1 | 1/2018 | Yoo et al. | |
| 2018/0090686 A1 * | 3/2018 | Yoon | C07D 409/14 |
| 2019/0044072 A1 | 2/2019 | Sim et al. | |

FOREIGN PATENT DOCUMENTS

| | | |
|---|---|---|
| KR | 10-2018-0003220 A | 1/2018 |
| KR | 10-2018-0035358 A | 4/2018 |
| KR | 10-1846436 B1 | 4/2018 |
| KR | 10-2019-0002299 A | 1/2019 |
| KR | 10-1936071 B1 | 1/2019 |
| KR | 10-1937257 B1 | 1/2019 |
| KR | 10-2019-0015681 A | 2/2019 |

* cited by examiner

| 190 |
|-----|
| 150 |
| 110 |

| 190 |
|-----|
| 150 |
| 110 |
| 210 |

| 220 |
|---|
| 190 |
| 150 |
| 110 |

| 220 |
|---|
| 190 |
| 150 |
| 110 |
| 210 |

COMPOUND AND ORGANIC LIGHT-EMITTING DEVICE INCLUDING THE SAME

CROSS-REFERENCE TO RELATED APPLICATION

This application claims priority to and the benefit of Korean Patent Application No. 10-2019-0085206, filed on Jul. 15, 2019, in the Korean Intellectual Property Office, the entire content of which is incorporated herein by reference.

BACKGROUND

1. Field

One or more embodiments of the present disclosure relate to a compound and an organic light-emitting device including the same.

2. Description of the Related Art

Organic light-emitting devices (OLEDs) are self-emission devices that, as compared with other devices in the art, have wide viewing angles, high contrast ratios, short response times, and excellent characteristics in terms of brightness, driving voltage, and response speed, and produce full-color images.

The organic light-emitting device may include a first electrode on a substrate, and a hole transport region, an emission layer, an electron transport region, and a second electrode, which are sequentially on the first electrode. Holes provided from the first electrode may move toward the emission layer through the hole transport region, and electrons provided from the second electrode may move toward the emission layer through the electron transport region. Carriers, such as holes and electrons, recombine in the emission layer to produce excitons. Then, the excitons are transitioned (e.g., transition or relax) from an excited state to a ground state, thereby generating light.

SUMMARY

One or more embodiments of the present disclosure include a hole transport compound having high efficiency characteristics, as compared with an existing compound, and serving to suppress or reduce the generation of dark spots by chelating a metal that migrates from an electrode, and a device including the same.

Additional aspects of embodiments will be set forth in part in the description which follows and, in part, will be apparent from the description, or may be learned by practice of the presented embodiments.

An aspect of an embodiment of the present disclosure provides a compound represented by Formula 1:

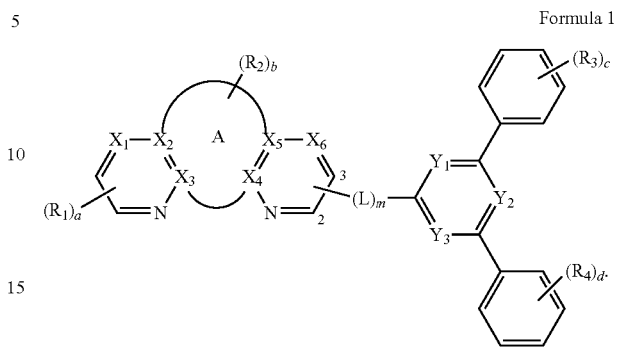

Formula 1

In Formula 1,
A may be a single bond linked $X_3$ with $X_4$, or A may be a fused $C_4$-$C_{60}$ carbocyclic group or a fused $C_1$-$C_{60}$ heterocyclic group,
$X_1$ may be N, C, or $C(R_{11})$, $X_2$ may be N, C, or $C(R_{12})$, $X_3$ may be N, C, or $C(R_{13})$, $X_4$ may be N, C, or $C(R_{14})$, $X_5$ may be N, C, or $C(R_{15})$, and $X_6$ may be N, C, or $C(R_{16})$,
$Y_1$ may be N or $C(R_{21})$, $Y_2$ may be N or $C(R_{22})$, $Y_3$ may be N or $C(R_{23})$, and at least one of $Y_1$ to $Y_3$ may be N,
$R_1$ to $R_4$, $R_{11}$ to $R_{16}$, and $R_{21}$ to $R_{23}$ may each independently be selected from hydrogen, deuterium, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$Si(Q_1)(Q_2)(Q_3)$, —$N(Q_1)(Q_2)$, —$B(Q_1)(Q_2)$, —$P(Q_1)(Q_2)$, —$C(=O)(Q_1)$, —$S(=O)_2(Q_1)$, and —$P(=O)(Q_1)(Q_2)$,
two neighboring substituents selected from $R_1$ to $R_4$, $R_{11}$ to $R_{16}$, and $R_{21}$ to $R_{23}$ may be linked with each other to form a ring,
When A is a single bond linking $X_3$ with $X_4$, each of $X_1$, $X_2$, $X_5$, and $X_6$ is CH, each of $X_3$ and $X_4$ is C, and $R_1$ may be excluded from being hydrogen,
L may be selected from a substituted or unsubstituted $C_4$-$C_{60}$ carbocyclic group and a substituted or unsubstituted $C_1$-$C_{60}$ heterocyclic group,
When A is benzene, L or a moiety including $Y_1$ to $Y_3$ may be linked with a carbon of position 3 (numerals 2 and 3 are carbon positions where L; or the moiety including $Y_1$ to $Y_3$ (m=0) is linked to the moiety including A),
m may be an integer from 0 to 3,
a may be 1 or 2,
b may be an integer from 1 to 4,
c and d may each independently be an integer from 1 to 5,
At least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ arylene group, the substituted $C_6$-$C_{60}$ aryloxy group, the substituted $C_6$-$C_{60}$ arylthio group, the substituted $C_1$-$C_{60}$ heteroaryl group, the substituted $C_1$-$C_{60}$ heteroarylene group, the substituted monovalent non-aromatic condensed polycyclic group, the substituted monovalent non-aromatic condensed heteropolycyclic group, the substituted $C_4$-$C_{60}$ carbocyclic group, and the substituted $C_1$-$C_{60}$ heterocyclic group may be selected from:

deuterium (-D), —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_1$ to $Q_3$, $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

Another aspect of an embodiment of the present disclosure provides an organic light-emitting device including:
a first electrode;
a second electrode facing the first electrode; and
an organic layer between the first electrode and the second electrode and including an emission layer,
wherein the organic layer includes the compound represented by Formula 1.

Another aspect of an embodiment of the present disclosure provides an electronic apparatus including a thin-film transistor and the organic light-emitting device, wherein the thin-film transistor includes a source electrode, a drain electrode, an activation layer, and a gate electrode, and the first electrode of the organic light-emitting device is in electrical contact with one of the source electrode and the drain electrode of the thin-film transistor.

BRIEF DESCRIPTION OF THE DRAWINGS

These and/or other aspects of embodiments will become apparent and more readily appreciated from the following description of the embodiments, taken in conjunction with the accompanying drawings in which:

FIGS. 1 to 4 are schematic views of a structure of an organic light-emitting device according to an embodiment.

DETAILED DESCRIPTION

Reference will now be made in more detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described herein below, by referring to the figures, to explain aspects of embodiments of the present description. As used herein, the term "and/or" includes any and all combinations of one or more of the associated listed items. Expressions such as "at least one of," when preceding a list of elements, modify the entire list of elements and do not modify the individual elements of the list.

External quantum efficiency (next) used in a light-emitting material layer may be obtained (or calculated) utilizing the following equation.

$$\eta_{ext} = \eta_{int} \times \Gamma \times \Phi \times \eta_{out\text{-}coupling}$$

(wherein, $\eta_{int}$: internal quantum efficiency, $\Gamma$: charge balance factor, $\Phi$: radiative quantum efficiency, $\eta_{out\text{-}coupling}$: out coupling efficiency).

Charge balance factor (r) refers to a balance of a hole and an electron forming an exciton and generally has a value of "1" on the assumption of 1:1 matching of 100%. Radiative quantum efficiency ($\Phi$) is a value involved in luminescence efficiency of an actual light-emitting material and depends on fluorescence quantum efficiency of a dopant in a host-dopant system.

Internal quantum efficiency ($\eta$int) refers to a ratio at which a generated exciton is converted into light that is emitted and has a limited value of up to 0.25 in the case of a fluorescent material. When a hole and an electron are recombined to form an exciton, singlet excitons and triplet excitons are generated at a ratio of 1:3 according to arrangements of electron spin. However, only the singlet excitons participate in light emission from the fluorescent material, and the remaining 75% of the triplet excitons do not participate in light emission from the fluorescent material.

Out coupling efficiency ($\eta_{out\text{-}coupling}$) refers to a ratio of light extracted to the outside from the emitted light. When isotropic molecules are thermally deposited to form a thin film, individual light-emitting molecules do not have a constant orientation (e.g., the same orientation) and exist in a random orientation state (e.g., the individual light-emitting molecules may be randomly oriented). Out coupling efficiency in such a random orientation state is generally assumed to be 0.2.

Therefore, in view of the above, maximum luminescence efficiency of an organic light-emitting diode device using a fluorescent material as the only light emitting material is about 5% or less. In order to overcome the low efficiency of the fluorescent material, a phosphorescent material has been developed which has a light-emitting mechanism that converts both singlet excitons and triplet excitons into light. In the case of red light and green light, a phosphorescent material having high luminescence efficiency has been developed, but in the case of blue light, a phosphorescent material having satisfactory luminescence efficiency and reliability has not been developed. Therefore, the development of a fluorescent material having satisfactory reliability and being capable of increasing luminescence efficiency by increasing quantum efficiency is desired.

An aspect of an embodiment of the present disclosure provides a compound represented by Formula 1:

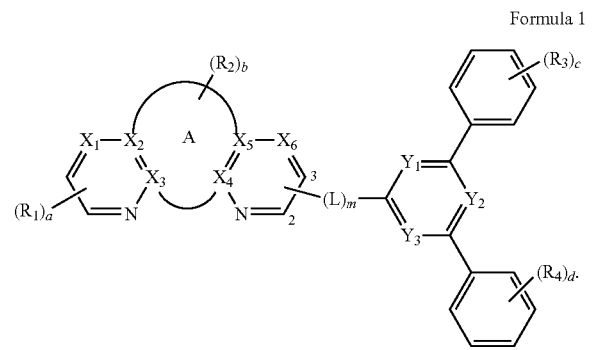

Formula 1

In Formula 1,

A may be a single bond linking $X_3$ with $X_4$, or A may be a fused $C_4$-$C_{60}$ carbocyclic group or a fused $C_1$-$C_{60}$ heterocyclic group, $X_1$ may be N, C, or $C(R_{11})$, $X_2$ may be N, C, or $C(R_{12})$, $X_3$ may be N, C, or $C(R_{13})$, $X_4$ may be N, C, or $C(R_{14})$, $X_5$ may be N, C, or $C(R_{15})$, and $X_6$ may be N, C, or $C(R_{16})$, $Y_1$ may be N or $C(R_{21})$, $Y_2$ may be N or $C(R_{22})$, $Y_3$ may be N or $C(R_{23})$, and at least one selected from $Y_1$ to $Y_3$ may be N, $R_1$ to $R_4$, $R_{11}$ to $R_{16}$, and $R_{21}$ to $R_{23}$ may each independently be selected from hydrogen, deuterium, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —P($Q_1$)($Q_2$), —C(=O)($Q_1$), —S(=O)$_2$($Q_1$), and —P(=O)($Q_1$)($Q_2$), two neighboring substituents selected from $R_1$ to $R_4$, $R_{11}$ to $R_{16}$, and $R_{21}$ to $R_{23}$ may be linked with each other to form a ring, When A is a single bond linking $X_3$ with $X_4$, each of $X_1$, $X_2$, $X_5$, and $X_6$ is CH, each of $X_3$ and $X_4$ is C, and $R_1$ may be excluded from being hydrogen, L may be selected from a substituted or unsubstituted $C_4$-$C_{60}$ carbocyclic group and a substituted or unsubstituted $C_1$-$C_{60}$ heterocyclic group, When A is benzene, L or a moiety including $Y_1$ to $Y_3$ may be linked with a carbon of position 3 (numerals 2 and 3 are carbon positions where L; or the moiety including $Y_1$ to $Y_3$ (m=0) is linked to the moiety including A), m may be an integer from 0 to 3, a may be 1 or 2, b may be an integer from 1 to 4, c and d may each independently be an integer from 1 to 5, at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ arylene group, the substituted $C_6$-$C_{60}$ aryloxy group, the substituted $C_6$-$C_{60}$ arylthio group, the substituted $C_1$-$C_{60}$ heteroaryl group, the substituted $C_1$-$C_{60}$ heteroarylene group, the substituted monovalent non-aromatic condensed polycyclic group, the substituted monovalent non-aromatic condensed heteropolycyclic group, the substituted $C_4$-$C_{60}$ carbocyclic group, and the substituted $C_1$-$C_{60}$ heterocyclic group may be selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)

$(Q_{12})(Q_{13})$, $-N(Q_{11})(Q_{12})$, $-B(Q_{11})(Q_{12})$, $-C(=O)(Q_{11})$, $-S(=O)_2(Q_{11})$, and $-P(=O)(Q_{11})(Q_{12})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, $-Si(Q_{21})(Q_{22})(Q_{23})$, $-N(Q_{21})(Q_{22})$, $-B(Q_{21})(Q_{22})$, $-C(=O)(Q_{21})$, $-S(=O)_2(Q_{21})$ and $-P(=O)(Q_{21})(Q_{22})$; and $-Si(Q_{31})(Q_{32})(Q_{33})$, $-N(Q_{31})(Q_{32})$, $-B(Q_{31})(Q_{32})$, $-C(=O)(Q_{31})$, $-S(=O)_2(Q_{31})$, and $-P(=O)(Q_{31})(Q_{32})$, and $Q_1$ to $Q_3$, $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

For example, when A is benzene and b is 2 or more, neighboring $R_2$(s) may be linked with each other to form a ring.

In the compound represented by Formula 1 according to one or more embodiments, a stabilized form of a molecular structure has a flat molecular structure without rotation (e.g., in the flat molecular structure the pendant groups are not rotated out of the plane of the molecule). This molecular structure was confirmed based on a result of geometry optimization using density functional theory calculations performed utilizing Dmol3 software (available from Accelrys). The flat molecular structure of embodiments of the present disclosure provides a strong oscillator strength, which causes the molecules of the compound represented by Formula 1 to be aligned in the same (e.g., substantially the same) direction during deposition. The alignment of the molecules in the same (e.g., substantially the same) direction facilitates hole and electron movement, as compared with a random molecular structure (and/or a random orientation of the deposited material).

For example, as an example of the compound represented by Formula 1, when a compound having the following structure is geometry-optimized,

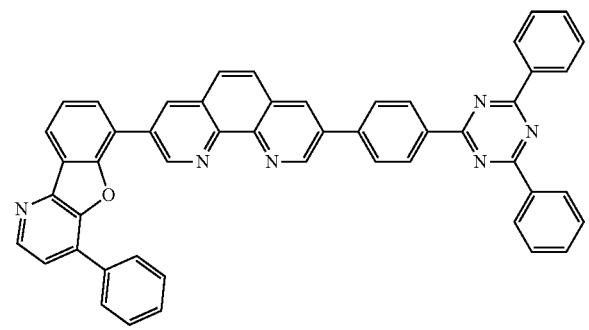 [SMILES: c1ccc(-c2nc(-c3ccccc3)nc(-c3ccc(-c4cnc5c(ccc6cc(-c7cccc8c7oc7c(-c9ccccc9)ccnc78)cnc65)c4)cc3)n2)cc1]

the following result may be obtained:

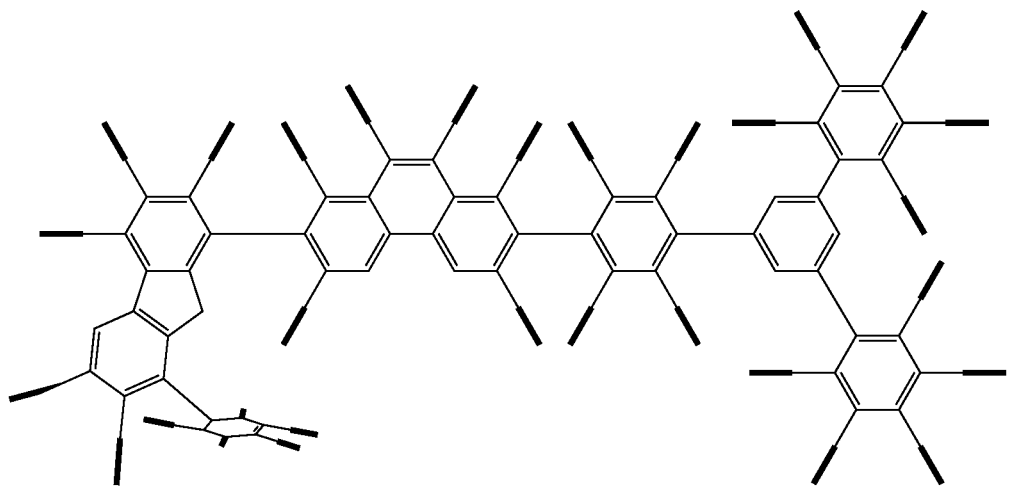

In some embodiments, the compound represented by Formula 1 includes two nitrogen atoms in

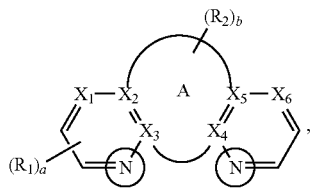

and thus, metal ion chelation by the compound represented by Formula 1 may be facilitated. Therefore, the diffusion into an emission layer is made impossible or unlikely by chelating metal ions migrating from an electrode. The generation of dark spots from metal ions that migrate from an electrode may be suppressed or reduced to prevent or reduce the occurrence of defective pixels of a panel.

In one embodiment, in Formula 1 $X_1$ to $X_6$ may each be $C(R_{11})$, $C(R_{12})$, $C(R_{13})$, $C(R_{14})$, $C(R_{15})$, $C(R_{16})$.

In one embodiment, in Formula 1 $X_2$ and $X_5$ may each be $C(R_{12})$ and $C(R_{15})$, and $X_1$ and $X_6$ may each be N.

In one embodiment, in Formula 1 $X_2$ and $X_5$ may each be N, and $X_1$ and $X_6$ may each be $C(R_{11})$ and $C(R_{16})$.

In one embodiment, A may be a single bond linking $X_3$ with $X_4$, a cyclopentane, a benzene, a naphthalene or a quinoxaline.

In one embodiment, in Formula 1 $R_2$ to $R_4$ may each be hydrogen or deuterium.

In one embodiment, in Formula 1 L may be a phenylene group, a naphthylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, or a triazinylene group. When m is 2 or more, each L may be the same or different.

In one embodiment, Formula 1 may be one of the following Formula 1-1 to 1-7:

Formula 1-1

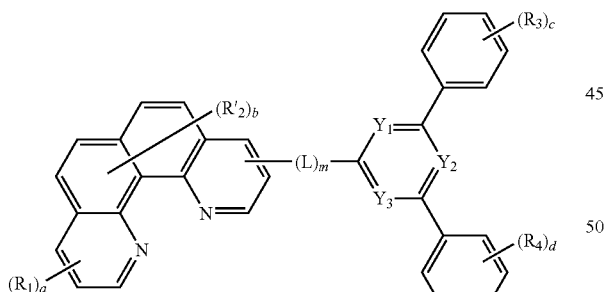

Formula 1-2

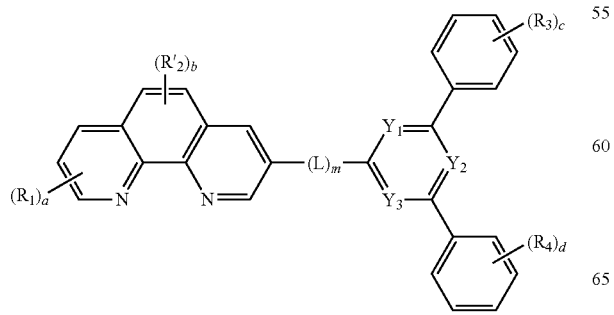

Formula 1-3

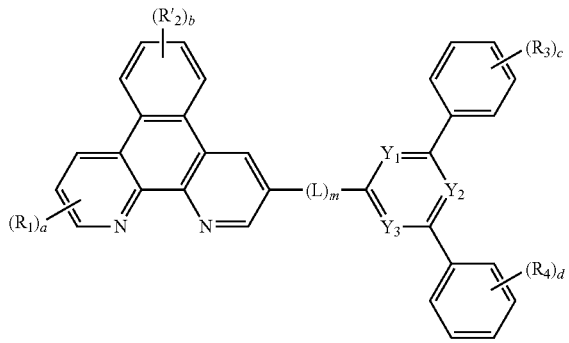

Formula 1-4

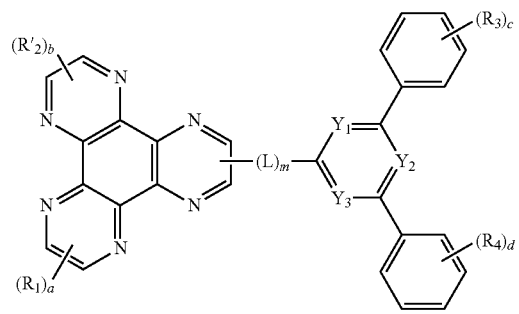

Formula 1-5

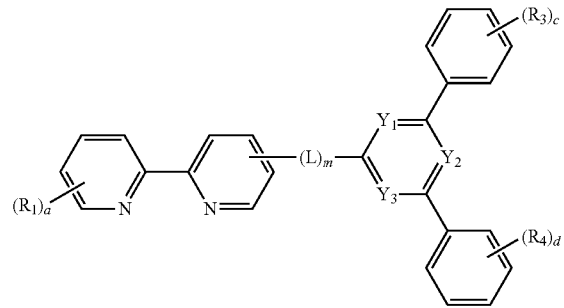

Formula 1-6

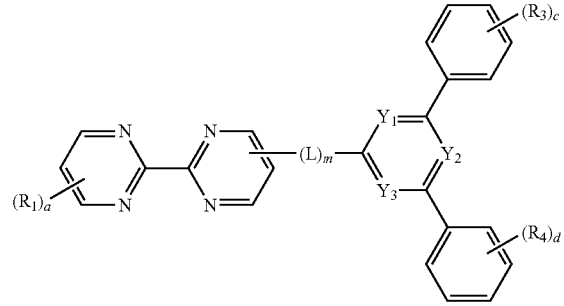

-continued

Formula 1-7

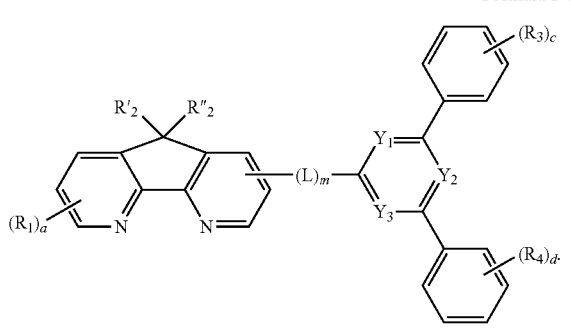

In Formulae 1-1 to 1-4 and 1-7, R'$_2$ and R"$_2$ may each independently be the same as defined in connection with R$_2$ in Formula 1. In Formula 1-5, R$_1$ may be excluded from being hydrogen. In Formulae 1-1 to 1-7, the substituents, subscripts, symbols, and the like may be the same as described with respect to Formula 1.

In one embodiment, R$_1$ in Formula 1 may be selected from hydrogen, deuterium, a phenyl group, a biphenyl group, a terphenyl group, a naphthyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a benzofuropyridyl group, a dibenzofuranyl group, a dibenzothiophenyl group, a triazinyl group, a benzimidazolyl group, and a phenanthrolinyl group.

In one embodiment, R$_1$ in Formula 1 may be hydrogen, deuterium, or a group represented by one of Formulae 2a and 2b:

2a

2b

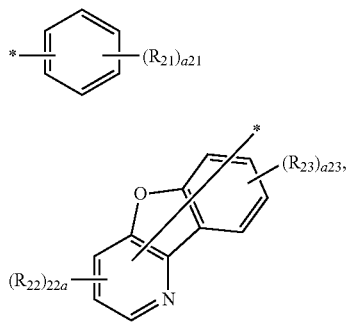

In Formulae 2a and 2b, R$_{21}$ to R$_{23}$ may each independently be selected from hydrogen, deuterium, —F, —Cl, —Br, —I, a hydroxyl group, a cyano group, a nitro group, an amino group, an amidino group, a hydrazino group, a hydrazono group, a carboxylic acid group or a salt thereof, a sulfonic acid group or a salt thereof, a phosphoric acid group or a salt thereof, a C$_1$-C$_{20}$ alkyl group, a C$_1$-C$_{20}$ alkoxy group, a phenyl group, a biphenyl group, a terphenyl group, a naphthyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a dibenzofuranyl group, a dibenzothiophenyl group, a triazinyl group, a benzimidazolyl group, and a phenanthrolinyl group, a21 may be an integer from 1 to 4, a22 may be 1 or 2, a23 may be an integer from 1 to 3, and * indicates a binding site to a neighboring atom. When a21, a22, and a23 are each 2 or more, two or more R$_{21}$(s), two or more R$_{22}$(s), and two or more R$_{23}$(s) may be identical to or different from each other.

In one embodiment, the compound represented by Formula 1 may be one of the following compounds:

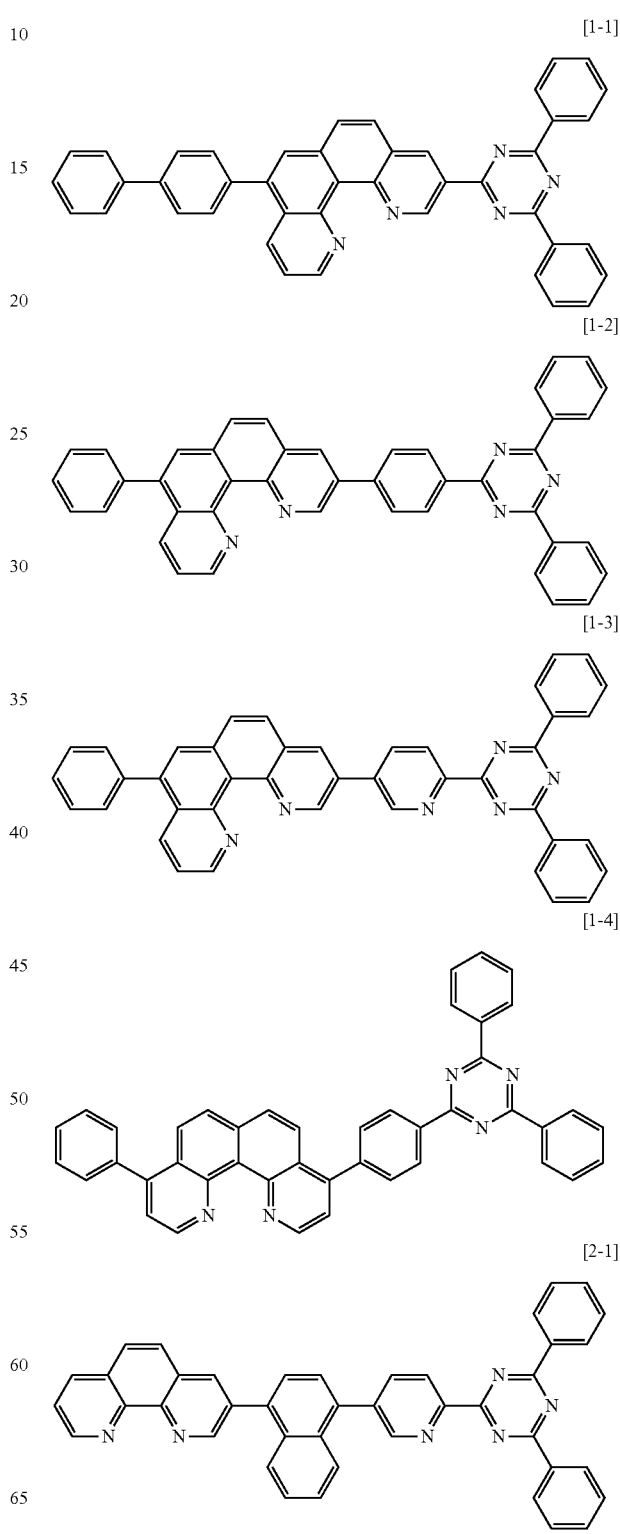

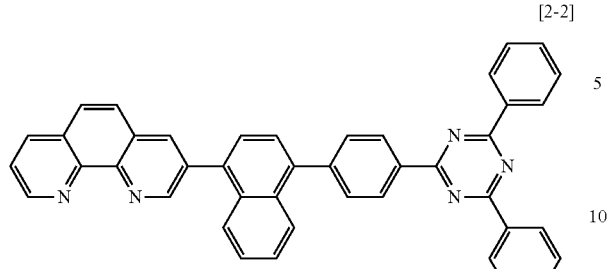
[2-2]
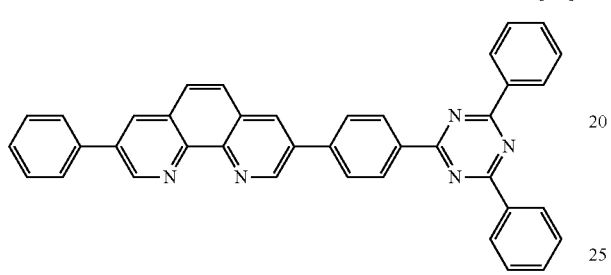
[2-3]
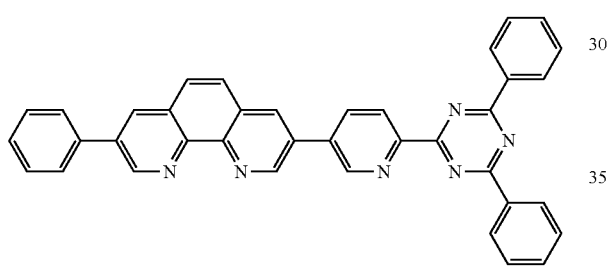
[2-4]
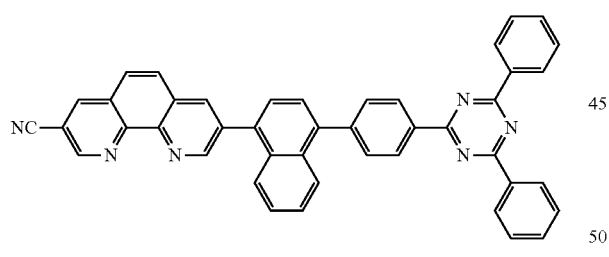
[2-5]
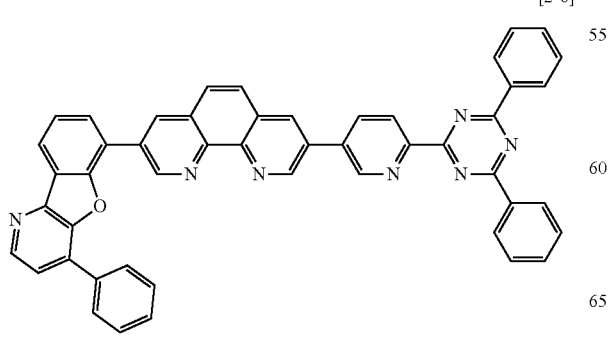
[2-6]
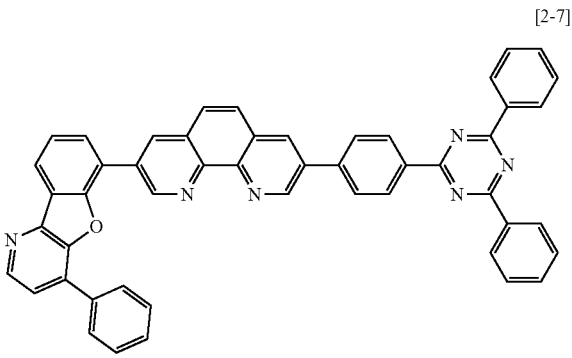
[2-7]
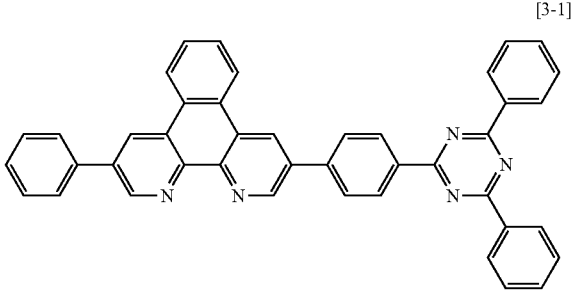
[3-1]
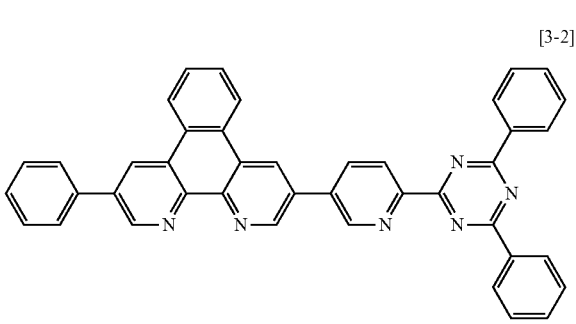
[3-2]
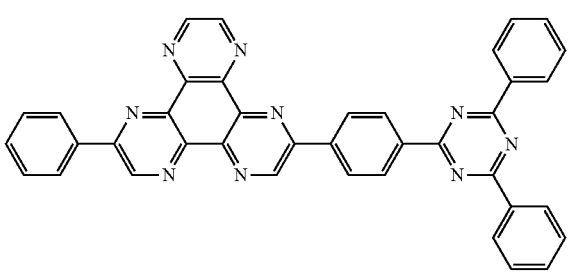
[4-1]
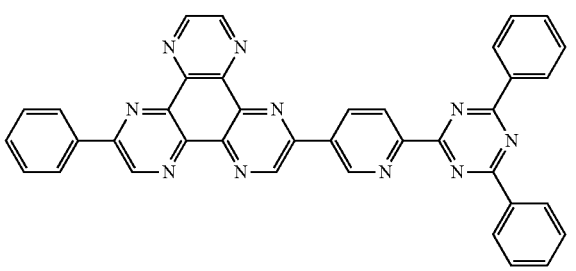
[4-2]

[5-1]
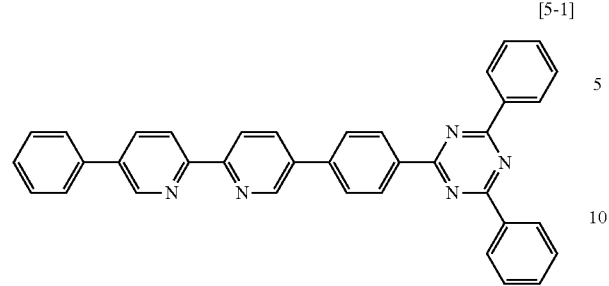
[5-2]
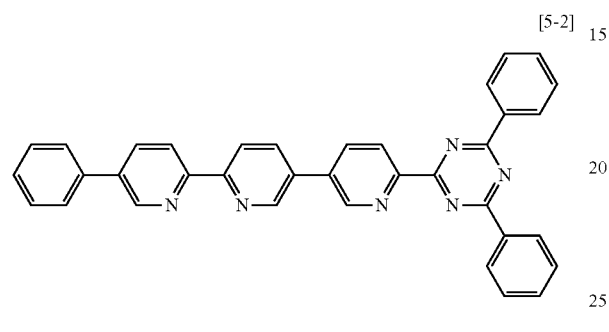
[6-1]
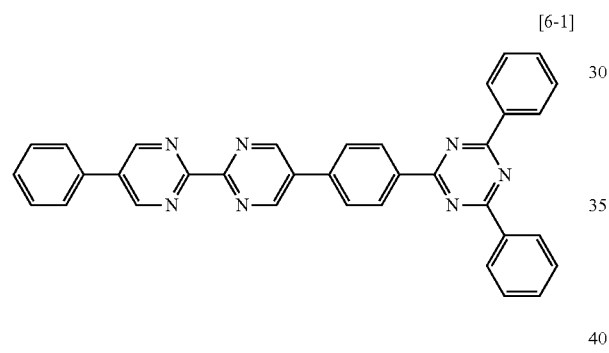
[6-2]
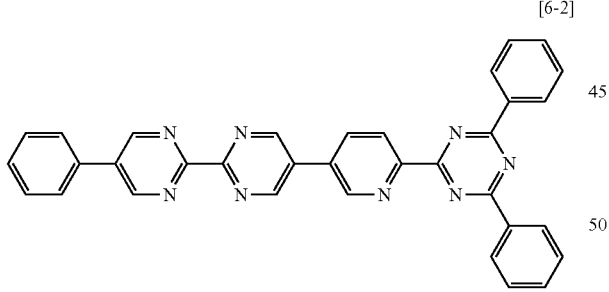
[7-1]
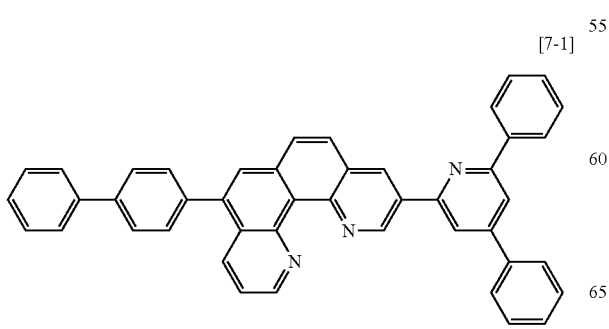
[7-2]
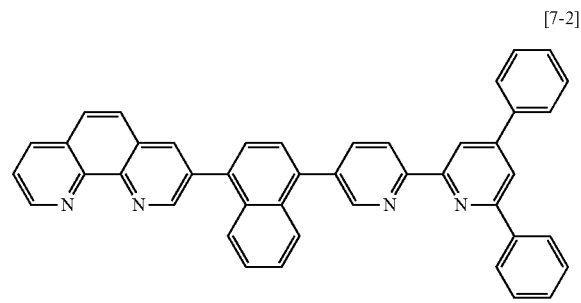
[7-3]
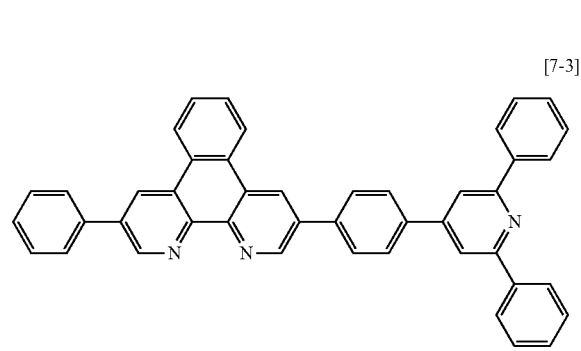
[7-4]
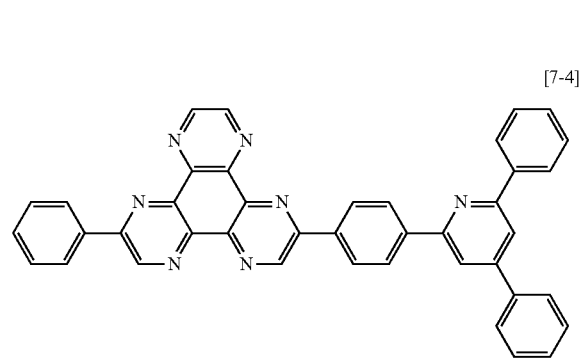
[7-5]
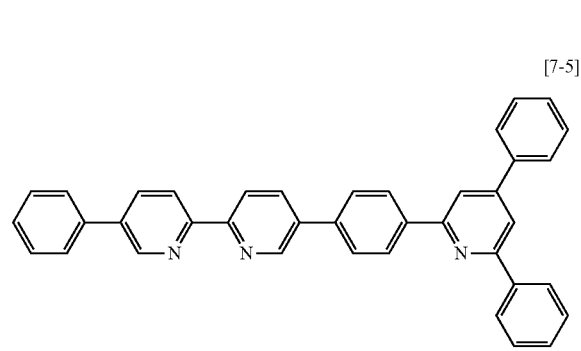
[7-6]
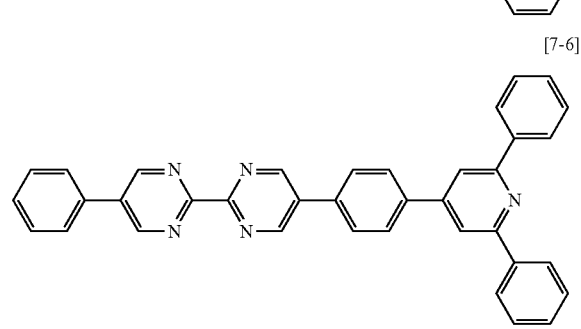

[7-7]
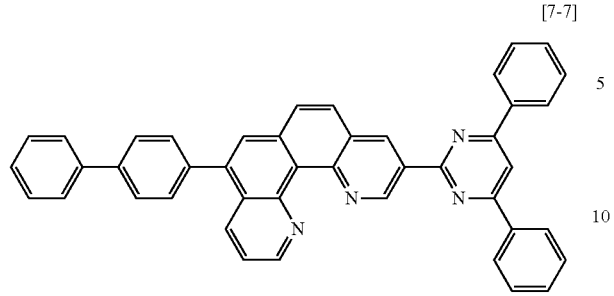

[7-8]
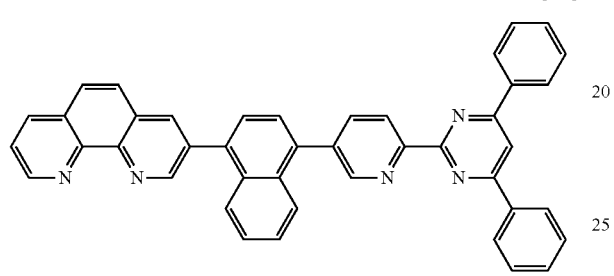

[7-9]
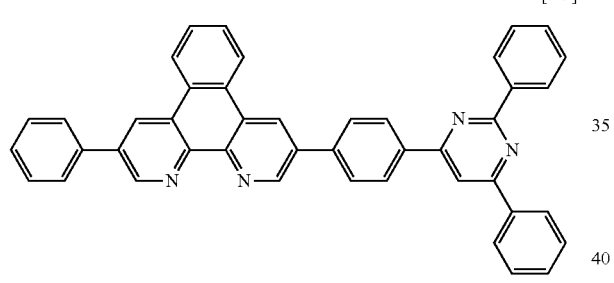

[7-10]
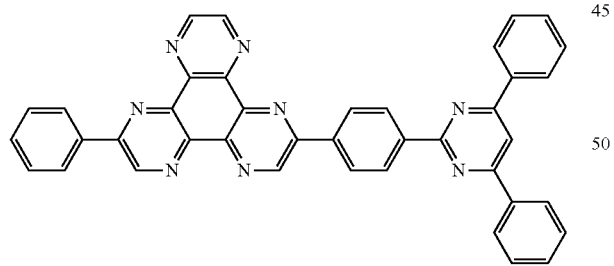

[7-11]
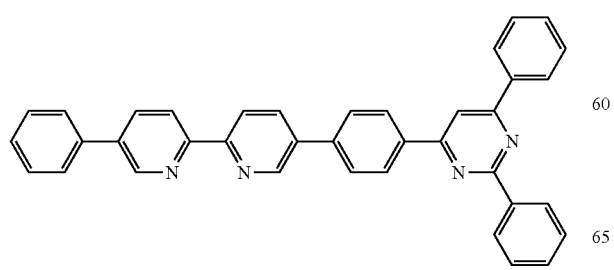

[7-12]
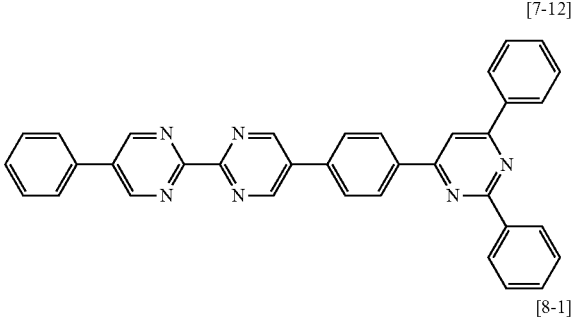

[8-1]
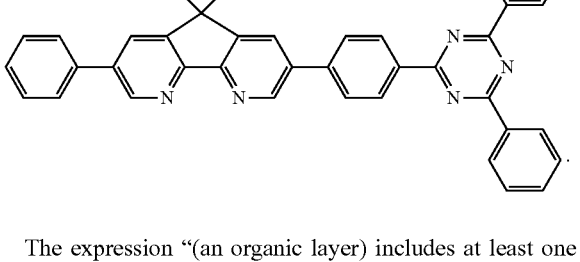

The expression "(an organic layer) includes at least one compound," as used herein, may include a case in which "(an organic layer) includes identical compounds represented by Formula 1" and a case in which "(an organic layer) includes two or more different compounds represented by Formula 1".

For example, the organic layer may include, as the compound represented by Formula 1, only Compound 1-1. In this regard, Compound 1-1 may exist only in the emission layer of the organic light-emitting device. In one or more embodiments, the organic layer may include, as the compound, Compound 1-1 and Compound 2-1. In this regard, Compound 1-1 and Compound 2-1 may exist in an identical layer (for example, Compound 1 and Compound 2 may all exist in an emission layer), or different layers (for example, Compound 1-1 may exist in an emission layer and Compound 2-1 may exist in an electron transport layer).

Another aspect of an embodiment of the present disclosure provides an organic light-emitting device including:
 a first electrode;
 a second electrode facing the first electrode; and
 an organic layer between the first electrode and the second electrode and including an emission layer,
 wherein the organic layer includes the compound represented by Formula 1.
In one embodiment,
 the first electrode of the organic light-emitting device may be an anode,
 the second electrode of the organic light-emitting device may be a cathode, and
 the organic layer may further include a hole transport region between the first electrode and the emission layer and an electron transport region between the emission layer and the second electrode,
 the hole transport region may include a hole injection layer, a hole transport layer, a buffer layer, an electron blocking layer, or any combination thereof, and
 the electron transport region may include a hole blocking layer, an electron transport layer, an electron injection layer, or any combination thereof.
In one embodiment, the emission layer may be a fluorescence emission layer.

In one embodiment, the compound represented by Formula 1 may be used in the hole transport region. For example, the compound represented by Formula 1 may be used in the hole transport layer.

Another aspect of an embodiment of the present disclosure provides an electronic apparatus including the organic light-emitting device and a thin-film transistor, wherein the first electrode of the organic light-emitting device may be in electrical contact with one of a source electrode and a drain electrode of the thin-film transistor.

The term "an organic layer," as used herein, refers to a single layer and/or a plurality of layers between the first electrode and the second electrode of an organic light-emitting device. A material included in the "organic layer" is not limited to an organic material.

Description of FIG. 1

Figures 1, 2:
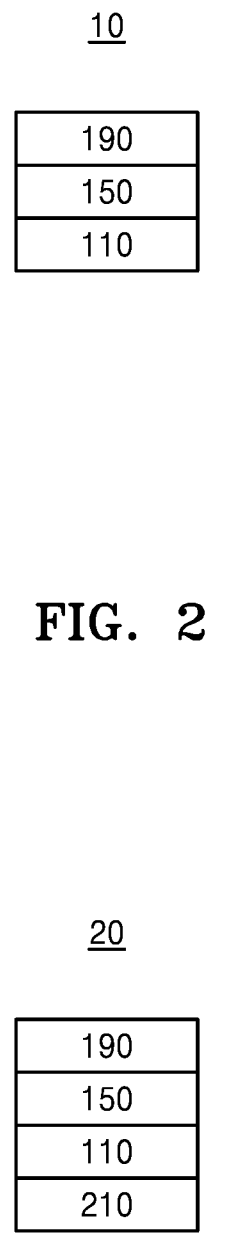

FIG. 1 is a schematic cross-sectional view of an organic light-emitting device 10 according to an embodiment. The organic light-emitting device 10 includes a first electrode 110, an organic layer 150, and a second electrode 190.

Hereinafter, the structure of an organic light-emitting device according to an embodiment and a method of manufacturing an organic light-emitting device according to an embodiment will be described in connection with FIG. 1.

First Electrode 110

In FIG. 1, a substrate may be additionally under the first electrode 110 or above the second electrode 190. For use as the substrate, the substrate may be a glass substrate or a plastic substrate, each having excellent mechanical strength, thermal stability, transparency, surface smoothness, ease of handling, and water resistance.

The first electrode 110 may be formed by depositing or sputtering a material for forming the first electrode 110 on the substrate. When the first electrode 110 is an anode, the material for forming the first electrode 110 may be selected from materials having a high work function to facilitate hole injection.

The first electrode 110 may be a reflective electrode, a semi-reflective electrode, or a transmissive electrode. When the first electrode 110 is a transmissive electrode, a material for forming a first electrode may be selected from indium tin oxide (ITO), indium zinc oxide (IZO), tin oxide ($SnO_2$), zinc oxide (ZnO), and any combinations thereof, but embodiments of the present disclosure are not limited thereto. In one or more embodiments, when the first electrode 110 is a semi-transmissive electrode or a reflectable electrode, a material for forming a first electrode may be selected from magnesium (Mg), silver (Ag), aluminum (Al), aluminum-lithium (Al—Li), calcium (Ca), magnesium-indium (Mg—In), magnesium-silver (Mg—Ag), and any combinations thereof, but embodiments of the present disclosure are not limited thereto.

The first electrode 110 may have a single-layered structure, or a multi-layered structure including two or more layers. For example, the first electrode 110 may have a three-layered structure of ITO/Ag/ITO, but the structure of the first electrode 110 is not limited thereto.

Organic Layer 150

The organic layer 150 is on the first electrode 110. The organic layer 150 may include an emission layer.

The organic layer 150 may further include a hole transport region between the first electrode 110 and the emission layer and an electron transport region between the emission layer and the second electrode 190.

Hole Transport Region in Organic Layer 150

The hole transport region may have i) a single-layered structure including a single layer including a single material, ii) a single-layered structure including a single layer including a plurality of different materials, or iii) a multi-layered structure having a plurality of layers including a plurality of different materials.

The hole transport region may include at least one layer selected from a hole injection layer, a hole transport layer, an emission auxiliary layer, and an electron blocking layer.

For example, the hole transport region may have a single-layered structure including a single layer including a plurality of different materials, or a multi-layered structure having a hole injection layer/hole transport layer structure, a hole injection layer/hole transport layer/emission auxiliary layer structure, a hole injection layer/emission auxiliary layer structure, a hole transport layer/emission auxiliary layer structure, or a hole injection layer/hole transport layer/electron blocking layer structure, wherein for each structure, constituting layers are sequentially stacked from the first electrode 110 in this stated order, but the structure of the hole transport region is not limited thereto.

The hole transport region may include at least one selected from m-MTDATA, TDATA, 2-TNATA, NPB (NPD), β-NPB, TPD, spiro-TPD, spiro-NPB, methylated-NPB, TAPC, HMTPD, 4,4',4"-tris(N-carbazolyl)triphenylamine (TCTA), PANI/DBSA (polyaniline/dodecylbenzenesulfonic acid), poly(3,4-ethylenedioxythiophene)/poly(4-styrenesulfonate) (PEDOT/PSS), polyaniline/camphor sulfonic acid (PANI/CSA), and polyaniline/poly(4-styrenesulfonate) (PANI/PSS):

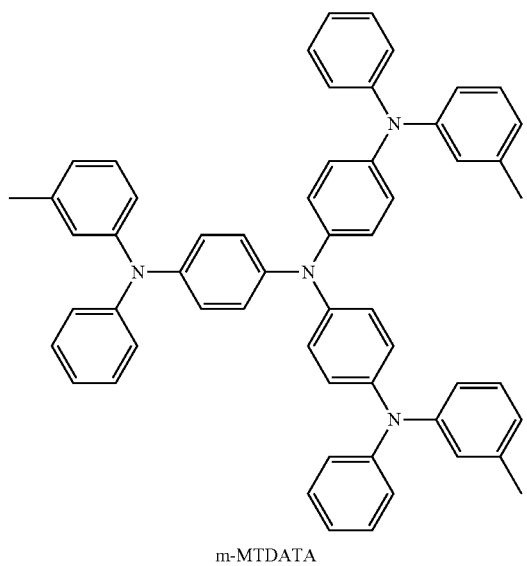

m-MTDATA

-continued
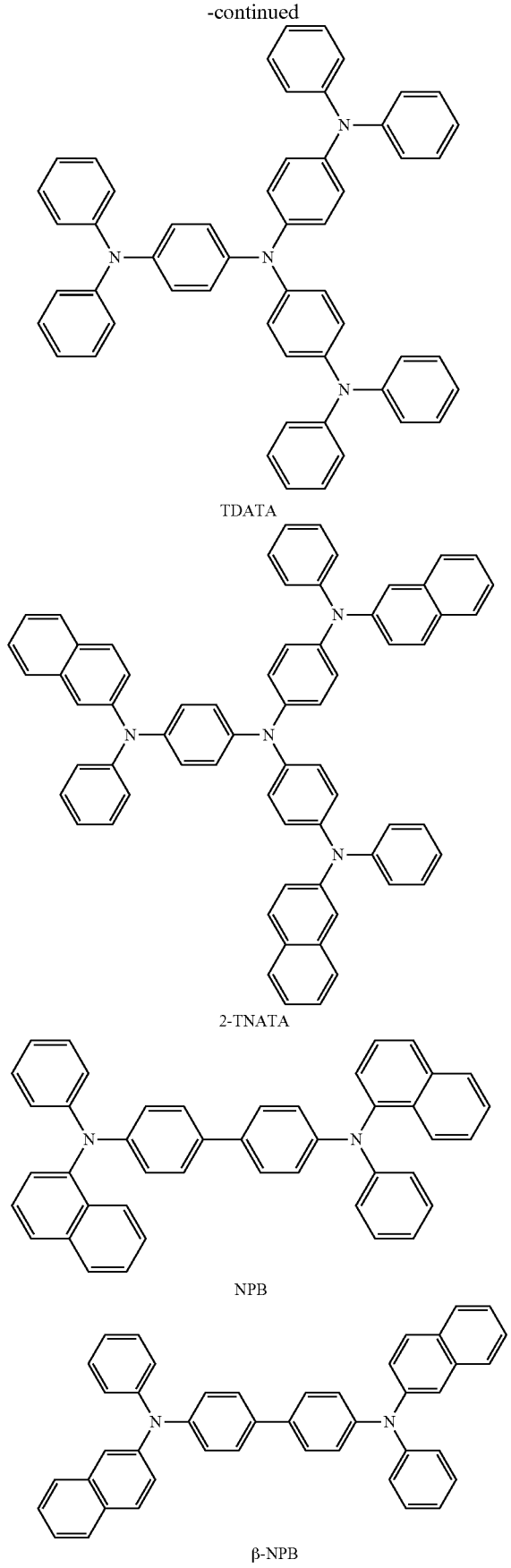
TDATA
2-TNATA
NPB
β-NPB
-continued
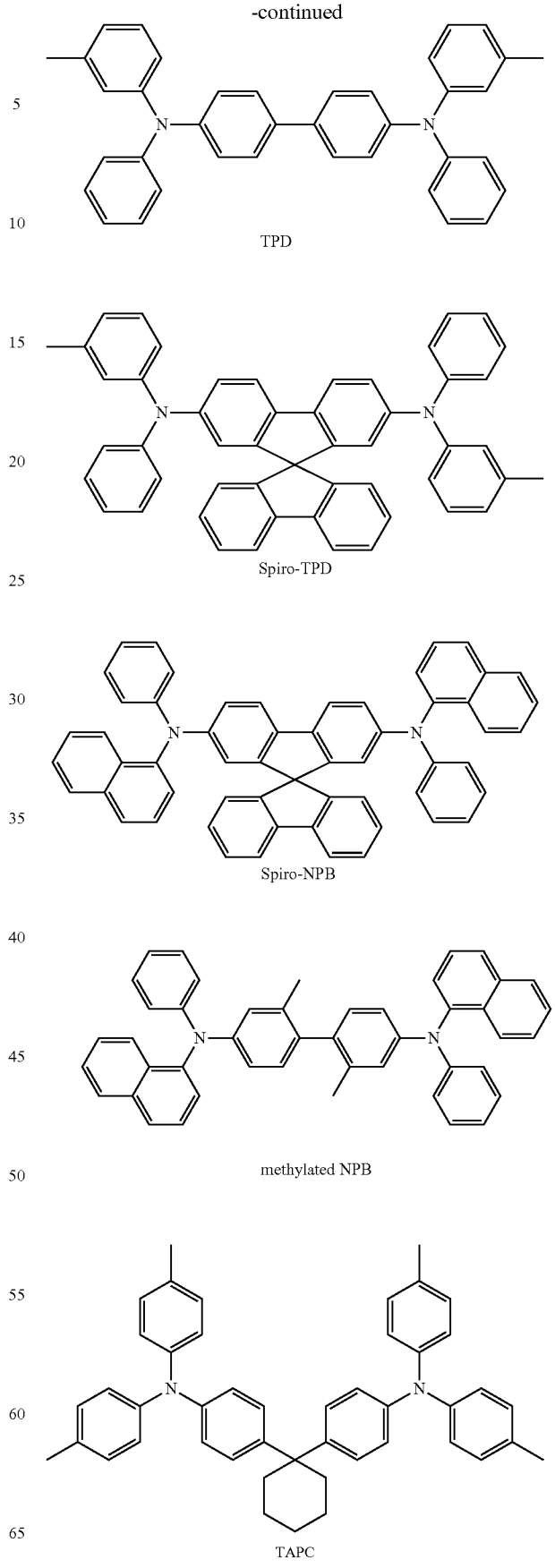
TPD
Spiro-TPD
Spiro-NPB
methylated NPB
TAPC

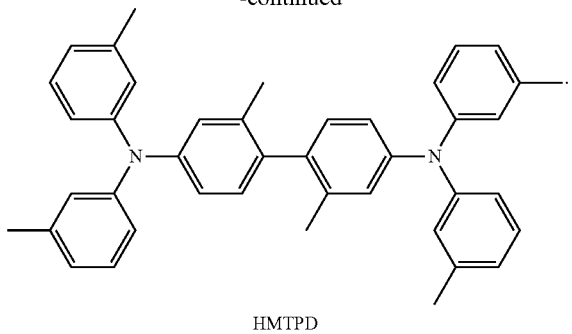

HMTPD

A thickness of the hole transport region may be from about 100 Å to about 10,000 Å, for example, about 100 Å to about 3,000 Å. When the hole transport region includes at least one selected from a hole injection layer and a hole transport layer, a thickness of the hole injection layer may be in a range of about 100 Å to about 9,000 Å, for example, about 100 Å to about 1,000 Å, and a thickness of the hole transport layer may be in a range of about 50 Å to about 2,000 Å, for example about 100 Å to about 1,500 Å. When the thicknesses of the hole transport region, the hole injection layer, and the hole transport layer are within these ranges, suitable or satisfactory hole transporting characteristics may be obtained without a substantial increase in driving voltage.

The emission auxiliary layer may increase light-emission efficiency by compensating for an optical resonance distance according to the wavelength of light emitted by an emission layer, and the electron blocking layer may block or reduce the flow of electrons from an electron transport region. The emission auxiliary layer and the electron blocking layer may include the materials as described herein above.

p-Dopant

The hole transport region may further include, in addition to these materials, a charge-generation material for the improvement of conductive (e.g., electrically conductive) properties. The charge-generation material may be homogeneously or non-homogeneously dispersed in the hole transport region.

The charge-generation material may be, for example, a p-dopant.

In one embodiment, the p-dopant may have a lowest unoccupied molecular orbital (LUMO) energy level of −3.5 eV or less.

The p-dopant may include at least one selected from a quinone derivative, a metal oxide, and a cyano group-containing compound, but embodiments of the present disclosure are not limited thereto.

In one embodiment, the p-dopant may include at least one selected from:
  a quinone derivative, such as tetracyanoquinodimethane (TCNQ) and 2,3,5,6-tetrafluoro-7,7,8,8-tetracyanoquinodimethane (F4-TCNQ);
  a metal oxide, such as tungsten oxide or molybdenum oxide;
  1,4,5,8,9,12-hexaazatriphenylene-hexacarbonitrile (HAT-CN); and
  a compound represented by Formula 221,
but embodiments of the present disclosure are not limited thereto:

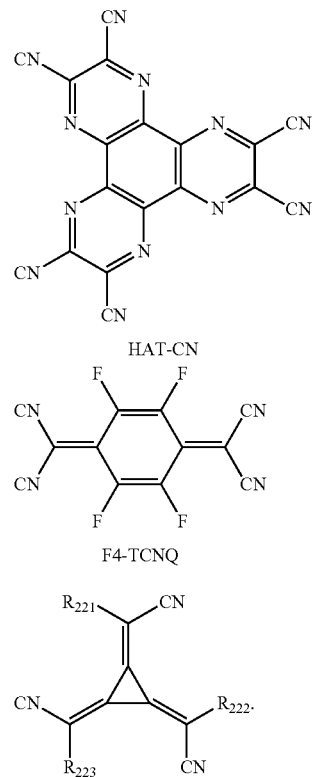

HAT-CN

F4-TCNQ

Formula 221

In Formula 221,
$R_{221}$ to $R_{223}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, wherein at least one of $R_{221}$ to $R_{223}$ may have at least one substituent selected from a cyano group, —F, —Cl, —Br, —I, a $C_1$-$C_{20}$ alkyl group substituted with —F, a $C_1$-$C_{20}$ alkyl group substituted with —Cl, a $C_1$-$C_{20}$ alkyl group substituted with —Br, and a $C_1$-$C_{20}$ alkyl group substituted with —I.

Emission Layer in Organic Layer 150

When the organic light-emitting device 10 is a full-color organic light-emitting device, the emission layer may be patterned into a red emission layer, a green emission layer, and a blue emission layer. In one or more embodiments, the emission layer may have a stacked structure of two or more layers selected from a red emission layer, a green emission layer, and a blue emission layer, in which the two or more layers contact each other or are separated from each other. In one or more embodiments, the emission layer may include two or more materials selected from a red light-emitting material, a green light-emitting material, and a blue light-emitting material, in which the two or more materials are mixed with each other in a single layer to emit white light.

The emission layer may include a host and a dopant. The dopant may include at least one selected from a phosphorescent dopant and a fluorescent dopant.

In the emission layer, an amount of the dopant may be in a range of about 0.01 parts by weight to about 15 parts by weight based on 100 parts by weight of the host, but embodiments of the present disclosure are not limited thereto.

A thickness of the emission layer may be in a range of about 100 Å to about 1,000 Å, for example, about 200 Å to about 600 Å. When the thickness of the emission layer is within this range, excellent emission characteristics may be obtained without a substantial increase in driving voltage.

The emission layer may include a host.

Host in Emission Layer

In one or more embodiments, the host may further include a compound represented by Formula 2 below:

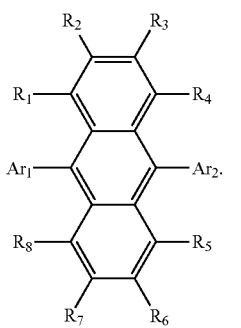

Formula 2

In Formula 2,

Ar$_1$ and Ar$_2$ may each independently be selected from a substituted or unsubstituted C$_6$-C$_{60}$ aryl group and a substituted or unsubstituted C$_1$-C$_{60}$ heteroaryl group, R$_1$ to R$_7$ may each independently be selected from hydrogen, deuterium, a substituted or unsubstituted C$_1$-C$_{60}$ alkyl group, a substituted or unsubstituted C$_6$-C$_{60}$ aryl group, a substituted or unsubstituted C$_1$-C$_{60}$ heteroaryl group, a substituted or unsubstituted monovalent non-aromatic condensed polycyclic group, and a substituted or unsubstituted monovalent non-aromatic condensed heteropolycyclic group, at least one substituent selected from the substituted C$_1$-C$_{60}$ alkyl group, the substituted C$_6$-C$_{60}$ aryl group, the substituted C$_1$-C$_{60}$ heteroaryl group, the substituted monovalent non-aromatic condensed polycyclic group, and the substituted monovalent non-aromatic condensed heteropolycyclic group may be selected from:

deuterium, —F, —Cl, —Br, —I, a hydroxyl group, a cyano group, a nitro group, an amidino group, a hydrazino group, a hydrazono group, a C$_1$-C$_{60}$ alkyl group, a C$_2$-C$_{60}$ alkenyl group, a C$_2$-C$_{60}$ alkynyl group, and a C$_1$-C$_{60}$ alkoxy group, a C$_1$-C$_{60}$ alkyl group, a C$_2$-C$_{60}$ alkenyl group, a C$_2$-C$_{60}$ alkynyl group, and a C$_1$-C$_{60}$ alkoxy group, each substituted with at least one selected from deuterium, —F, —Cl, —Br, —I, a hydroxyl group, a cyano group, a nitro group, an amidino group, a hydrazino group, a hydrazono group, a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, a monovalent non-aromatic condensed heteropolycyclic group, —Si(Q$_{11}$)(Q$_{12}$)(Q$_{13}$), —N(Q$_{11}$)(Q$_{12}$), —B(Q$_{11}$)(Q$_{12}$), —C(=O)(Q$_{11}$), —S(=O)$_2$(Q$_{11}$), and —P(=O)(Q$_{11}$)(Q$_{12}$);

a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, and a monovalent non-aromatic condensed heteropolycyclic group;

a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, a monovalent non-aromatic condensed heteropolycyclic group, —Si(Q$_{21}$)(Q$_{22}$)(Q$_{23}$), —N(Q$_{21}$)(Q$_{22}$), —B(Q$_{21}$)(Q$_{22}$), —C(=O)(Q$_{21}$), —S(=O)$_2$(Q$_{21}$), and —P(=O)(Q$_{21}$)(Q$_{22}$); and —Si(Q$_{31}$)(Q$_{32}$)(Q$_{33}$), —N(Q$_{31}$)(Q$_{32}$), —B(Q$_{31}$)(Q$_{32}$), —C(=O)(Q$_{31}$), —S(=O)$_2$(Q$_{31}$), and —P(=O)(Q$_{31}$)(Q$_{32}$), and Q$_1$ to Q$_3$, Q$_{11}$ to Q$_{13}$, Q$_{21}$ to Q$_{23}$, and Q$_{31}$ to Q$_{33}$ may each independently be selected from hydrogen, deuterium, —F, —Cl, —Br, —I, a hydroxyl group, a cyano group, a nitro group, an amidino group, a hydrazino group, a hydrazono group, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_1$-C$_{60}$ heteroaryl group, a monovalent non-aromatic condensed polycyclic group, a monovalent non-aromatic condensed heteropolycyclic group, a biphenyl group, and a terphenyl group.

The host may include at least one of the following compounds, but embodiments of the present disclosure are not limited thereto:

200-1
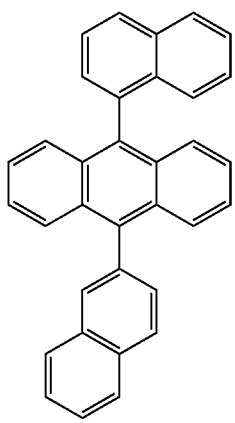
200-4
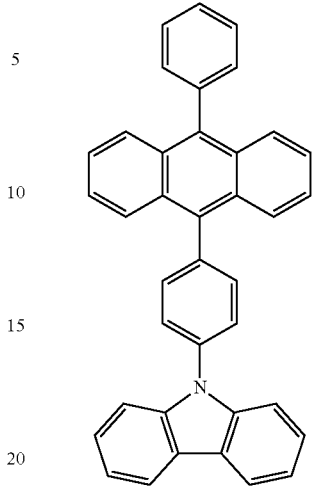
200-2
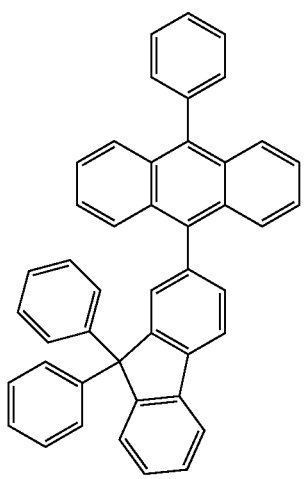
200-5
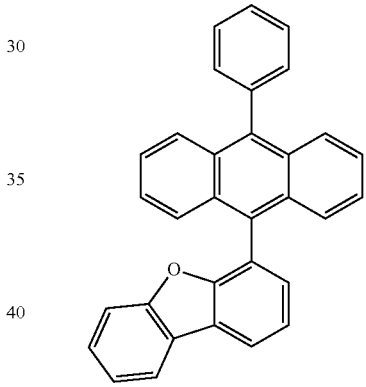
200-3
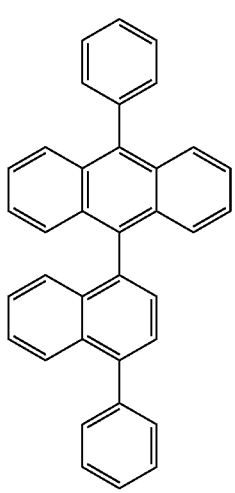
200-6
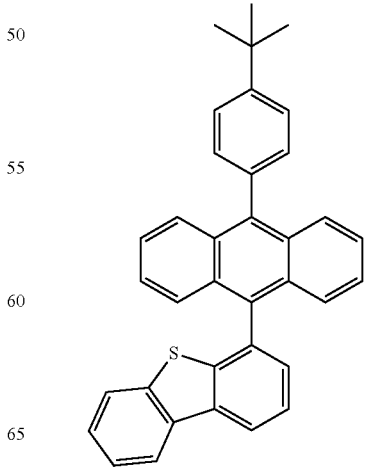

200-7 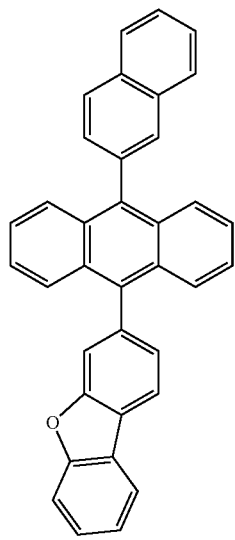
200-8 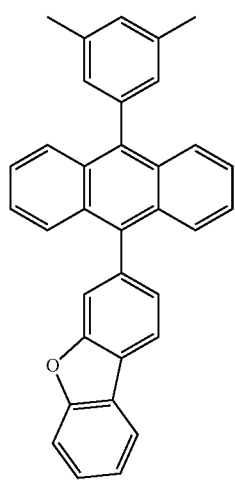
200-9 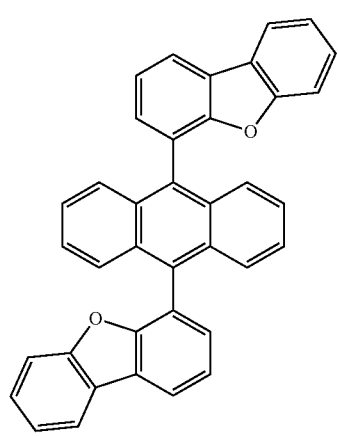
200-10 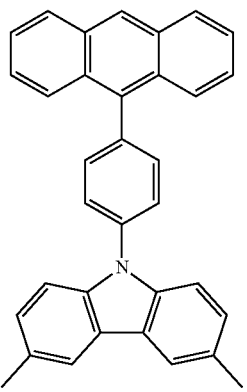
200-11 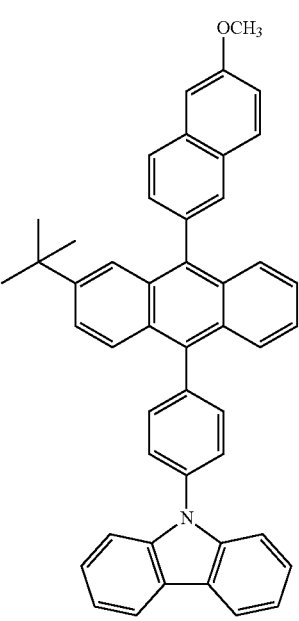
200-12 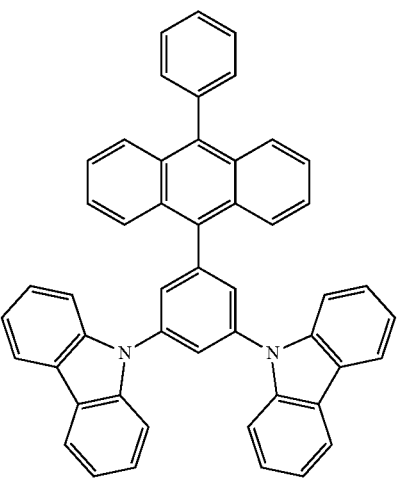

Phosphorescent Dopant Included in Emission Layer in Organic Layer 150

The phosphorescent dopant may include an organometallic complex represented by Formulae 401 or 402 below:

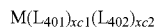

Formula 401

$M(L_{401})_{xc1}(L_{402})_{xc2}$

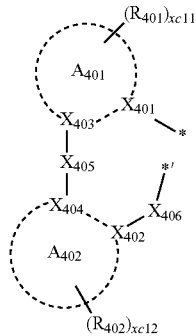

Formula 402

In Formulae 401 and 402,

M may be selected from iridium (Ir), platinum (Pt), palladium (Pd), osmium (Os), titanium (Ti), zirconium (Zr), hafnium (Hf), europium (Eu), terbium (Tb), rhodium (Rh), and thulium (Tm), $L_{401}$ may be selected from ligands represented by Formula 402, and xc1 may be 1, 2, or 3, wherein, when xc1 is 2 or more, two or more $L_{401}$(s) may be identical to or different from each other, $L_{402}$ may be an organic ligand, and xc2 may be an integer from 0 to 4, wherein, when xc2 is two or more, two or more $L_{402}$(s) may be identical to or different from each other, $X_{401}$ to $X_{404}$ may each independently be nitrogen or carbon, $X_{401}$ and $X_{403}$ may be linked via a single bond or a double bond, and $X_{402}$ and $X_{404}$ may be linked via a single bond or a double bond, $A_{401}$ and $A_{402}$ may each independently be selected from a $C_5$-$C_{60}$ carbocyclic group or a $C_1$-$C_{60}$ heterocyclic group, $X_{405}$ may be a single bond, *—O—*', *—S—*', *—C(=O)—*', *—N($Q_{411}$)—*', *—C($Q_{411}$)($Q_{412}$)—*', *—C($Q_{411}$)=C($Q_{412}$)—*, *—C($Q_{411}$)=*', or *=C($Q_{411}$)=*', wherein $Q_{411}$ and $Q_{412}$ may each independently be hydrogen, deuterium, a $C_1$-$C_{20}$ alkyl group, a $C_1$-$C_{20}$ alkoxy group, a phenyl group, a biphenyl group, a terphenyl group, or a naphthyl group, $X_{406}$ may be a single bond, O, or S, $R_{401}$ and $R_{402}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{20}$ alkyl group, a substituted or unsubstituted $C_1$-$C_{20}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), and —P(=O)($Q_{401}$)($Q_{402}$), wherein $Q_{401}$ to $Q_{403}$ may each independently be selected from a $C_1$-$C_{10}$ alkyl group, a $C_1$-$C_{10}$ alkoxy group, a $C_6$-$C_{20}$ aryl group, and a $C_1$-$C_{20}$ heteroaryl group, xc11 and xc12 may each independently be an integer from 0 to 10, and

* and *' in Formula 402 each indicate a binding site to M in Formula 401.

In one embodiment, $A_{401}$ and $A_{402}$ in Formula 402 may each independently be selected from a benzene group, a naphthalene group, a fluorene group, a spiro-bifluorene group, an indene group, a pyrrole group, a thiophene group, a furan group, an imidazole group, a pyrazole group, a thiazole group, an isothiazole group, an oxazole group, an isoxazole group, a pyridine group, a pyrazine group, a pyrimidine group, a pyridazine group, a quinoline group, an isoquinoline group, a benzoquinoline group, a quinoxaline group, a quinazoline group, a carbazole group, a benzimidazole group, a benzofuran group, a benzothiophene group, an isobenzothiophene group, a benzoxazole group, an isobenzoxazole group, a triazole group, a tetrazole group, an oxadiazole group, a triazine group, a dibenzofuran group, and a dibenzothiophene group.

In one or more embodiments, in Formula 402, i) $X_{401}$ may be nitrogen, and $X_{402}$ may be carbon, or ii) $X_{401}$ and $X_{402}$ may each be nitrogen at the same time.

In one or more embodiments, $R_{401}$ and $R_{402}$ in Formula 402 may each independently be selected from:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, a hydrazono group, a phenyl group, a naphthyl group, a cyclopentyl group, a cyclohexyl group, an adamantanyl group, a norbornanyl group, and a norbornenyl group;

a cyclopentyl group, a cyclohexyl group, an adamantanyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group;

a cyclopentyl group, a cyclohexyl group, an adamantanyl group, a norbornanyl group, a norbornenyl group a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, an adamantanyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group; and —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$) and —P(=O)($Q_{401}$)($Q_{402}$), $Q_{401}$ to $Q_{403}$ may each independently be selected from a $C_1$-$C_{10}$ alkyl group, a $C_1$-$C_{10}$ alkoxy group, a phenyl group, a biphenyl group, and a naphthyl group, but embodiments of the present disclosure are not limited thereto.

In one or more embodiments, when xc1 in Formula 401 is 2 or more, two $A_{401}$(s) in two or more $L_{401}$(s) may optionally be linked via $X_{407}$, which is a linking group, or two $A_{402}$(s) in two or more $L_{401}$(s) may optionally be linked via $X_{408}$, which is a linking group (see Compounds PD1 to PD4 and PD7). $X_{407}$ and $X_{408}$ may each independently be a single bond, *—O—*', *—S—*', *—C(=O)—*', *—N($Q_{413}$)—*', *—C($Q_{413}$)($Q_{414}$)—*', or *—C($Q_{413}$)=C($Q_{414}$)—*'(wherein $Q_{413}$ and $Q_{414}$ may each independently be hydrogen, deuterium, a $C_1$-$C_{20}$ alkyl group, a $C_1$-$C_{20}$ alkoxy group, a phenyl group, a biphenyl group, a terphenyl group, or a naphthyl group), but embodiments of the present disclosure are not limited thereto.

$L_{402}$ in Formula 401 may be a monovalent, divalent, or trivalent organic ligand. For example, $L_{402}$ may be selected from halogen, diketone (for example, acetylacetonate), carboxylic acid (for example, picolinate), —C(=O), isonitrile, —CN, and phosphorus (for example, phosphine, or phosphite), but embodiments of the present disclosure are not limited thereto.

In one or more embodiments, the phosphorescent dopant may be selected from, for example, Compounds PD1 to PD25, but embodiments of the present disclosure are not limited thereto:

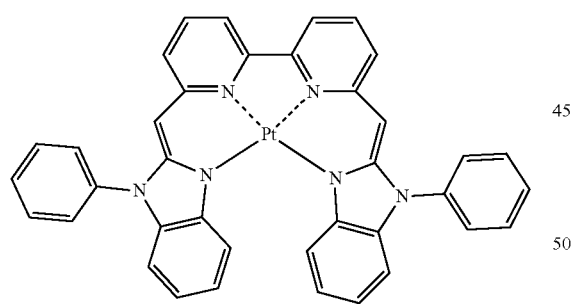

PD1

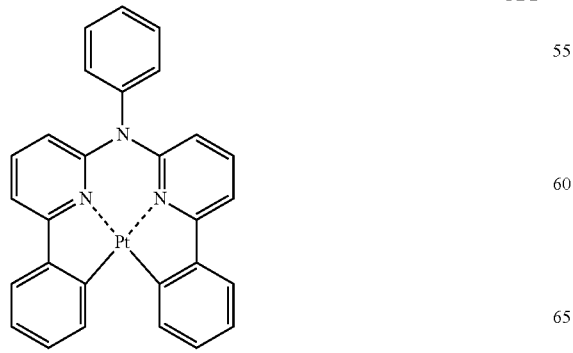

PD2

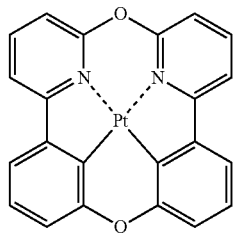

PD3

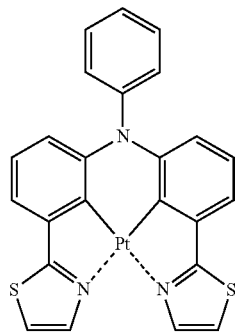

PD4

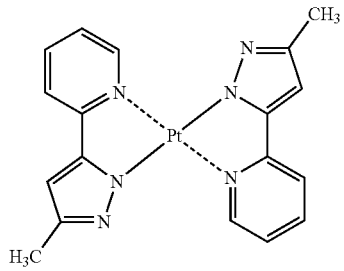

PD5

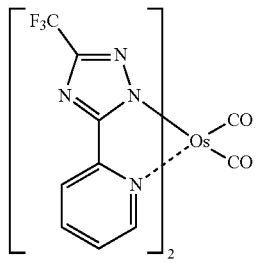

PD6

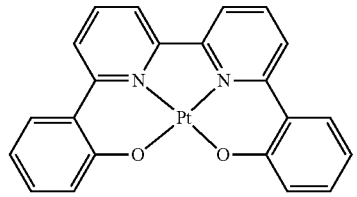

PD7

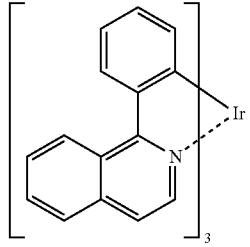

PD8

PD9 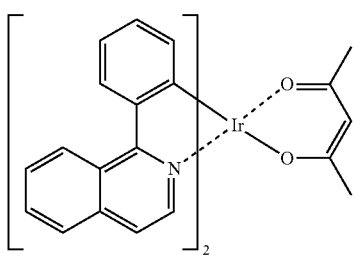
PD10 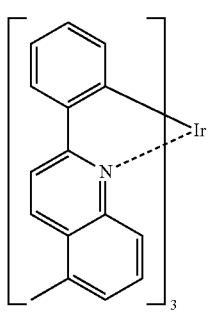
PD11 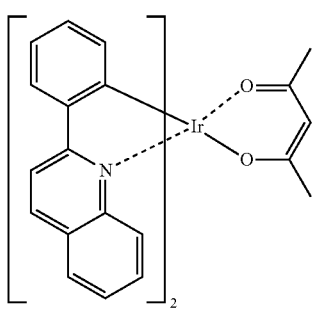
PD12 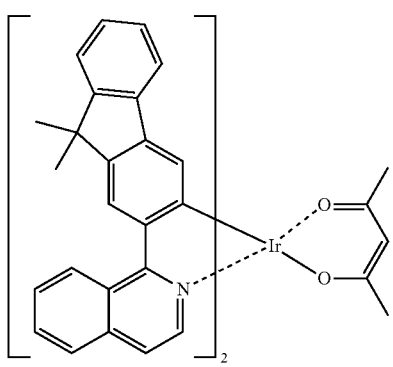
PD13 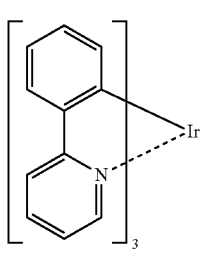
PD14 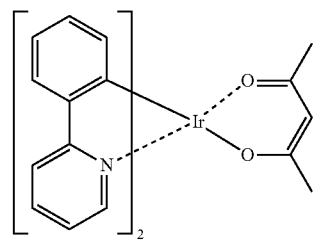
PD15 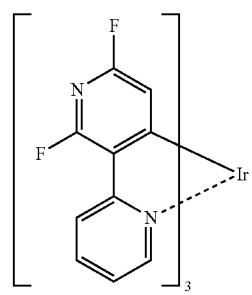
PD16 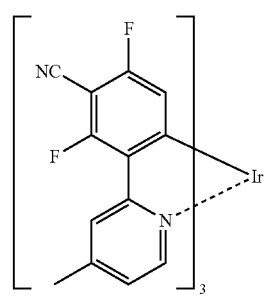
PD17 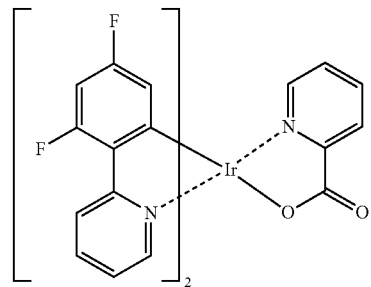
PD18 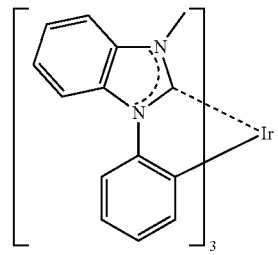

-continued

PD19
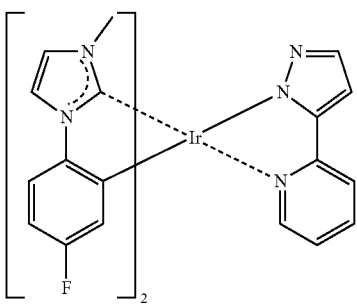

PD20
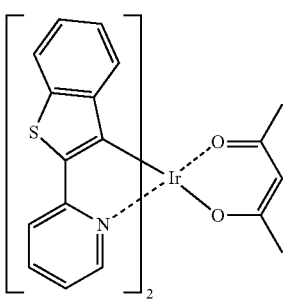

PD21
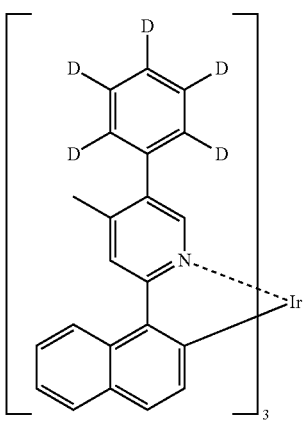

PD22
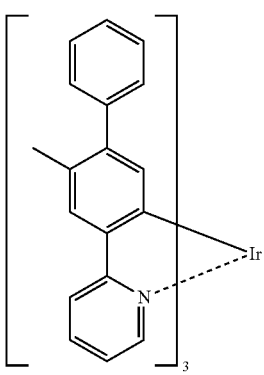

-continued

PD23
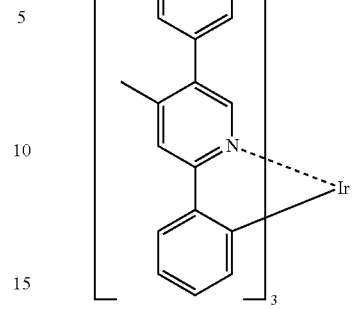

PD24
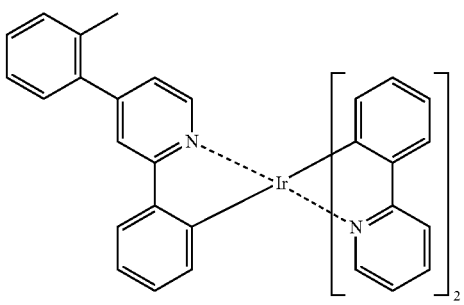

PD25
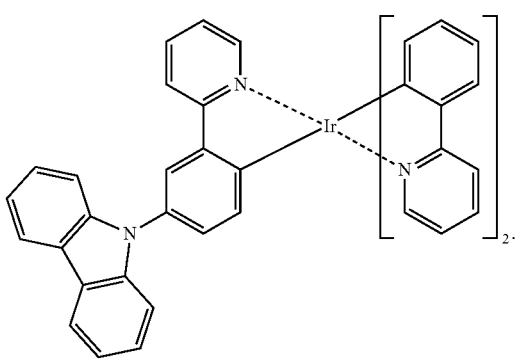

Fluorescent Dopant in Emission Layer

The fluorescent dopant may include an arylamine compound or a styrylamine compound.

The fluorescent dopant may include a compound represented by Formula 501 below:

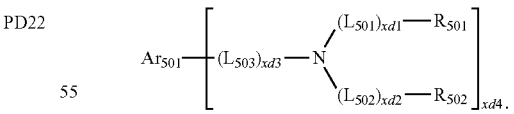

Formula 501

In Formula 501,

Ar$_{501}$ may be a substituted or unsubstituted C$_4$-C$_{60}$ carbocyclic group or a substituted or unsubstituted C$_1$-C$_{60}$ heterocyclic group, L$_{501}$ to L$_{503}$ may each independently be selected from a substituted or unsubstituted C$_3$-C$_{10}$ cycloalkylene group, a substituted or unsubstituted C$_1$-C$_{10}$ heterocycloalkylene group, a substituted or unsubstituted C$_3$-C$_{10}$ cycloalkenylene group, a substituted or unsubstituted C$_1$-C$_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xd1 to xd3 may each independently be an integer from 0 to 3, $R_{501}$ and $R_{502}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, and xd4 may be an integer from 1 to 6.

In one embodiment, in Formula 501, $Ar_{501}$ may be selected from:

a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group; and a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In one or more embodiments, $L_{501}$ to $L_{503}$ in Formula 501 may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

In one or more embodiments, $R_{501}$ and $R_{502}$ in Formula 501 may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, and —Si($Q_{31}$)($Q_{32}$)($Q_{33}$), and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In one or more embodiments, xd4 in Formula 501 may be 2, but embodiments of the present disclosure are not limited thereto.

For example, the fluorescent dopant may be selected from Compounds FD1 to FD22:

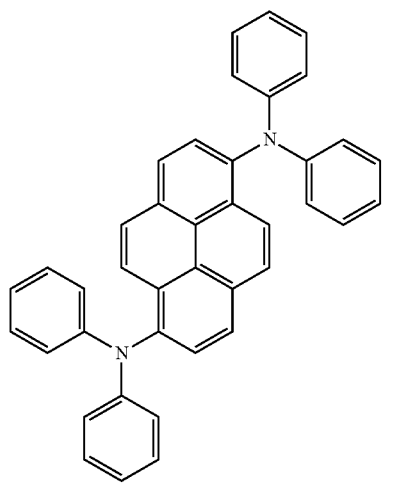

FD1

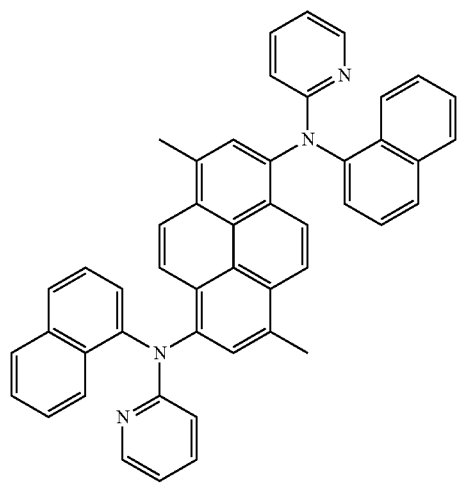

FD2

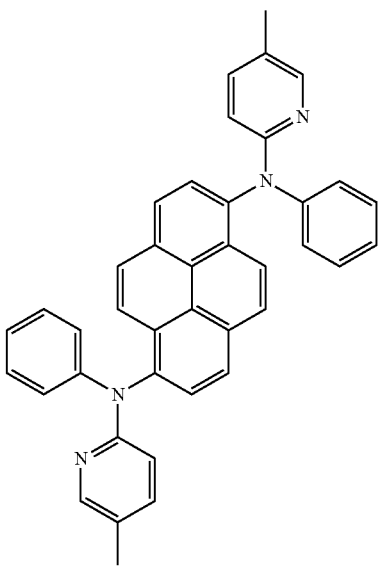

FD3

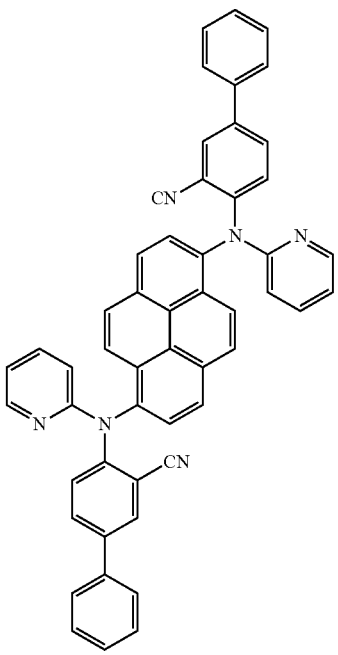

FD4

FD5
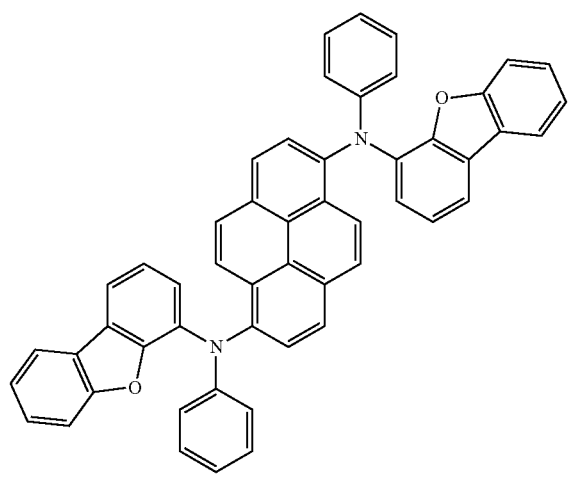
FD8
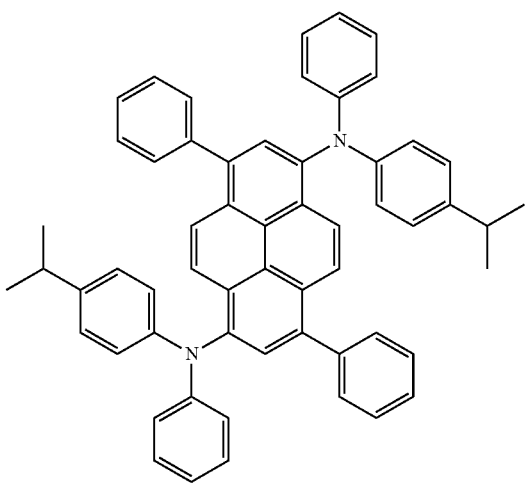
FD6
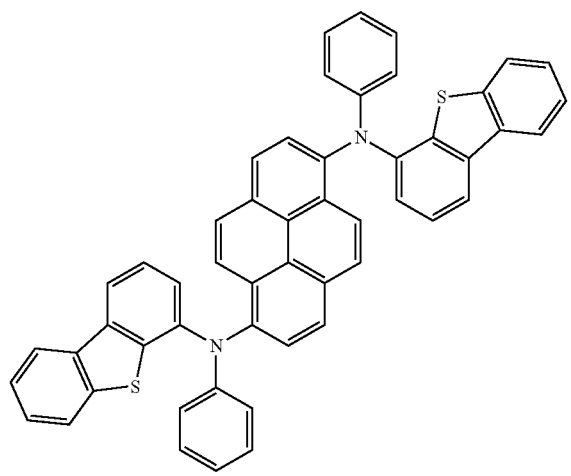
FD9
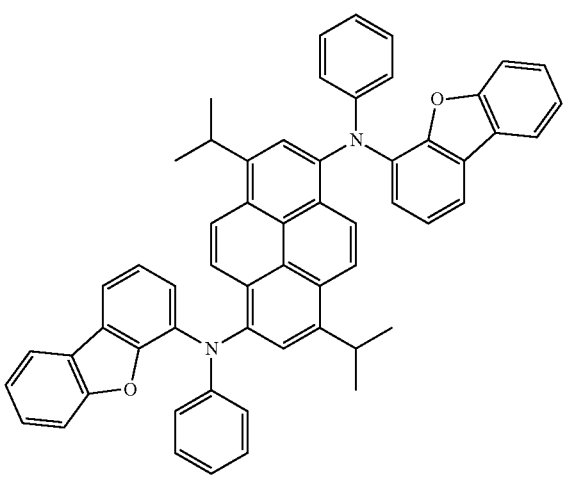
FD7
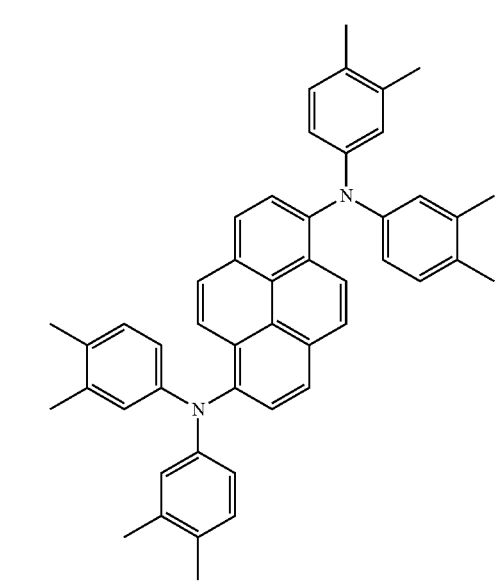
FD10
FD11

FD12
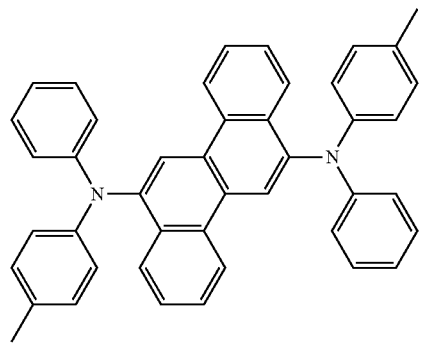
FD13
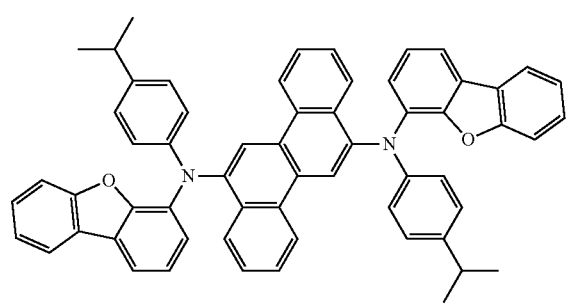
FD14
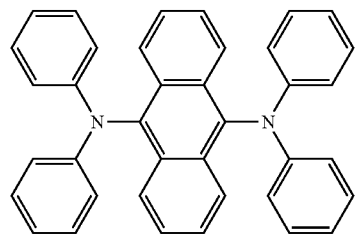
FD15
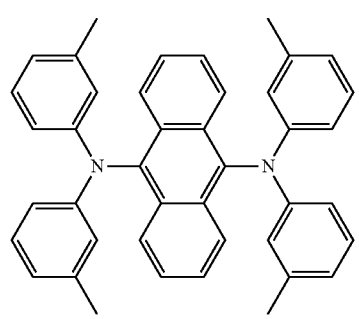
FD16
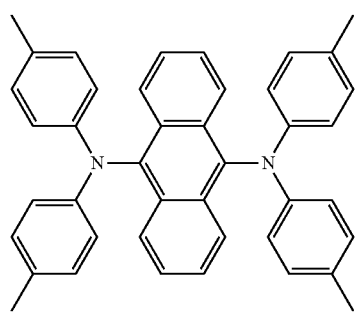
FD17
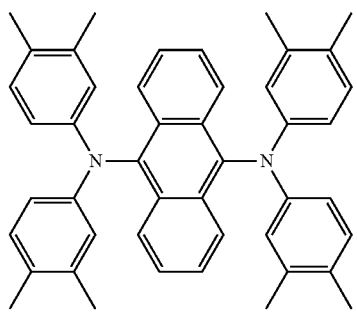
FD18
FD19
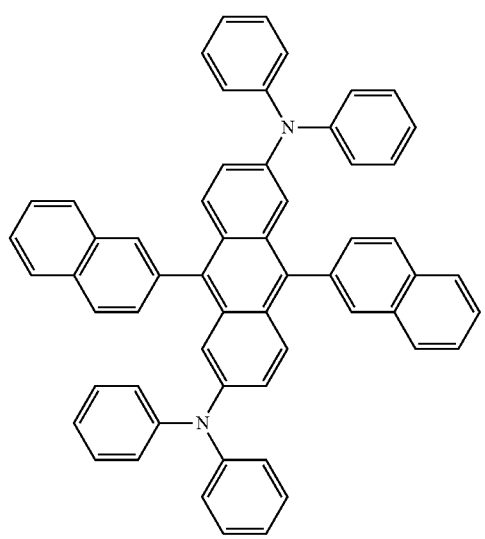
FD20
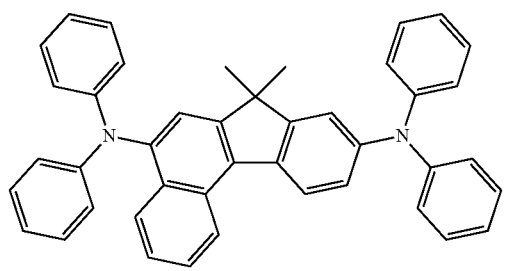

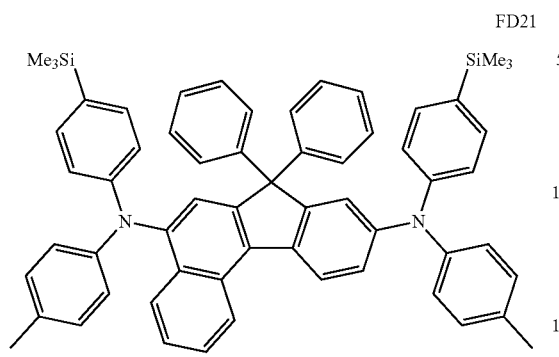
FD21
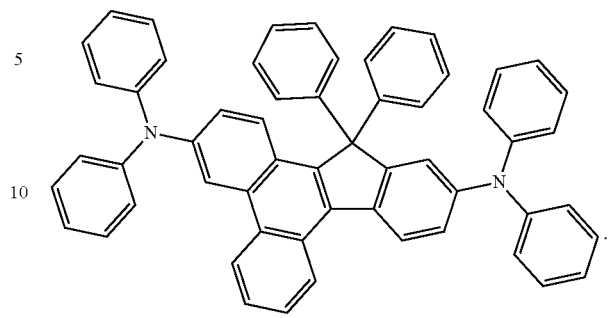
FD22
In one or more embodiments, the fluorescent dopant may be selected from the following compounds, but embodiments of the present disclosure are not limited thereto:
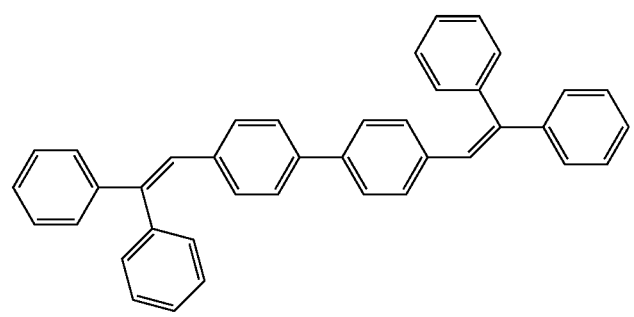
DPVBi
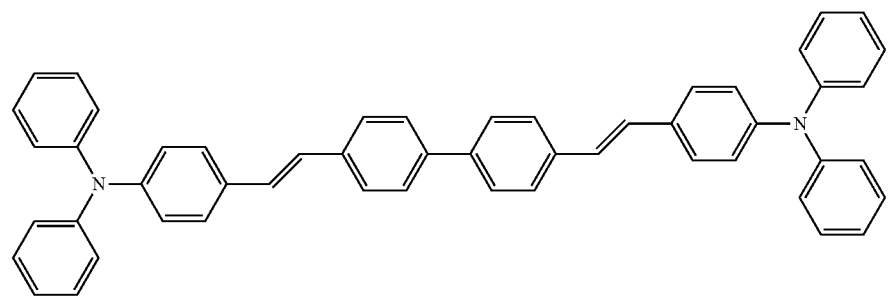
DPAVBi
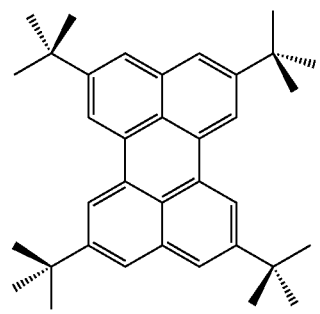
TBPe
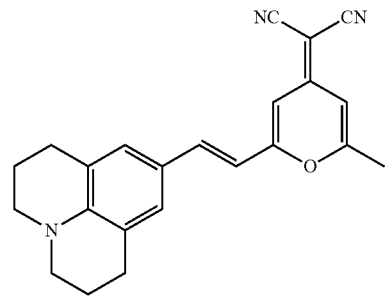
DCM

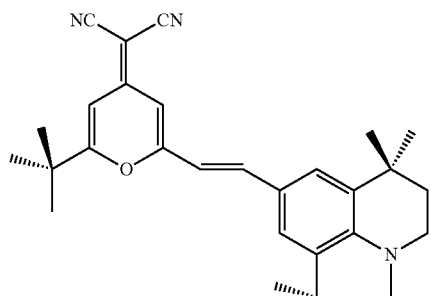

DCJTB

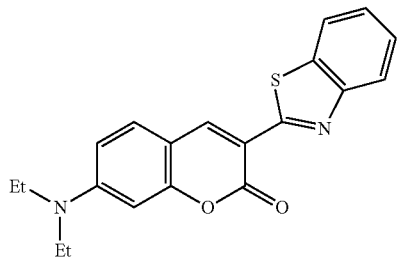

Coumarin 6

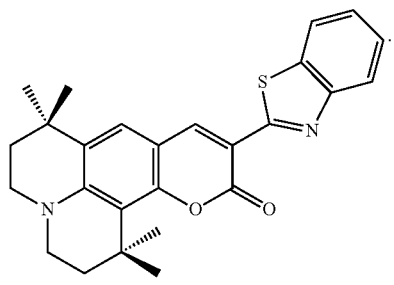

C545T

Quantum Dot in Emission Layer

In one embodiment, the emission layer included in the organic light-emitting device may include a quantum dot material.

The quantum dot is a particle having a crystal structure having a size of several to tens of nanometers and may include hundreds to thousands of atoms.

Because the quantum dot is very small in size, the quantum dot may exhibit a quantum confinement effect. The quantum confinement effect refers to a phenomenon in which a band gap of an object increases when the object becomes smaller than a nanometer size. Therefore, when light of a wavelength having an energy greater than the band gap of the quantum dot is irradiated onto the quantum dot, the quantum dot absorbs the light and is promoted to an excited state, and emits light of a set or specific wavelength when it returns to a ground state. At this time, the wavelength of the emitted light has a value corresponding to the band gap.

A core of the quantum dot may include a group II-VI compound, a group III-VI compound, a group III-V compound, a group IV-VI compound, a group IV compound, a group I-III-VI compound, or any mixture thereof.

The group IV-VI compound may be selected from: a binary compound selected from SnS, SnSe, SnTe, PbS, PbSe, PbTe, and any mixture thereof; a ternary compound selected from SnSeS, SnSeTe, SnSTe, PbSeS, PbSeTe, PbSTe, SnPbS, SnPbSe, SnPbTe, and any mixture thereof; and a quaternary compound selected from SnPbSSe, SnPbSeTe, SnPbSTe, and any mixture thereof. The group IV element may be selected from Si, Ge, and any mixture thereof. The group IV compound may be a binary compound selected from SiC, SiGe, and any mixture thereof.

The binary compound, the ternary compound, or the quaternary compound may exist in particles at uniform (e.g., substantially uniform) concentration, or may exist in the same particle in a state in which a concentration distribution is partially different. In addition, the binary compound, the ternary compound, or the quaternary compound may have a core-shell structure in which one quantum dot surrounds another quantum dot. An interface between the core and the shell may have a concentration gradient in which the concentration of certain atoms existing in the shell decreases along a direction toward the center.

In one or more embodiments, the quantum dot may have a core-shell structure including a core with the above-described nanoparticles and a shell surrounding the core. The shell of the quantum dot may serve as a protective layer for maintaining semiconductor characteristics by preventing or reducing chemical degeneration of the core and/or may serve as a charging layer for imparting electrophoretic characteristics to the quantum dot. The shell may be a single layer or a multilayer. An interface between the core and the shell may have a concentration gradient in which the concentration of certain atoms existing in the shell decreases along a direction toward the center. Examples of the shell of the quantum dot may include a metal or non-metal oxide, a semiconductor compound, or any combination thereof.

For example, examples of the metal or non-metal oxide may include a binary compound such as $SiO_2$, $Al_2O_3$, $TiO_2$, ZnO, MnO, $Mn_2O_3$, $Mn_3O_4$, CuO, FeO, $Fe_2O_3$, $Fe_3O_4$, CoO, $Co_3O_4$, NiO, or a ternary compound such as $MgAl_2O_4$, $CoFe_2O_4$, $NiFe_2O_4$, or $CoMn_2O_4$, but embodiments of the present disclosure are not limited thereto.

In addition, examples of the semiconductor compound may include CdS, CdSe, CdTe, ZnS, ZnSe, ZnTe, ZnSeS, ZnTeS, GaAs, GaP, GaSb, HgS, HgSe, HgTe, InAs, InP, InGaP, InSb, AlAs, AlP, AlSb, and the like, but embodiments of the present disclosure are not limited thereto.

A full width of half maximum (FWHM) of an emission wavelength spectrum of the quantum dot may be about 45 nm or less, for example, about 40 nm or less, for example, about 30 nm or less. When the FWHM of the emission wavelength spectrum of the quantum dot is within this range, color purity or color reproduction may be improved. In addition, light emitted through such quantum dot is irradiated in omnidirection (e.g., substantially every direction), thereby improving a wide viewing angle.

In addition, the quantum dot is a quantum dot generally used in the art, and is not particularly limited. For example, a spherical, pyramidal, multi-arm, or cubic nanoparticle, nanotube, nanowire, nanofiber, or nanoplate particle may be used.

The quantum dot may adjust the color of emitted light according to the particle size. Therefore, the quantum dot may be configured to emit various suitable emission colors such as blue, red, or green.

Electron Transport Region in Organic Layer 150

The electron transport region may have i) a single-layered structure including a single layer including a single material, ii) a single-layered structure including a single layer including a plurality of different materials, or iii) a multi-layered structure having a plurality of layers including a plurality of different materials.

The electron transport region may include at least one selected from a hole blocking layer, an electron control layer, an electron transport layer, and an electron injection layer, but embodiments of the present disclosure are not limited thereto.

For example, the electron transport region may have an electron transport layer/electron injection layer structure, a hole blocking layer/electron transport layer/electron injection layer structure, an electron control layer/electron transport layer/electron injection layer structure, or an electron transport layer/electron injection layer structure, wherein for each structure, constituting layers are sequentially stacked from an emission layer. However, embodiments of the structure of the electron transport region are not limited thereto.

The electron transport region may include the organic layer including the compound represented by Formula 1.

The electron transport region may further include, in addition to the compound represented by Formula 1, for example, a compound represented by Formula 601:

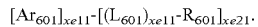   Formula 601

In Formula 601, $Ar_{601}$ may be a substituted or unsubstituted $C_4$-$C_{60}$ carbocyclic group or a substituted or unsubstituted $C_1$-$C_{60}$ heterocyclic group, xe11 may be 1, 2, or 3, $L_{601}$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xe1 may be an integer from 0 to 5, $R_{601}$ may be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{601}$)($Q_{602}$)($Q_{63}$), —C(=O)($Q_{601}$), —S(=O)$_2$($Q_{601}$), and —P(=O)($Q_{601}$)($Q_{602}$), $Q_{601}$ to $Q_{603}$ may each independently be a $C_1$-$C_{10}$ alkyl group, a $C_1$-$C_{10}$ alkoxy group, a phenyl group, a biphenyl group, a terphenyl group, or a naphthyl group, and xe21 may be an integer from 1 to 5.

In one embodiment, at least one of $Ar_{601}$(s) in the number of xe11 and $R_{61}$(s) in the number of xe21 may include the π electron-depleted nitrogen-containing ring.

In one embodiment, $Ar_{601}$ in Formula 601 may be selected from:

a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, and an azacarbazole group; and a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, and an azacarbazole group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si($Q_{31}$)($Q_{32}$)($Q_{33}$), —S(═O)$_2$($Q_{31}$), and —P(═O)($Q_{31}$)($Q_{32}$), and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

When xe11 in Formula 601 is 2 or more, two or more $Ar_{601}$(s) may be linked via a single bond.

In one or more embodiments, $Ar_{601}$ in Formula 601 may be an anthracene group.

In one or more embodiments, a compound represented by Formula 601 may be represented by Formula 601-1 below:

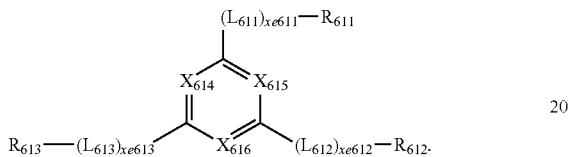

Formula 601-1

In Formula 601-1, $X_{614}$ may be N or C($R_{614}$), $X_{615}$ may be N or C($R_{615}$), $X_{616}$ may be N or C($R_{616}$), and at least one selected from $X_{614}$ to $X_{616}$ may be N, $L_{611}$ to $L_{613}$ may each independently be the same as described in connection with $L_{601}$, xe611 to xe613 may each independently be defined the same as xe1, $R_{611}$ to $R_{613}$ may each independently be the same as described in connection with $R_{601}$, and $R_{614}$ to $R_{616}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In one embodiment, $L_{601}$ and $L_{611}$ to $L_{613}$ in Formulae 601 and 601-1 may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, but embodiments of the present disclosure are not limited thereto.

In one or more embodiments, xe1 and xe611 to xe613 in Formulae 601 and 601-1 may each independently be 0, 1, or 2.

In one or more embodiments, $R_{601}$ and $R_{611}$ to $R_{613}$ in Formula 601 and 601-1 may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group;

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and —S(=O)$_2$(Q$_{601}$) and —P(=O)(Q$_{601}$)(Q$_{602}$), and Q$_{601}$ and Q$_{602}$ may be the same as described herein above.

The electron transport region may include at least one compound selected from Compounds ET1 to ET36, but embodiments of the present disclosure are not limited thereto:

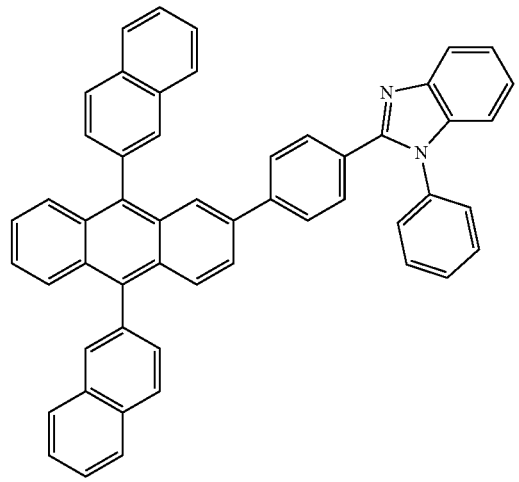

ET1

ET2
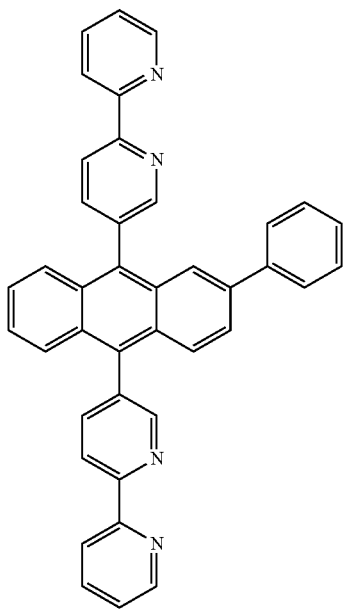
ET3
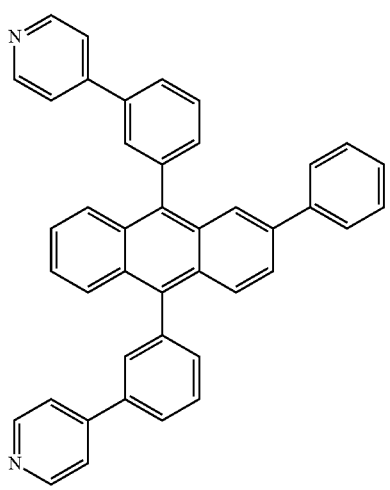
ET4
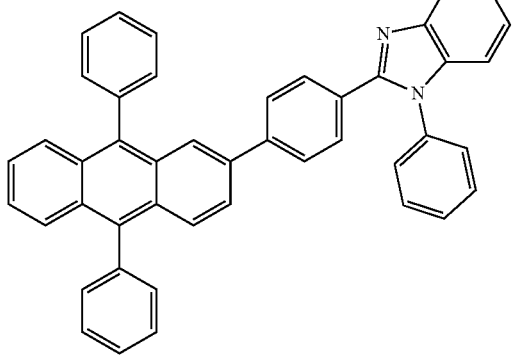
ET5
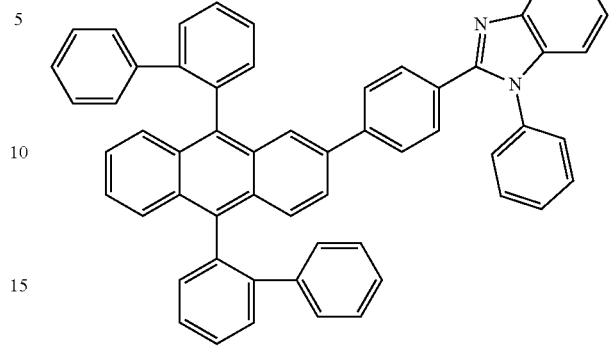
ET6
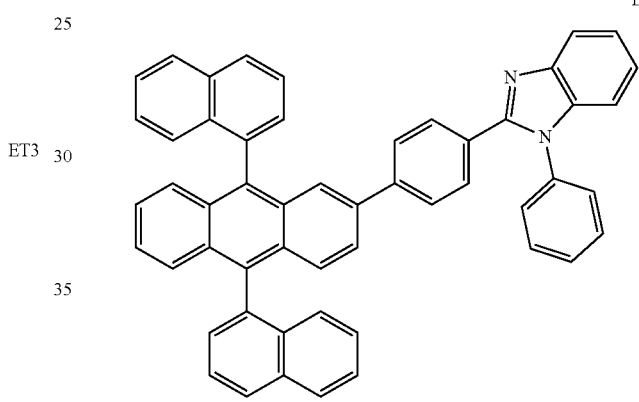
ET7
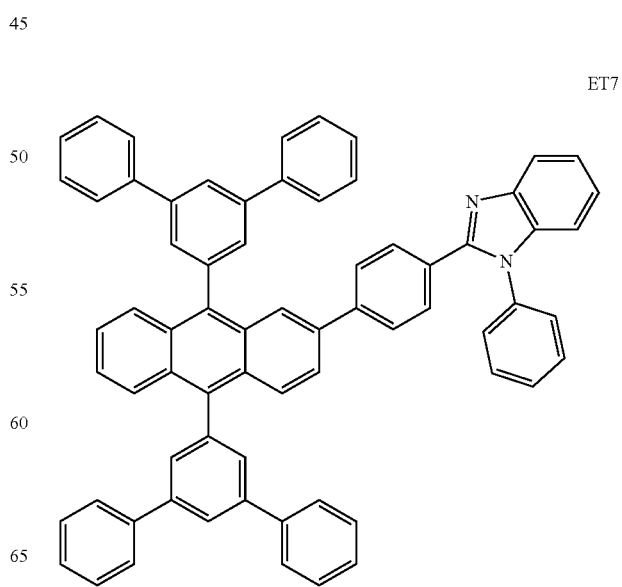

ET8
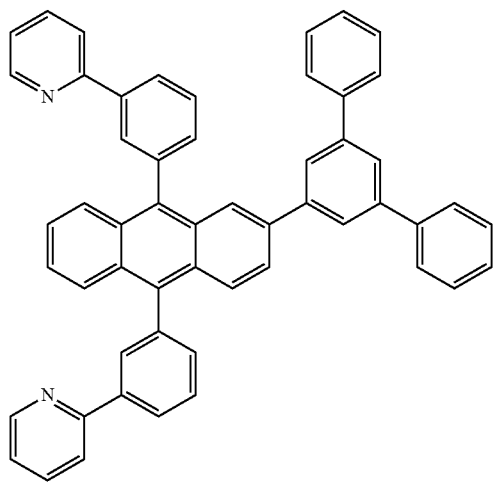
ET10
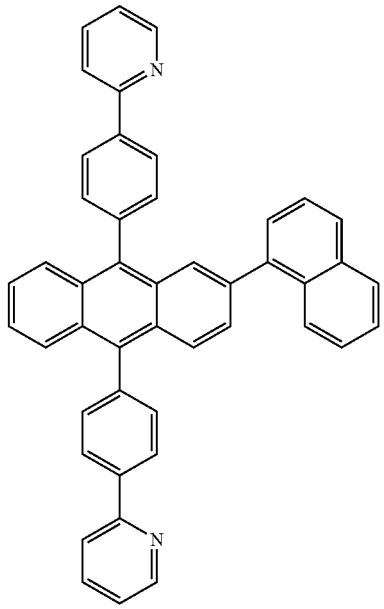
ET11
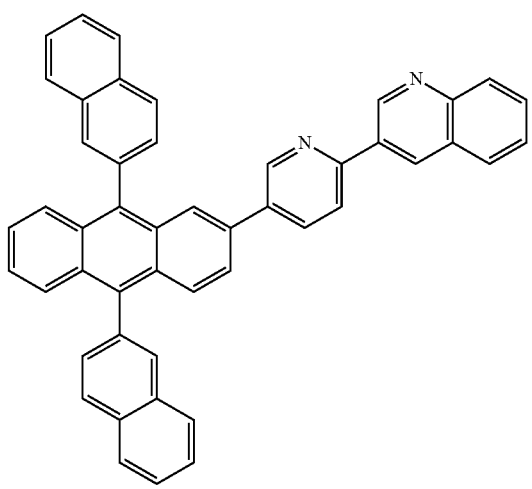
ET9
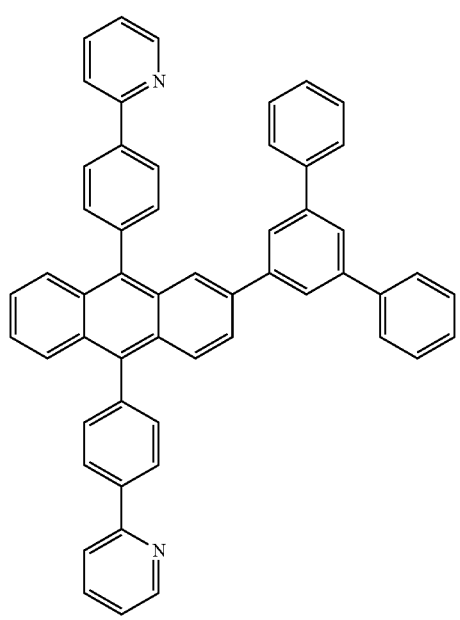
ET12
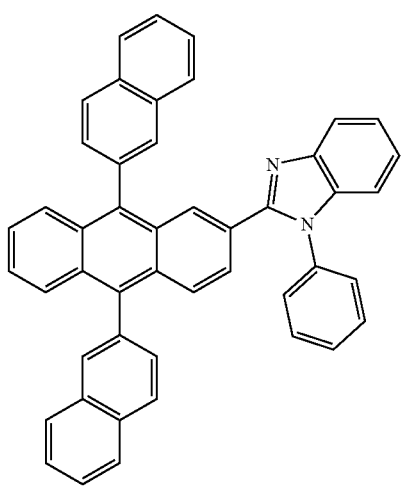

ET13
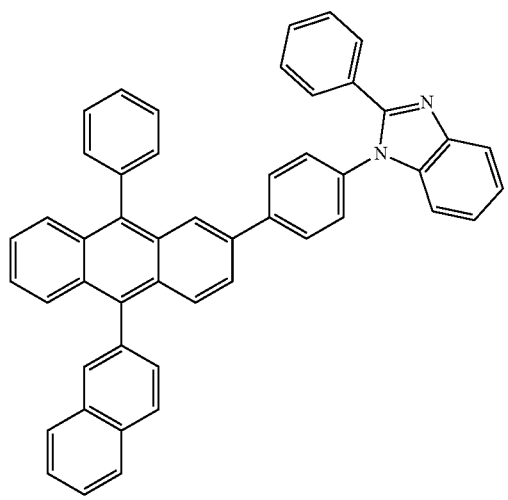
ET14
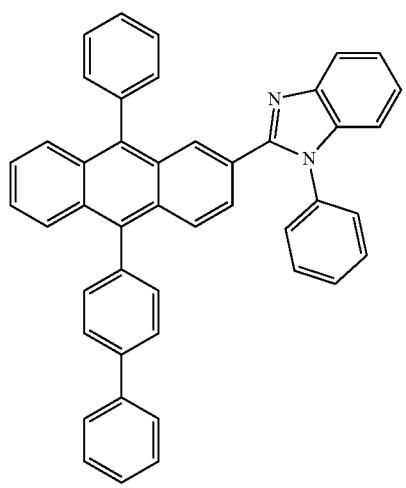
ET15
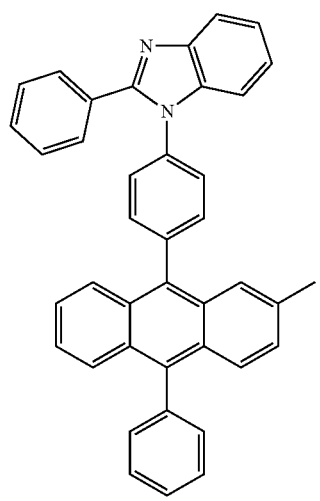
ET16
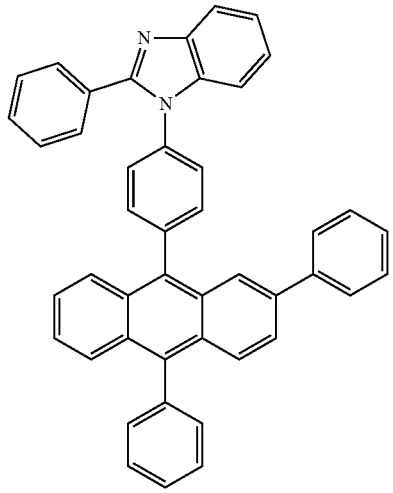
ET17
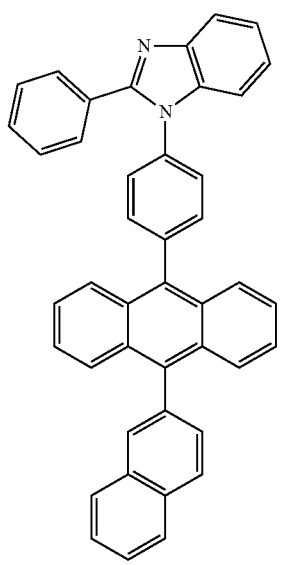
ET18
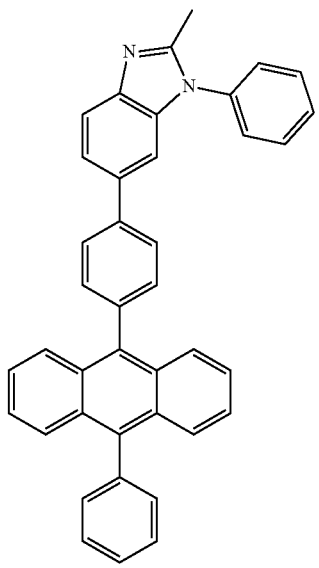

ET19
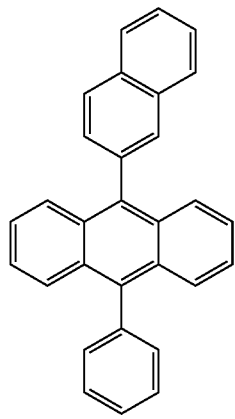
ET22
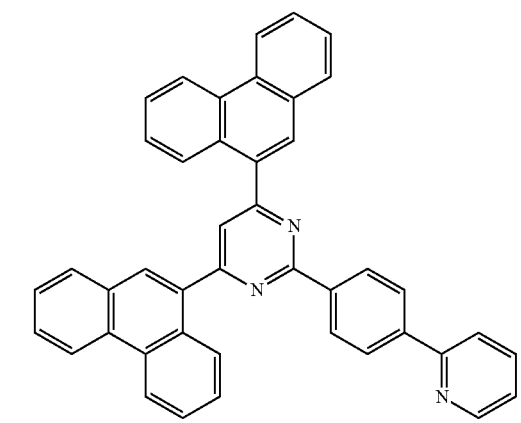
ET20
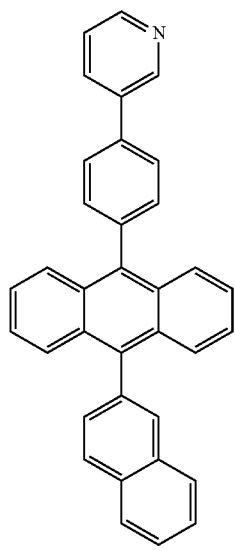
ET23
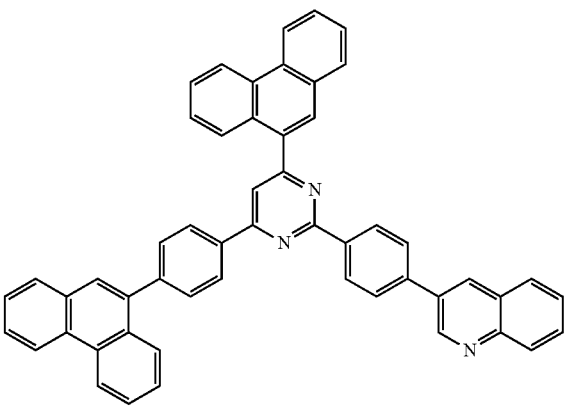
ET21
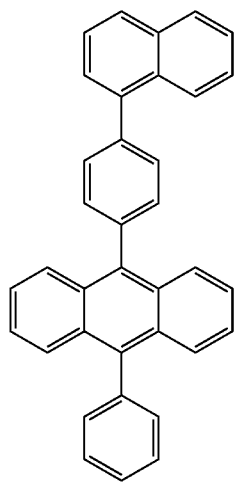
ET24
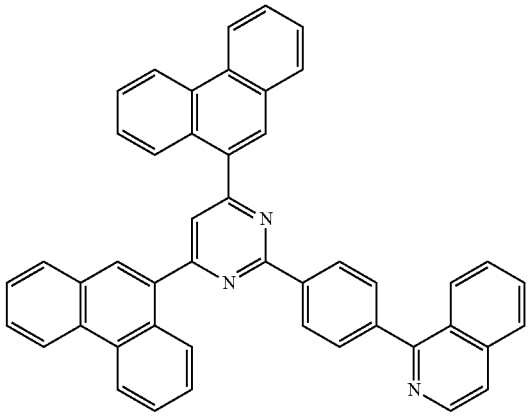

ET25
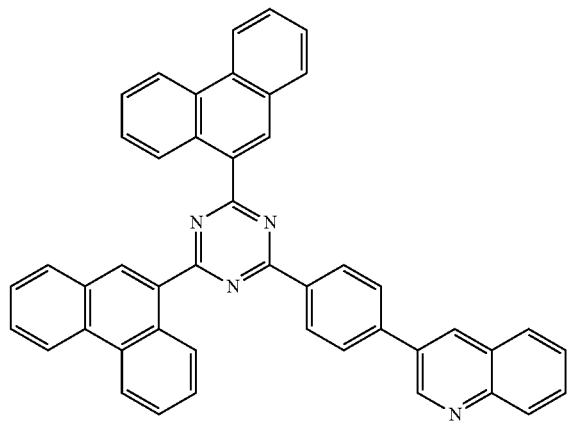
ET26
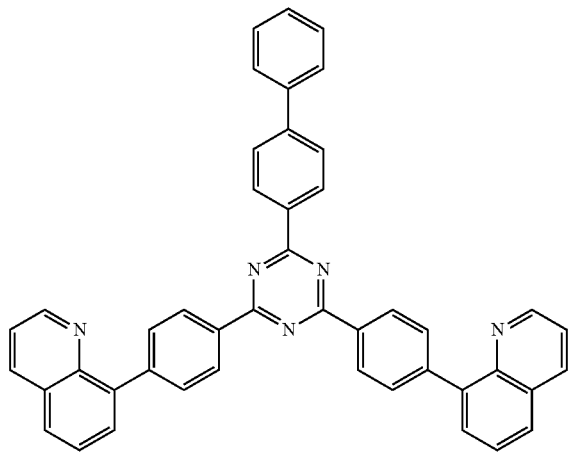
ET27
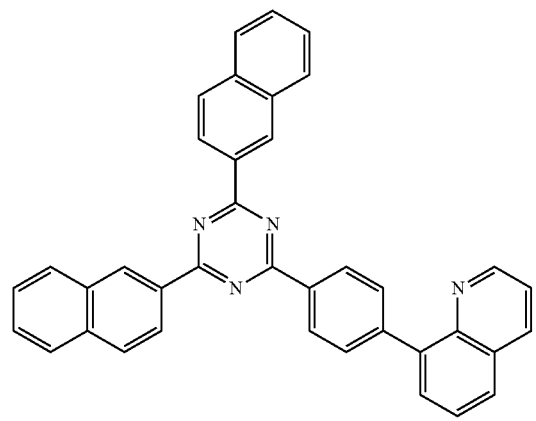
ET28
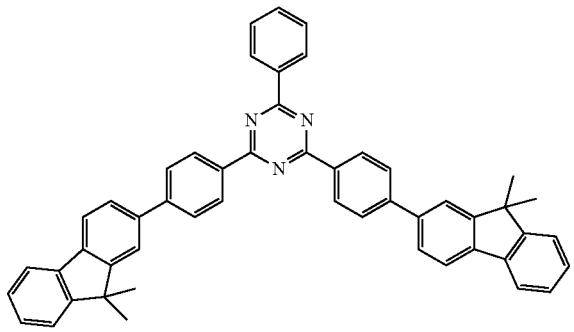
ET29
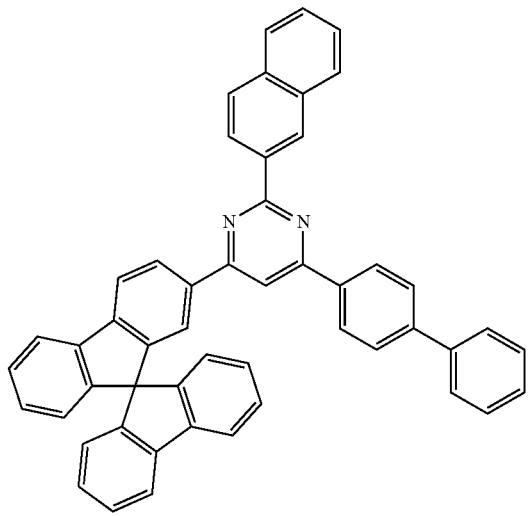
ET30
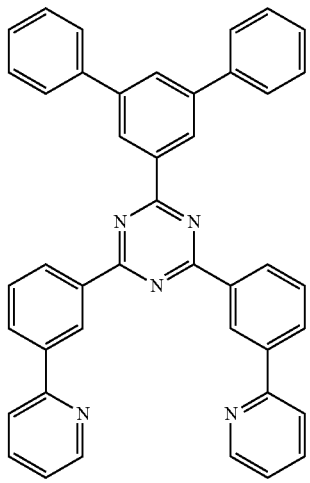

ET31
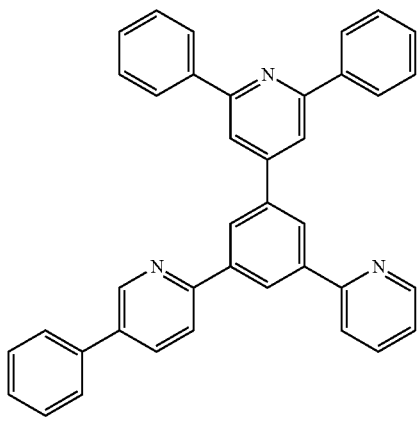
ET34
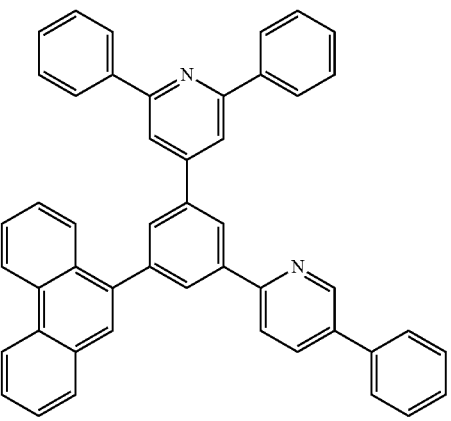
ET32
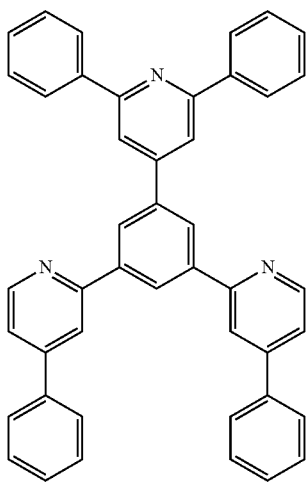
ET35
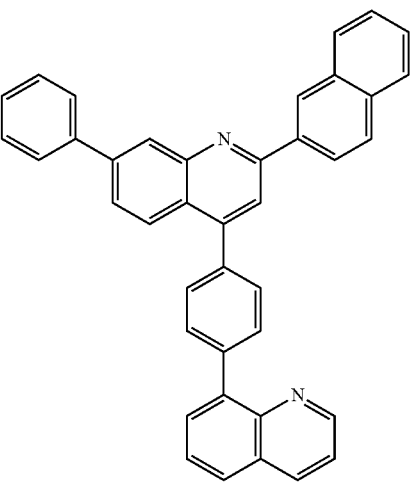
ET33
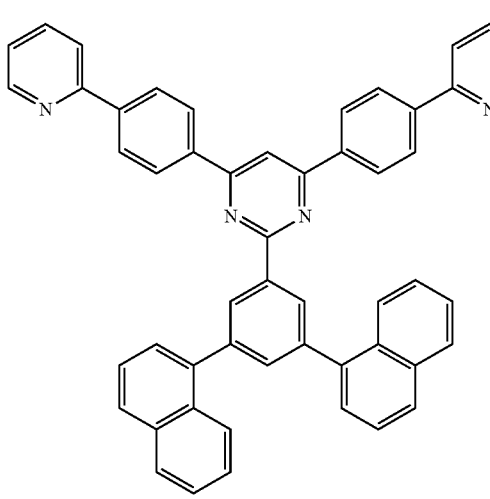
ET36
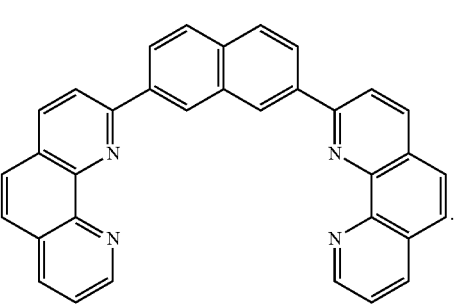
In one or more embodiments, the electron transport region may include at least one selected from 2,9-dimethyl-4,7-diphenyl-1, 10-phenanthroline (BCP), 4,7-diphenyl-1, 10-phenanthroline (Bphen), Alq3, BAlq, 3-(biphenyl-4-yl)-5-(4-tert-butylphenyl)-4-phenyl-4H-1,2,4-triazole (TAZ), and NTAZ:

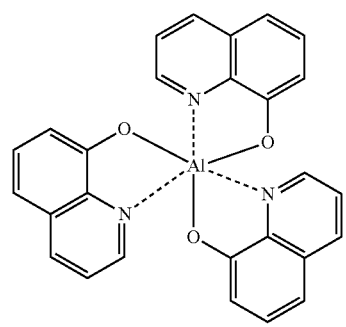

Alq₃

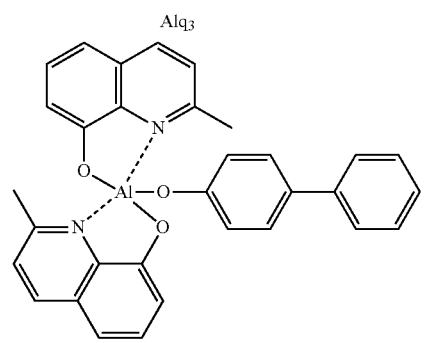

BAlq

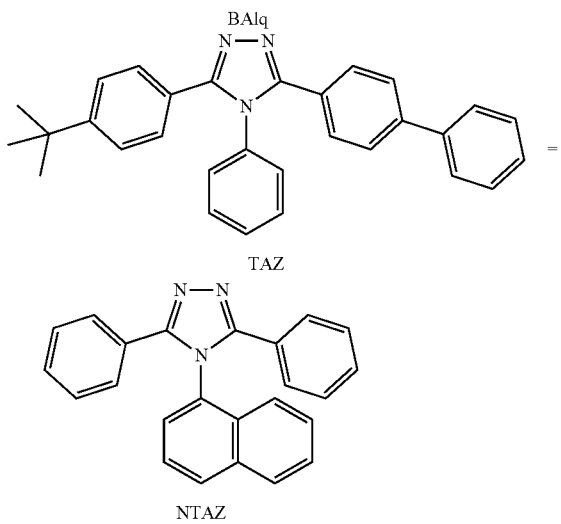

TAZ

NTAZ

In one embodiment, the electron transport region may include a phosphine oxide-containing compound (for example, TSPO1 used in the following examples or the like), but embodiments of the present disclosure are not limited thereto. In one embodiment, the phosphine oxide-containing compound may be used in a hole blocking layer in the electron transport region, but embodiments of the present disclosure are not limited thereto.

Thicknesses of the buffer layer, the hole blocking layer, and the electron control layer may each be in a range of about 20 Å to about 1,000 Å, for example, about 30 Å to about 300 Å. When the thicknesses of the buffer layer, the hole blocking layer, and the electron control layer are within these ranges, the electron blocking layer may have excellent electron blocking characteristics or electron control characteristics without a substantial increase in driving voltage.

A thickness of the electron transport layer may be in a range of about 100 Å to about 1,000 Å, for example, about 150 Å to about 500 Å. When the thickness of the electron transport layer is within the range described herein above, the electron transport layer may have suitable or satisfactory electron transport characteristics without a substantial increase in driving voltage.

The electron transport region (for example, the electron transport layer in the electron transport region) may further include, in addition to the materials described herein above, a metal-containing material.

The metal-containing material may include at least one selected from alkali metal complex and alkaline earth-metal complex. The alkali metal complex may include a metal ion selected from a Li ion, a Na ion, a K ion, a Rb ion, and a Cs ion, and the alkaline earth-metal complex may include a metal ion selected from a Be ion, a Mg ion, a Ca ion, a Sr ion, and a Ba ion. A ligand coordinated with the metal ion of the alkali metal complex or the alkaline earth-metal complex may be selected from a hydroxy quinoline, a hydroxy isoquinoline, a hydroxy benzoquinoline, a hydroxy acridine, a hydroxy phenanthridine, a hydroxy phenyloxazole, a hydroxy phenylthiazole, a hydroxy phenyloxadiazole, a hydroxy phenylthiadiazole, a hydroxy phenylpyridine, a hydroxy phenylbenzimidazole, a hydroxy phenylbenzothiazole, a bipyridine, a phenanthroline, and a cyclopentadiene, but embodiments of the present disclosure are not limited thereto.

For example, the metal-containing material may include a Li complex. The Li complex may include, for example, Compound ET-D1 (lithium quinolate, LiQ) or ET-D2:

ET-D1

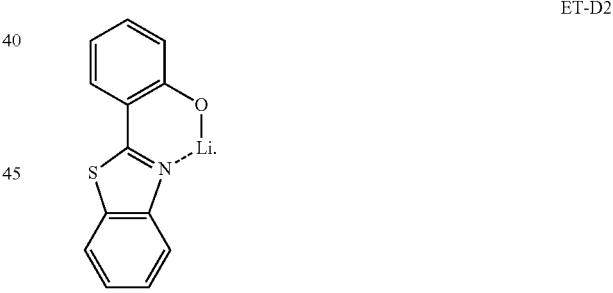

ET-D2

The electron transport region may include an electron injection layer that facilitates electron injection from the second electrode 190. The electron injection layer may directly contact the second electrode 190.

The electron injection layer may have i) a single-layered structure including a single layer including a single material, ii) a single-layered structure including a single layer including a plurality of different materials, or iii) a multi-layered structure having a plurality of layers including a plurality of different materials.

The electron injection layer may include an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combinations thereof.

The alkali metal may be selected from Li, Na, K, Rb, and Cs. In one embodiment, the alkali metal may be Li, Na, or Cs. In one or more embodiments, the alkali metal may be Li or Cs, but embodiments of the present disclosure are not limited thereto.

The alkaline earth metal may be selected from Mg, Ca, Sr, and Ba.

The rare earth metal may be selected from Sc, Y, Ce, Tb, Yb, and Gd.

The alkali metal compound, the alkaline earth-metal compound, and the rare earth metal compound may be selected from oxides and halides (for example, fluorides, chlorides, bromides, or iodides) of the alkali metal, the alkaline earth-metal, and the rare earth metal.

The alkali metal compound may be selected from alkali metal oxides, such as $Li_2$, $Cs_2O$, or $K_2O$, and alkali metal halides, such as LiF, NaF, CsF, KF, LiI, NaI, CsI, or KI. In one embodiment, the alkali metal compound may be selected from LiF, $Li_2$, NaF, LiI, NaI, CsI, and KI, but embodiments of the present disclosure are not limited thereto.

The alkaline earth-metal compound may be selected from alkaline earth-metal oxides, such as BaO, SrO, CaO, $Ba_xSr_{1-x}O$ (0<x<1), or $Ba_xCa_{1-x}O$ (0<x<1). In one embodiment, the alkaline earth-metal compound may be selected from BaO, SrO, and CaO, but embodiments of the present disclosure are not limited thereto.

The rare earth metal compound may be selected from $YbF_3$, $ScF_3$, $Sc_2O_3$, $Y_2O_3$, $Ce_2O_3$, $GdF_3$, and $TbF_3$. In one embodiment, the rare earth metal compound may be selected from $YbF_3$, $ScF_3$, $TbF_3$, $YbI_3$, $ScI_3$, and $TbI_3$, but embodiments of the present disclosure are not limited thereto.

The alkali metal complex, the alkaline earth-metal complex, and the rare earth metal complex may include an ion of alkali metal, alkaline earth-metal, and rare earth metal as described herein above, and a ligand coordinated with a metal ion of the alkali metal complex, the alkaline earth-metal complex, or the rare earth metal complex may be selected from hydroxy quinoline, hydroxy isoquinoline, hydroxy benzoquinoline, hydroxy acridine, hydroxy phenanthridine, hydroxy phenyloxazole, hydroxy phenylthiazole, hydroxy diphenyloxadiazole, hydroxy diphenylthiadiazole, hydroxy phenylpyridine, hydroxy phenylbenzimidazole, hydroxy phenylbenzothiazole, bipyridine, phenanthroline, and cyclopentadiene, but embodiments of the present disclosure are not limited thereto.

The electron injection layer may include (or consist of) an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combinations thereof, as described herein above. In one or more embodiments, the electron injection layer may further include an organic material. When the electron injection layer further includes an organic material, an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combinations thereof may be homogeneously or non-homogeneously dispersed in a matrix including the organic material.

A thickness of the electron injection layer may be in a range of about 1 Å to about 100 Å, for example, about 3 Å to about 90 Å. When the thickness of the electron injection layer is within the range described herein above, the electron injection layer may have suitable or satisfactory electron injection characteristics without a substantial increase in driving voltage.

Second Electrode 190

The second electrode 190 may be on the organic layer 150 having such a structure. The second electrode 190 may be a cathode which is an electron injection electrode, and in this regard, a material for forming the second electrode 190 may be selected from metal, an alloy, an electrically conductive compound, and a combination thereof, which have a relatively low work function.

The second electrode 190 may include at least one selected from lithium (Li), silver (Ag), magnesium (Mg), aluminum (Al), aluminum-lithium (Al—Li), calcium (Ca), magnesium-indium (Mg—In), magnesium-silver (Mg—Ag), ITO, and IZO, but embodiments of the present disclosure are not limited thereto. The second electrode 190 may be a transmissive electrode, a semi-transmissive electrode, or a reflective electrode.

The second electrode 190 may have a single-layered structure, or a multi-layered structure including two or more layers.

Figures 3, 4:
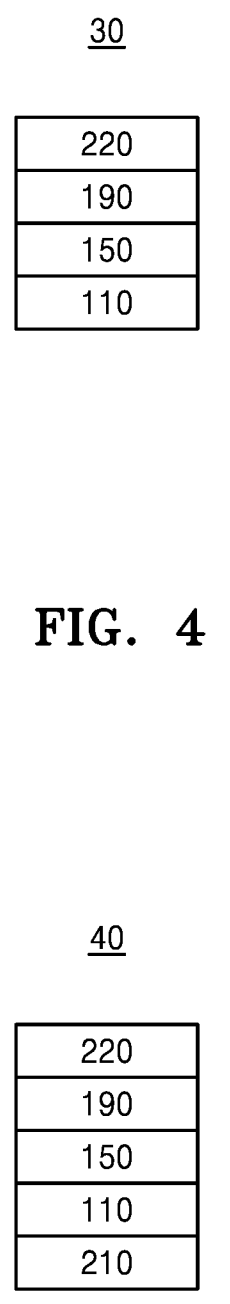

Description of FIGS. 2 to 4

FIG. 2 is a schematic view of an organic light-emitting device 20 according to an embodiment. The organic light-emitting device 20 includes a first capping layer 210, the first electrode 110, the organic layer 150, and the second electrode 190, which are sequentially stacked in this stated order. FIG. 3 is a schematic view of an organic light-emitting device 30 according to an embodiment. The organic light-emitting device 30 includes the first electrode 110, the organic layer 150, the second electrode 190, and a second capping layer 220, which are sequentially stacked in this stated order. FIG. 4 is a schematic view of an organic light-emitting device 40 according to an embodiment. The organic light-emitting device 40 includes the first capping layer 210, the first electrode 110, the organic layer 150, the second electrode 190, and the second capping layer 220, which are sequentially stacked in this stated order.

Regarding FIGS. 2 to 4, the first electrode 110, the organic layer 150, and the second electrode 190 may be understood by referring to the description presented in connection with FIG. 1.

In the organic layer 150 of each of the organic light-emitting devices 20 and 40, light generated in an emission layer may pass through the first electrode 110 and the first capping layer 210 toward the outside, wherein the first electrode 110 may be a semi-transmissive electrode or a transmissive electrode. In the organic layer 150 of each of the organic light-emitting devices 30 and 40, light generated in an emission layer may pass through the second electrode 190 and the second capping layer 220 toward the outside, wherein the second electrode 190 may be a semi-transmissive electrode or a transmissive electrode.

The first capping layer 210 and the second capping layer 220 may increase external luminescence efficiency according to the principle of constructive interference.

The first capping layer 210 and the second capping layer 220 may each independently be an organic capping layer including an organic material, an inorganic capping layer including an inorganic material, or a composite capping layer including an organic material and an inorganic material. The organic capping layer may include polyethylene terephthalate, polyethylene naphthalate, polycarbonate, polyimide, polyethylene sulfonate, polyoxymethylene, polyarylate, hexamethyldisiloxane, acryl-based resin (e.g., polymethylmethacrylate, polyacrylic acid, etc.), or any combination thereof.

At least one selected from the first capping layer 210 and the second capping layer 220 may each independently include at least one material selected from carbocyclic compounds, heterocyclic compounds, amine-based compounds, porphyrine derivatives, phthalocyanine derivatives, a naphthalocyanine derivatives, alkali metal complexes, and alkaline earth-based complexes. The carbocyclic compound, the heterocyclic compound, and the amine-based compound may be optionally substituted with a substituent containing at least one element selected from O, N, S, Se, Si, F, Cl, Br, and I.

In one embodiment, at least one selected from the first capping layer 210 and the second capping layer 220 may each independently include an amine-based compound.

In one embodiment, at least one selected from the first capping layer 210 and the second capping layer 220 may each independently include the compound represented by Formula 201 or the compound represented by Formula 202.

In one or more embodiments, at least one selected from the first capping layer 210 and the second capping layer 220 may each independently include a compound selected from Compounds HT28 to HT33 and Compounds CP1 to CP5, but embodiments of the present disclosure are not limited thereto:

HT28

HT29

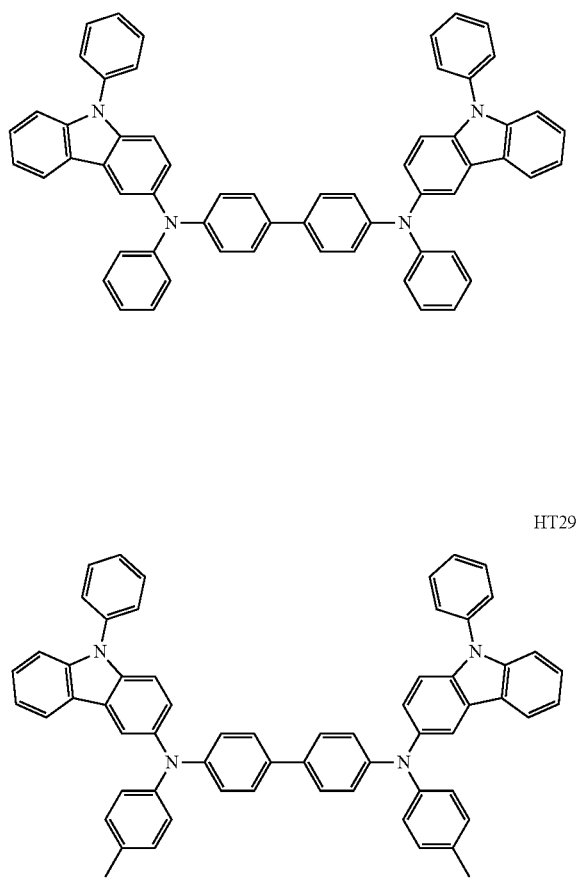

HT30

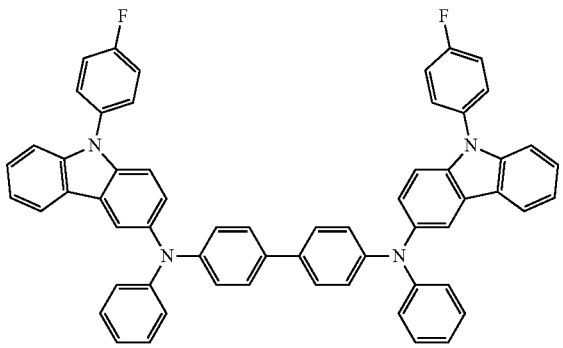

HT31

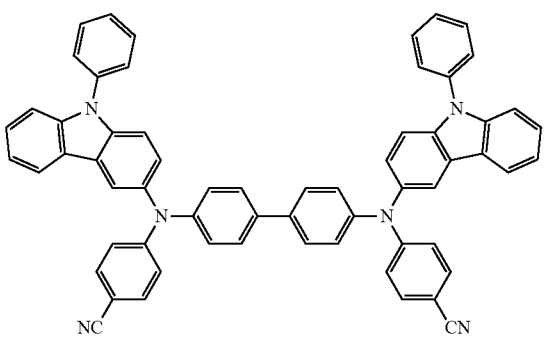

HT32

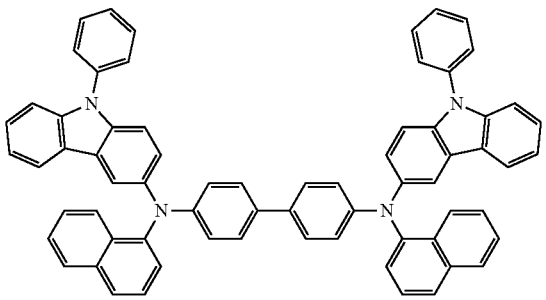

HT33

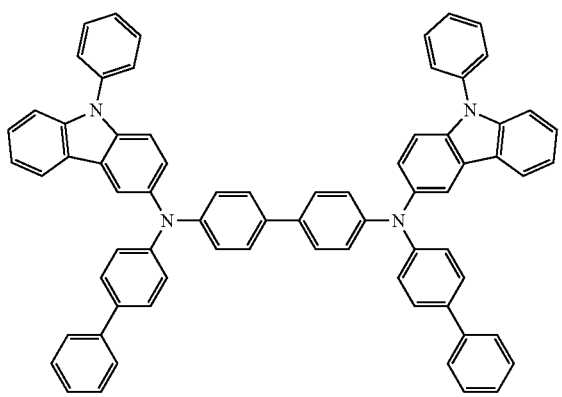

-continued

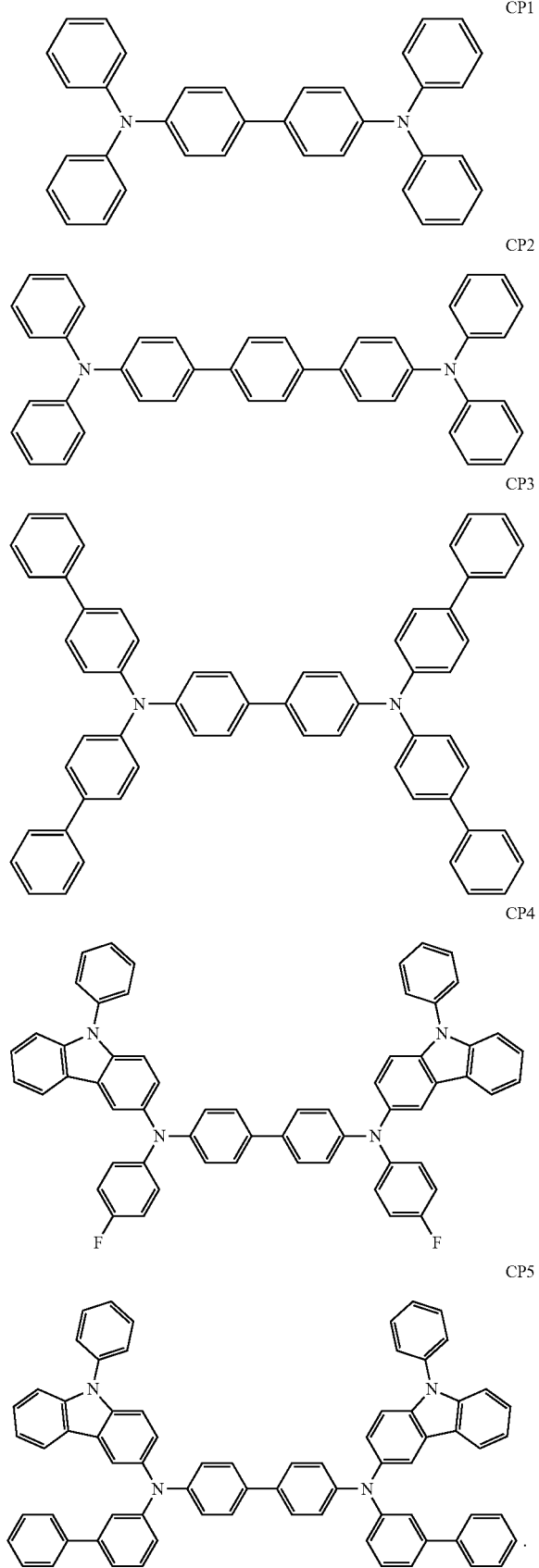

CP1

CP2

CP3

CP4

CP5

Hereinbefore, the organic light-emitting device according to an embodiment has been described in connection with FIGS. 1 to 4, but embodiments of the present disclosure are not limited thereto.

Layers constituting the hole transport region, an emission layer, and layers constituting the electron transport region may be formed in a certain region by using one or more suitable methods selected from vacuum deposition, spin coating, casting, Langmuir-Blodgett (LB) deposition, ink-jet printing, laser-printing, and laser-induced thermal imaging.

When layers constituting the hole transport region, an emission layer, and layers constituting the electron transport region are formed by vacuum deposition, the deposition may be performed at a deposition temperature of about 100° C. to about 500° C., a vacuum degree of about $10^{-8}$ torr to about $10^{-3}$ torr, and a deposition speed of about 0.01 Å/sec to about 100 Å/sec by taking into account a material to be included in a layer to be formed, and the structure of a layer to be formed.

When layers constituting the hole transport region, an emission layer, and layers constituting the electron transport region are formed by spin coating, the spin coating may be performed at a coating speed of about 2,000 rpm to about 5,000 rpm and at a heat treatment temperature of about 80° C. to 200° C. by taking into account a material to be included in a layer to be formed, and the structure of a layer to be formed.

Apparatus

The organic light-emitting device may be included in various suitable apparatuses. For example, a light-emitting apparatus, an authentication apparatus, or an electronic apparatus, which includes the organic light-emitting device, may be provided.

The light-emitting apparatus may further include, in addition to the organic light-emitting device, a thin film transistor including a source electrode and a drain electrode. One of the source electrode and the drain electrode of the thin film transistor may be in electrical contact with one of the first electrode and the second electrode of the organic light-emitting device. The light-emitting apparatus may be used as various suitable displays, light sources, and/or the like.

The authentication apparatus may be, for example, a biometric authentication apparatus for authenticating an individual by using biometric information of a biometric body (for example, a fingertip, a pupil, and/or the like).

The authentication apparatus may further include, in addition to the organic light-emitting device, a biometric information collector.

The electronic apparatus may be applied to personal computers (for example, a mobile personal computer), mobile phones, digital cameras, electronic organizers, electronic dictionaries, electronic game machines, medical instruments (for example, electronic thermometers, sphygmomanometers, blood glucose meters, pulse measurement devices, pulse wave measurement devices, electrocardiogram (ECG) displays, ultrasonic diagnostic devices, and/or endoscope displays), fish finders, various suitable measuring instruments, meters (for example, meters for a vehicle, an aircraft, and a vessel), projectors, and/or the like, but embodiments of the present disclosure are not limited thereto.

General Definition of at Least Some of the Substituents

The term "$C_1$-$C_{60}$ alkyl group," as used herein, refers to a linear or branched aliphatic saturated hydrocarbon monovalent group having 1 to 60 carbon atoms, and examples thereof include a methyl group, an ethyl group, a propyl group, an isobutyl group, a sec-butyl group, a tert-butyl group, a pentyl group, an isoamyl group, and a hexyl group. The term "$C_1$-$C_{60}$ alkylene group," as used herein, refers to a divalent group having substantially the same structure as the $C_1$-$C_{60}$ alkyl group.

The term "$C_2$-$C_{60}$ alkenyl group," as used herein, refers to a hydrocarbon group having at least one carbon-carbon double bond at a main chain (e.g., in the middle) or at a terminal end (e.g., the terminus) of the $C_2$-$C_{60}$ alkyl group, and examples thereof include an ethenyl group, a propenyl group, and a butenyl group. The term "$C_2$-$C_{60}$ alkenylene group," as used herein, refers to a divalent group having substantially the same structure as the $C_2$-$C_{60}$ alkenyl group.

The term "$C_2$-$C_{60}$ alkynyl group," as used herein, refers to a hydrocarbon group having at least one carbon-carbon triple bond at a main chain (e.g., in the middle) or at a terminal end (e.g., the terminus) of the $C_2$-$C_{60}$ alkyl group, and examples thereof include an ethynyl group, and a propynyl group. The term "$C_2$-$C_{60}$ alkynylene group," as used herein, refers to a divalent group having substantially the same structure as the $C_2$-$C_{60}$ alkynyl group.

The term "$C_1$-$C_{60}$ alkoxy group," as used herein, refers to a monovalent group represented by —$OA_{101}$ (wherein $A_{101}$ is the $C_1$-$C_{60}$ alkyl group), and examples thereof include a methoxy group, an ethoxy group, and an isopropyloxy group.

The term "$C_3$-$C_{10}$ cycloalkyl group," as used herein, refers to a monovalent saturated hydrocarbon monocyclic group having 3 to 10 carbon atoms, and examples thereof include a cyclopropyl group, a cyclobutyl group, a cyclopentyl group, a cyclohexyl group, and a cycloheptyl group. The term "$C_3$-$C_{10}$ cycloalkylene group," as used herein, refers to a divalent group having substantially the same structure as the $C_3$-$C_{10}$ cycloalkyl group.

The term "$C_1$-$C_{10}$ heterocycloalkyl group," as used herein, refers to a monovalent monocyclic group having at least one heteroatom selected from N, O, Si, P, and S as a ring-forming atom and 1 to 10 carbon atoms, and examples thereof include a 1,2,3,4-oxatriazolidinyl group, a tetrahydrofuranyl group, and a tetrahydrothiophenyl group. The term "$C_1$-$C_{10}$ heterocycloalkylene group," as used herein, refers to a divalent group having substantially the same structure as the $C_1$-$C_{10}$ heterocycloalkyl group.

The term "$C_3$-$C_{10}$ cycloalkenyl group," as used herein, refers to a monovalent monocyclic group that has 3 to 10 carbon atoms and at least one carbon-carbon double bond in the ring thereof and no aromaticity (e.g., is not aromatic), and examples thereof include a cyclopentenyl group, a cyclohexenyl group, and a cycloheptenyl group. The term "$C_3$-$C_{10}$ cycloalkenylene group," as used herein, refers to a divalent group having substantially the same structure as the $C_3$-$C_{10}$ cycloalkenyl group.

The term "$C_1$-$C_{10}$ heterocycloalkenyl group," as used herein, refers to a monovalent monocyclic group that has at least one heteroatom selected from N, O, Si, P, and S as a ring-forming atom, 1 to 10 carbon atoms, and at least one carbon-carbon double bond in its ring. Non-limiting examples of the $C_1$-$C_{10}$ heterocycloalkenyl group include a 4,5-dihydro-1,2,3,4-oxatriazolyl group, a 2,3-dihydrofuranyl group, and a 2,3-dihydrothiophenyl group. The term "$C_1$-$C_{10}$ heterocycloalkenylene group," as used herein, refers to a divalent group having substantially the same structure as the $C_1$-$C_{10}$ heterocycloalkenyl group.

The term "$C_6$-$C_{60}$ aryl group," as used herein, refers to a monovalent group having a carbocyclic aromatic system having 6 to 60 carbon atoms, and the term "$C_6$-$C_{60}$ arylene group," as used herein, refers to a divalent group having a carbocyclic aromatic system having 6 to 60 carbon atoms. Non-limiting examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other (e.g., combined together).

The term "$C_1$-$C_{60}$ heteroaryl group," as used herein, refers to a monovalent group having a carbocyclic aromatic system that has at least one heteroatom selected from N, O, Si, P, and S as a ring-forming atom, in addition to 1 to 60 carbon atoms. The term "$C_1$-$C_{60}$ heteroarylene group," as used herein, refers to a divalent group having a carbocyclic aromatic system that has at least one heteroatom selected from N, O, Si, P, and S as a ring-forming atom, in addition to 1 to 60 carbon atoms. Non-limiting examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be condensed with each other (e.g., combined together).

The term "$C_6$-$C_{60}$ aryloxy group," as used herein, refers to —$OA_{102}$ (wherein $A_{102}$ is the $C_6$-$C_{60}$ aryl group), and the term "$C_6$-$C_{60}$ arylthio group," as used herein, indicates —$SA_{103}$ (wherein $A_{103}$ is the $C_6$-$C_{60}$ aryl group).

The term "monovalent non-aromatic condensed polycyclic group," as used herein, refers to a monovalent group (for example, having 8 to 60 carbon atoms) having two or more rings condensed with each other (e.g., combined together), only carbon atoms as ring-forming atoms, and no aromaticity in its entire molecular structure (e.g., is not aromatic). An example of the monovalent non-aromatic condensed polycyclic group is a fluorenyl group. The term "divalent non-aromatic condensed polycyclic group," as used herein, refers to a divalent group having substantially the same structure as the monovalent non-aromatic condensed polycyclic group.

The term "monovalent non-aromatic condensed heteropolycyclic group," as used herein, refers to a monovalent group (for example, having 1 to 60 carbon atoms) having two or more rings condensed to each other (e.g., combined together), at least one heteroatom selected from N, O, Si, P, and S, other than carbon atoms, as a ring-forming atom, and no aromaticity in its entire molecular structure (e.g., is not aromatic). An example of the monovalent non-aromatic condensed heteropolycyclic group is a carbazolyl group. The term "divalent non-aromatic condensed heteropolycyclic group," as used herein, refers to a divalent group having substantially the same structure as the monovalent non-aromatic condensed heteropolycyclic group.

The term "$C_4$-$C_{60}$ carbocyclic group," as used herein, refers to a monocyclic or polycyclic group having 4 to 60 carbon atoms in which a ring-forming atom is a carbon atom only. The term "$C_4$-$C_{60}$ carbocyclic group," as used herein, refers to an aromatic carbocyclic group or a non-aromatic carbocyclic group. The $C_4$-$C_{60}$ carbocyclic group may be a ring, such as benzene, a monovalent group, such as a phenyl group, or a divalent group, such as a phenylene group. In one or more embodiments, depending on the number of substituents connected to the $C_4$-$C_{60}$ carbocyclic group, the $C_4$-$C_{60}$ carbocyclic group may be a trivalent group or a quadrivalent group.

The term "$C_1$-$C_{60}$ heterocyclic group," as used herein, refers to a group having substantially the same structure as the $C_4$-$C_{60}$ carbocyclic group, except that as a ring-forming atom, at least one heteroatom selected from N, O, Si, P, and S is used in addition to carbon (the number of carbon atoms may be in a range of 1 to 60).

In the present specification, at least one substituent of the substituted $C_4$-$C_{60}$ carbocyclic group, the substituted $C_1$-$C_{60}$ heterocyclic group, the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

- deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;
- a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);
- a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;
- a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and
- —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and
- $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a $C_1$-$C_{60}$ alkyl group substituted with at least one selected from deuterium, —F, and a cyano group, a $C_6$-$C_{60}$ aryl group substituted with at least one selected from deuterium, —F, and a cyano group, a biphenyl group, and a terphenylgroup.

The term "Ph," as used herein, refers to a phenyl group, the term "Me," as used herein, refers to a methyl group, the term "Et," as used herein, refers to an ethyl group, the term "ter-Bu" or "Bu$^t$," as used herein, refers to a tert-butyl group, and the term "OMe," as used herein, refers to a methoxy group.

The term "biphenyl group," as used herein, refers to "a phenyl group substituted with a phenyl group". In other words, the "biphenyl group" is a substituted phenyl group having a $C_6$-$C_{60}$ aryl group as a substituent.

The term "terphenyl group" as used herein refers to "a phenyl group substituted with a biphenyl group." In other words, the "terphenyl group" is a phenyl group having, as a substituent, a $C_6$-$C_{60}$ aryl group substituted with a $C_6$-$C_{60}$ aryl group.

* and *', as used herein, unless defined otherwise, each refer to a binding site to a neighboring atom in a corresponding formula.

Hereinafter, a compound according to embodiments and an organic light-emitting device according to embodiments will be described in more detail with reference to Synthesis Examples and Examples. The wording "B was used instead of A" used in describing Synthesis Examples refers to that an identical molar equivalent of B was used in place of A.

EXAMPLES

Synthesis Example: Synthesis of Compound

Synthesis of Compound 1-4

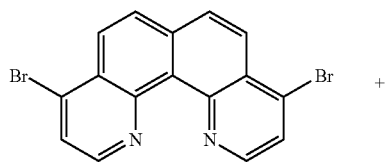
+
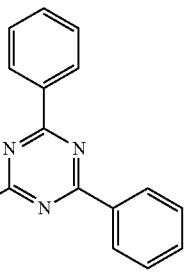

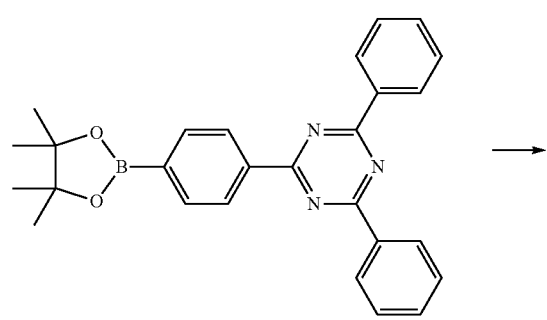

4,9-dibromoquinolino[7,8-h]quinoline (3.9 g, 10 mmol), 2,4-diphenyl-6-[4-(4, 4,5,5-tetramethyl-1,3,2-dioxaborolan-2-yl)phenyl]-s-triazine (5.0 g, 11 mmol), K₂CO₃ (2.8 g, 20 mmol), and Pd(PPh₃)₄ (0.41 g, 0.35 mmol) were added to a schlenk tube, dried in a vacuum state for 2 hours, and then dissolved in tetrahydrofuran (THF) (100 mL). N₂-purged anhydrous EtOH (20 mL) was added thereto and stirred at a temperature of 80° C. for 24 hours in a nitrogen atmosphere. The reaction mixture was cooled to room temperature, and a solvent was removed therefrom under reduced pressure. The resultant was washed by using an excess of dichloromethane (DCM) and distilled water, and an organic layer was separated therefrom. The separated organic layer was dried by using MgSO₄ and purified by column chromatography (DCM/hexane (1:1, v/v)) to obtain Intermediate 1-4-A (3.1 g, 5.0 mmol, yield: 50%).

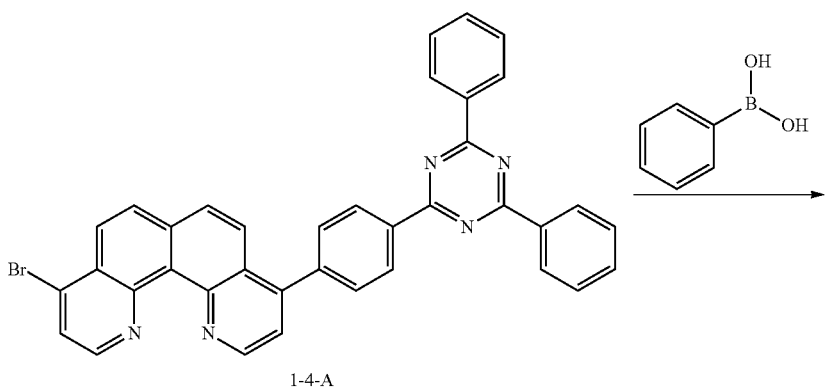

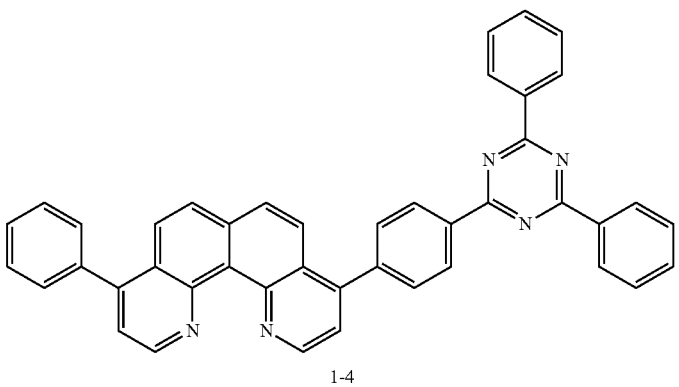

Intermediate 1-4-A (6.2 g, 10 mmol), phenylboronic acid (1.5 g, 12 mmol), K₂CO₃ (1.4 g, 10 mmol), and Pd(PPh₃)₄ (0.41 g, 0.35 mmol) were added to a schlenk tube, dried in a vacuum state for 2 hours, and then dissolved in dimethylformamide (DMF) (100 mL). N₂-purged anhydrous EtOH (20 mL) was added thereto and stirred at a temperature of 100° C. for 24 hours in a nitrogen atmosphere. The reaction mixture was cooled to room temperature, and a solvent was removed therefrom under reduced pressure. The resultant was washed by using an excess of DCM and distilled water, and an organic layer was separated therefrom. The separated organic layer was dried by using MgSO₄ and purified by column chromatography (DCM) to obtain Compound 1-4 (4.8 g, 7.8 mmol, yield: 78%).

Synthesis of Compound-2-3

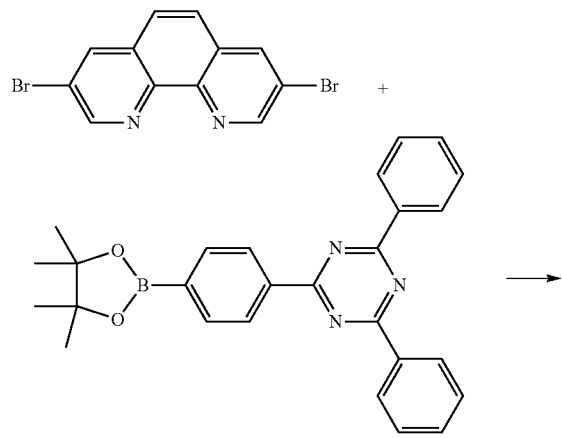

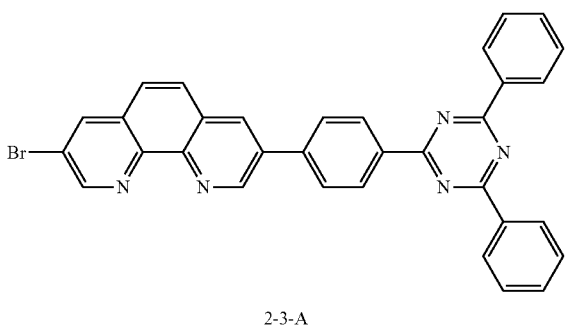

2-3-A 3.8-dibromo-1,10-phenanthroline (3.4 g, 10 mmol), 2,4-diphenyl-6-[4-(4,4,5, 5-tetramethyl-1,3,2-dioxaborolan-2-yl)phenyl]-s-triazine (5.0 g, 11 mmol), K₂CO₃ (2.8 g, 20 mmol), and Pd(PPh₃)₄ (0.41 g, 0.35 mmol) were added to a schlenk tube, dried in a vacuum state for 2 hours, and then dissolved in DMF (100 mL). N₂-purged anhydrous EtOH (20 mL) was added thereto and stirred at a temperature of 100° C. for 24 hours in a nitrogen atmosphere. The reaction mixture was cooled to room temperature, and a solvent was removed therefrom under reduced pressure. The resultant was washed by using an excess of DCM and distilled water, and an organic layer was separated therefrom. The separated organic layer was dried by using MgSO₄ and purified by column chromatography (DCM/hexane (10:1, v/v)) to obtain Intermediate 2-3-A (4.4 g, 7.7 mmol, yield: 77%).

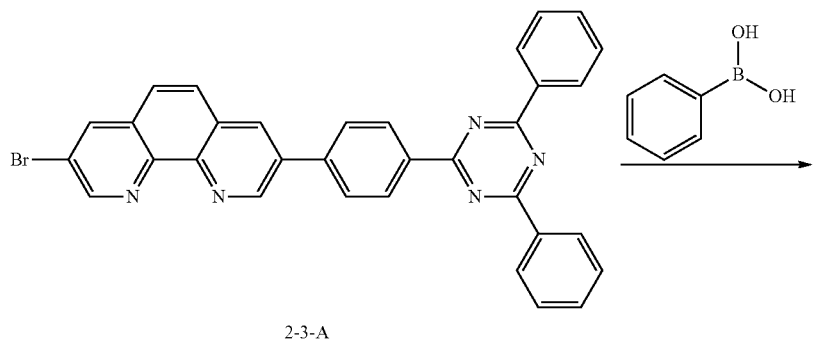

2-3-A

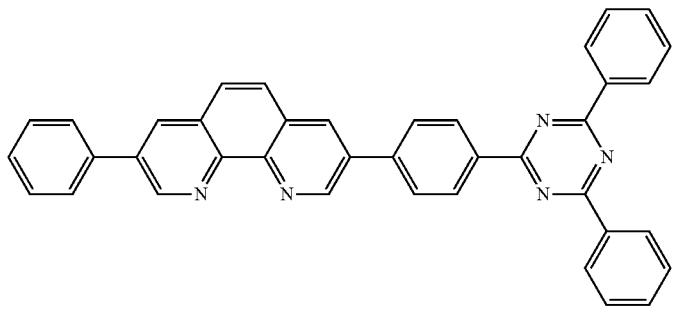

2-3

Intermediate 2-3-A (5.7 g, 10 mmol), phenylboronic acid (1.5 g, 12 mmol), K$_2$CO$_3$ (1.4 g, 10 mmol), and Pd(PPh$_3$)$_4$ (0.41 g, 0.35 mmol) were added to a schlenk tube, dried in a vacuum state for 2 hours, and then dissolved in THF (100 mL). N$_2$-purged anhydrous EtOH (20 mL) was added thereto and stirred at a temperature of 80° C. for 24 hours in a nitrogen atmosphere. The reaction mixture was cooled to room temperature, and a solvent was removed therefrom under reduced pressure. The resultant was washed by using an excess of chloroform and distilled water, and an organic layer was separated therefrom. The separated organic layer was dried by using MgSO$_4$ and purified by column chromatography (chloroform) to obtain Compound 2-3 (4.1 g, 7.3 mmol, yield: 73%).

Synthesis of Compound 2-7

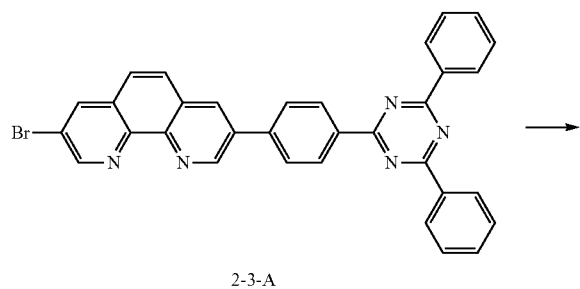

2-3-A

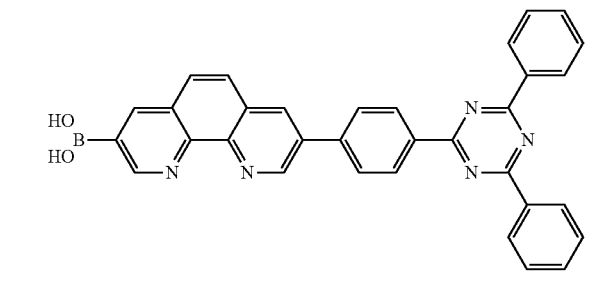

2-7-A

Intermediate 2-3-A (5.7 g, 10 mmol) was dissolved in anhydrous toluene (50 mL)/THF (10 mL) in a nitrogen atmosphere, and n-BuLi (5 mL, 1.2 equiv. 2.5 M in hexane) was slowly added thereto at a temperature of −78° C. The reaction mixture was stirred at a temperature of −78° C. for 1 hour, and trimethylborate (1.2 mmol) was added thereto. HCl (12 mL, 2M solution) was added thereto, and the solution was heated to room temperature. A separated organic layer was washed by using distilled water and brine solution. The solution was dried by using MgSO$_4$, and a solvent was removed therefrom under reduced pressure. A product obtained therefrom was washed several times by using hot n-hexane to obtain Intermediate 2-7-A (3.7 g, 6.9 mmol, yield: 69%).

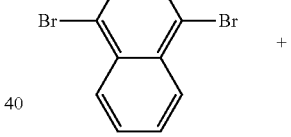

2-7-A

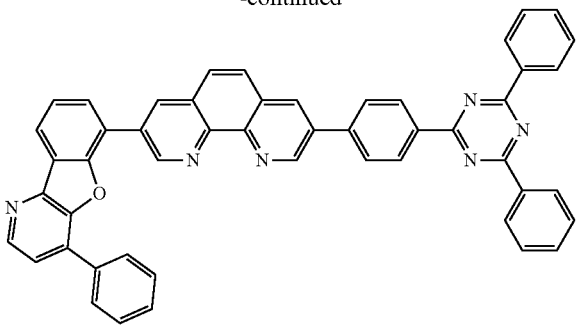

2-7

Intermediate 2-7-A (5.3 g, 10 mmol), 6-bromo-4-phenyl-benzofuro[3,2-b]pyridine (3.2 g, 10 mmol), K$_2$CO$_3$ (2.8 g, 20 mmol), and Pd(PPh$_3$)$_4$ (0.41 g, 0.35 mmol) were added to a schlenk tube, dried in a vacuum state for 2 hours, and then dissolved in 1,4-dioxane (100 mL). N$_2$-purged anhydrous MeOH (20 mL) was added thereto and stirred at a temperature of 130° C. for 48 hours in a nitrogen atmosphere. The reaction mixture was cooled to room temperature, and a solvent was removed therefrom under reduced pressure. The resultant was washed by using an excess of chloroform and distilled water, and an organic layer was separated therefrom. The separated organic layer was dried by using MgSO$_4$ and purified by column chromatography (chloroform) to obtain Compound 2-7 (2.9 g, 4.0 mmol, yield: 40%).

Synthesis of Compound 2-5

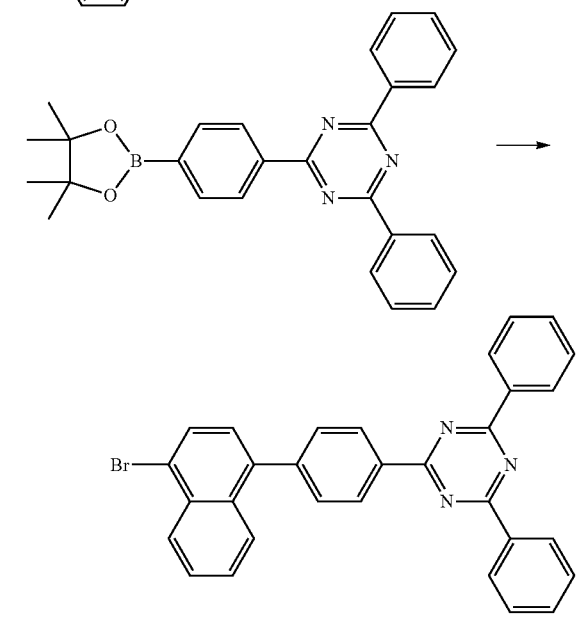

2-5-A 1,4-dibromonaphthalene (2.9 g, 10 mmol), 2,4-diphenyl-6-[4-(4,4,5,5-tetramethyl-1,3,2-dioxaborolan-2-yl)phenyl]-s-triazine (5.0 g, 11 mmol), K₂CO₃ (2.8 g, 20 mmol), and Pd(PPh₃)₄ (0.41 g, 0.35 mmol) were added to a schlenk tube, dried in a vacuum state for 2 hours, and then dissolved in DMF (100 mL). N₂-purged anhydrous EtOH (20 mL) was added thereto and stirred at a temperature of 100° C. for 24 hours in a nitrogen atmosphere. The reaction mixture was cooled to room temperature, and a solvent was removed therefrom under reduced pressure. The resultant was washed by using an excess of DCM and distilled water, and an organic layer was separated therefrom. The separated organic layer was dried by using MgSO₄ and purified by column chromatography (DCM/hexane (2:1, v/v)) to obtain Intermediate 2-5-A (3.5 g, 6.8 mmol yield: 68%).

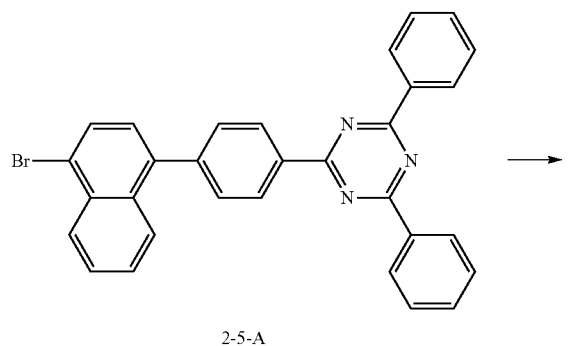

2-5-A

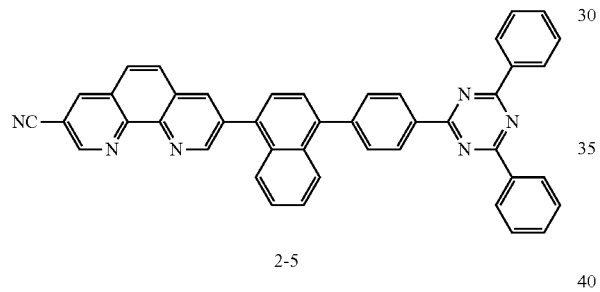

2-5

Intermediate 2-5-A (5.1 g, 10 mmol), (8-cyano-1,10-phenanthrolin-3-yl)boronic acid (2.7 g, 11 mmol), K₂CO₃ (2.8 g, 20 mmol), and Pd(PPh₃)₄ (0.41 g, 0.35 mmol) were added to a schlenk tube, dried in a vacuum state for 2 hours, and then dissolved in DMF (100 mL). N₂-purged anhydrous EtOH (20 mL) was added thereto and stirred at a temperature of 100° C. for 48 hours in a nitrogen atmosphere. The reaction mixture was cooled to room temperature, and a solvent was removed therefrom under reduced pressure. The resultant was washed by using an excess of chloroform and distilled water, and an organic layer was separated therefrom. The separated organic layer was dried by using MgSO₄ and purified by column chromatography (chloroform) to obtain Compound 2-5 (4.1 g, 6.4 mmol, yield: 64%).

Synthesis of Compound 6-1

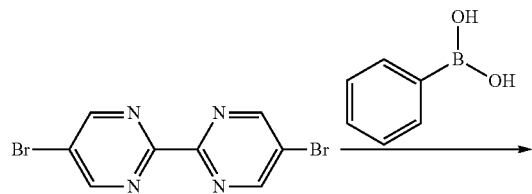

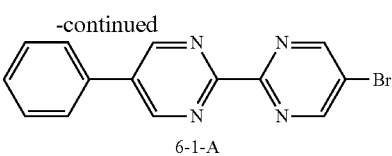

6-1-A 5,5'-dibromo-2,2'-bipyrimidine (3.2 g, 10 mmol), phenylboronic acid (1.5 g, 12 mmol), K₂CO₃ (1.4 g, 10 mmol), and Pd(PPh₃)₄ (0.41 g, 0.35 mmol) were added to a schlenk tube, dried in a vacuum state for 2 hours, and then dissolved in THF (100 mL). N₂-purged anhydrous EtOH (20 mL) was added thereto and stirred at a temperature of 80° C. for 24 hours in a nitrogen atmosphere. The reaction mixture was cooled to room temperature, and a solvent was removed therefrom under reduced pressure. The resultant was washed by using an excess of DCM and distilled water, and an organic layer was separated therefrom. The separated organic layer was dried by using MgSO₄ and purified by column chromatography (dichloromethane) to obtain Intermediate 6-1-A (2.4 g, 7.7 mmol, yield: 77%).

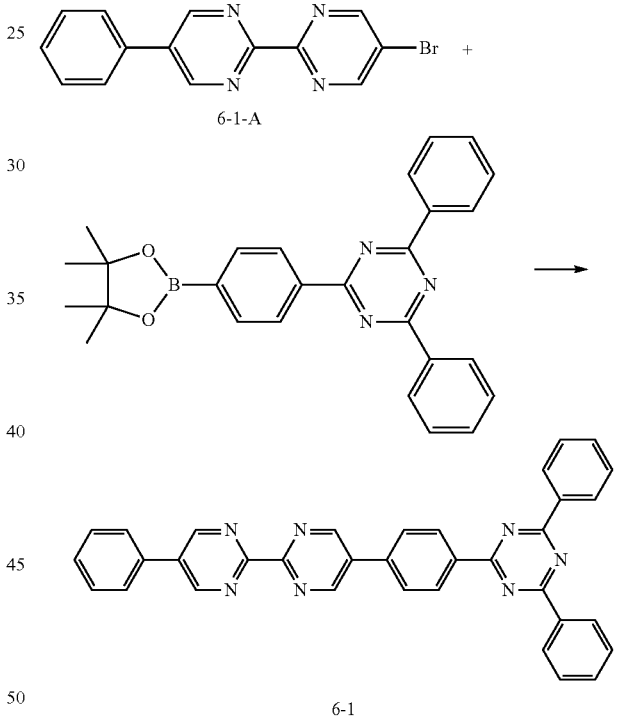

6-1

Intermediate 6-1-A (3.1 g, 10 mmol), 2,4-diphenyl-6-[4-(4,4,5,5-tetramethyl-1, 3,2-dioxaborolan-2-yl)phenyl]-s-triazine (5.0 g, 11 mmol), K₂CO₃ (2.8 g, 20 mmol), and Pd(PPh₃)₄ (0.41 g, 0.35 mmol) were added to a schlenk tube, dried in a vacuum state for 2 hours, and then dissolved in 1,4-dioxane (100 mL). N₂-purged anhydrous EtOH (20 mL) was added thereto and stirred at a temperature of 120° C. for 24 hours in a nitrogen atmosphere. The reaction mixture was cooled to room temperature, and a solvent was removed therefrom under reduced pressure. The resultant was washed by using an excess of chloroform and distilled water, and an organic layer was separated therefrom. The separated organic layer was dried by using MgSO₄ and purified by column chromatography (chloroform/hexane (5:1, v/v)) to obtain Compound 6-1 (2.9 g, 5.4 mmol, yield: 54%).

Synthesis of Compound 7-10

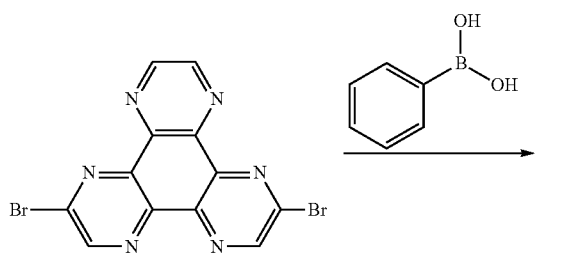

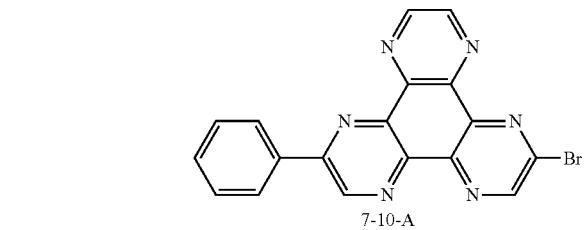

2,7-dibromodipyrazino[2,3-f:2',3'-h]quinoxaline (3.9 g, 10 mmol), phenylboronic acid (1.5 g, 12 mmol), K₂CO₃ (2.8 g, 20 mmol), and Pd(PPh₃)₄ (0.41 g, 0.35 mmol) were added to a schlenk tube, dried in a vacuum state for 2 hours, and then dissolved in DMF (100 mL). N₂-purged anhydrous EtOH (20 mL) was added thereto and stirred at a temperature of 100° C. for 24 hours in a nitrogen atmosphere. The reaction mixture was cooled to room temperature, and a solvent was removed therefrom under reduced pressure. The resultant was washed by using an excess of DCM and distilled water, and an organic layer was separated therefrom. The separated organic layer was dried by using MgSO₄ and purified by column chromatography (DCM) to obtain Intermediate 7-10-A (1.8 g, 4.6 mmol, yield: 46%).

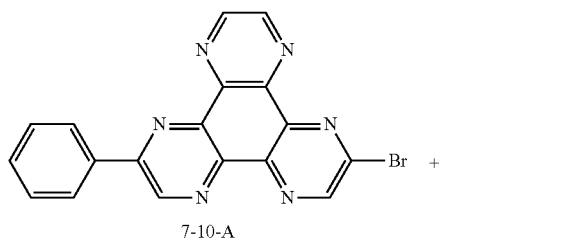

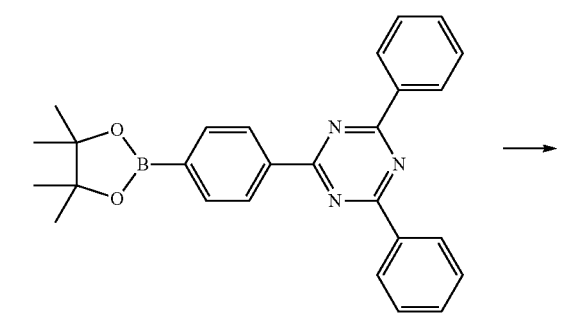

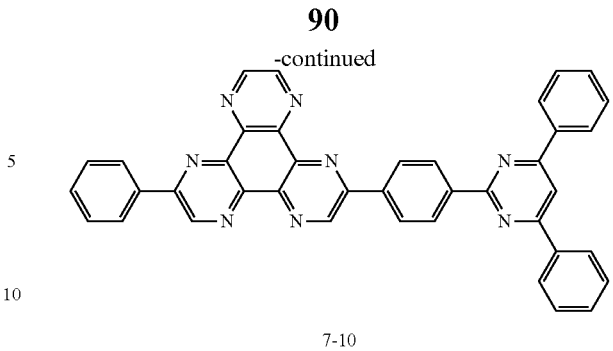

Intermediate 7-10-A (3.9 g, 10 mmol), 2,4-diphenyl-6-[4-(4,4,5,5-tetramethyl-1,3,2-dioxaborolan-2-yl)phenyl]-s-triazine (5.0 g, 11 mmol), K₂CO₃ (2.8 g, 20 mmol), and Pd(PPh₃)₄ (0.41 g, 0.35 mmol) were added to a schlenk tube, dried in a vacuum state for 2 hours, and then dissolved in 1,4-dioxane (100 mL). N₂-purged anhydrous EtOH (20 mL) was added thereto and stirred at a temperature of 120° C. for 48 hours in a nitrogen atmosphere. The reaction mixture was cooled to room temperature, and a solvent was removed therefrom under reduced pressure. The resultant was washed by using an excess of DCM and distilled water, and an organic layer was separated therefrom. The separated organic layer was dried by using MgSO₄ and purified by column chromatography (DCM) to obtain Compound 7-10 (3.5 g, 5.7 mmol, yield: 57%).

¹H NMR of each of Compounds synthesized according to Synthesis Examples is shown in Table 1.

Synthesis methods of compounds other than Compounds shown in Table 1 may also be easily recognized by those of ordinary skill in the art upon referring to the synthesis mechanisms and source materials described herein above.

TABLE 1

| Compound | $^1$H NMR (DMSO-d$_6$, 500 MHz) |
|---|---|
| 1-4 | 7.15(d, 2H), 7.25(d, 2H), 7.41-7.50(m,9H), 7.79-7.82(dd, 4H), 7.96(d, 2H), 8.12(d, 2H), 8.36(d, 4H), 8.87 (d, 2H) |
| 2-3 | 7.25(d, 2H), 7.46-7.50(m,11H), 7.91-7.96(m, 3H), 8.12(d, 1H), 8.20(s, 2H), 8.40(d, 4H) |
| 2-5 | 7.24(d, 2H), 7.46-7.52(m,8H), 7.84-7.96(m, 4H), 8.06-8.12(dd, 2H), 8.20(s, 1H), 8.26 (s, 1H), 8.36 (d, 4H), 8.81(s, 1H), 8.95-9.02(dd, 2H), 9.40 (s, 1H) |
| 2-7 | 7.25(d, 2H), 7.41-7.51(m, 12H), 7.80 (d, 1H), 7.91-8.02(m, 5H), 8.12(d, 1H)), 8.19(s, 1H), 8.26 (s, 1H), 8.36 (d, 4H), 8.61(s, 1H) |
| 6-1 | 7.20(d, 2H), 7.46-7.51(m, 11H), 7.96 (d, 2H), 8.32 (d, 4H), 9.61(s, 4H) |
| 7-10 | 7.49-7.59(m, 9H), 7.94-8.00 (dd, 6H), 8.23 (s, 1H), 8.26 (d, 2H), 8.75 (s, 4H), 8.86 (d, 2H) |

Simulation Evaluation

HOMO, LUMO, triplet energy level, singlet energy level, diploe, and oscillator strength (OSC) of Compounds 1-1 to 8-1 according to one or more embodiments, TPBi, and Compounds 101, 102, 103, and 104 were obtained a simulation (name: Gaussian, version: B3LYP/6-31 G*; e.g., the simulation included density functional theory calculations performed utilizing a B3LYP hybrid functional and a 6-31 G* basis set conducted utilizing the Gaussian software package) and compared, and results thereof are shown in Table 2.

TABLE 2

| Compound | HOMO (eV) | LUMO (eV) | Eg (eV) | Triplet (eV) | Singlet (eV) | dipole | OSC |
|---|---|---|---|---|---|---|---|
| 1-1 | −5.76 | −2.13 | 3.63 | 2.45 | 2.85 | 2.34 | f = 0.0002 |
| 1-2 | −5.76 | −2.03 | 3.73 | 2.46 | 2.99 | 2.26 | f = 0.0175 |
| 1-3 | −5.87 | −2.15 | 3.72 | 2.46 | 2.99 | 4.11 | f = 0.0090 |
| 1-4 | −5.77 | −2.02 | 3.75 | 2.46 | 2.99 | 2.19 | f = 0.0228 |
| 2-1 | −5.81 | −2.06 | 3.74 | 2.47 | 3.15 | 4.69 | f = 0.3850 |
| 2-2 | −5.71 | −1.94 | 3.77 | 2.49 | 3.16 | 3.03 | f = 0.4203 |
| 2-3 | −6.02 | −2.09 | 3.93 | 2.60 | 3.23 | 3.08 | f = 1.1958 |
| 2-4 | −6.14 | −2.21 | 3.92 | 2.62 | 3.22 | 4.67 | f = 0.8183 |
| 2-5 | −6.15 | −2.48 | 3.67 | 2.51 | 3.23 | 7.02 | f = 0.5377 |
| 2-6 | −6.06 | −2.24 | 3.81 | 2.60 | 3.10 | 3.46 | f = 0.7561 |
| 2-7 | −5.98 | −2.12 | 3.87 | 2.60 | 3.11 | 3.01 | f = 0.9681 |
| 3-1 | −5.89 | −2.08 | 3.82 | 2.62 | 3.24 | 3.27 | f = 1.0522 |
| 3-2 | −6.00 | −2.19 | 3.80 | 2.64 | 3.23 | 4.88 | f = 0.8623 |
| 4-1 | −6.16 | −2.51 | 3.65 | 2.40 | 2.91 | 0.60 | f = 1.3958 |
| 4-2 | −6.34 | −2.61 | 3.73 | 2.48 | 2.91 | 2.58 | f = 1.0225 |
| 5-1 | −5.98 | −2.07 | 3.91 | 2.67 | 3.53 | 2.93 | f = 1.5003 |
| 5-2 | −6.12 | −2.19 | 3.94 | 2.74 | 3.24 | 4.65 | f = 0.7465 |
| 6-1 | −6.18 | −2.27 | 3.91 | 2.65 | 3.13 | 0.04 | f = 0.0872 |
| 6-2 | −6.30 | −2.40 | 3.90 | 2.69 | 3.10 | 2.03 | f = 0.0646 |
| 7-1 | −5.68 | −1.80 | 3.88 | 2.44 | 3.03 | 0.74 | f = 0.0003 |
| 7-2 | −5.71 | −1.67 | 4.04 | 2.50 | 3.29 | 3.20 | f = 0.6133 |
| 7-3 | −5.91 | −1.80 | 4.11 | 2.69 | 3.27 | 3.93 | f = 0.9819 |
| 7-4 | −6.02 | −2.40 | 3.62 | 2.49 | 2.97 | 1.97 | f = 0.0113 |
| 7-5 | −5.97 | −1.79 | 4.18 | 2.76 | 3.28 | 3.62 | f = 1.3198 |
| 7-6 | −6.04 | −2.11 | 3.93 | 2.75 | 3.19 | 1.86 | f = 0.0020 |
| 7-7 | −5.66 | −1.86 | 3.80 | 2.41 | 3.01 | 1.74 | f = 0.0310 |
| 7-8 | −5.67 | −1.79 | 3.87 | 2.44 | 3.28 | 4.56 | f = 0.7059 |
| 7-9 | −6.00 | −1.93 | 4.07 | 2.63 | 3.24 | 1.85 | f = 1.0795 |
| 7-10 | −6.14 | −2.42 | 3.72 | 2.48 | 2.92 | 1.48 | f = 1.1623 |
| 7-11 | −5.97 | −1.93 | 4.04 | 2.72 | 3.33 | 1.73 | f = 1.3297 |
| 7-12 | −6.15 | −2.19 | 3.96 | 2.67 | 3.13 | 1.90 | f = 0.0849 |
| 8-1 | −6.08 | −2.30 | 3.78 | 2.63 | 3.40 | 4.15 | f = 1.4309 |
| TPBi | −5.89 | −1.51 | 4.38 | 2.79 | 3.74 | 1.04 | f = 0.0031 |
| 100 | −5.90 | −2.27 | 3.62 | 2.17 | 3.19 | 0.72 | f = 0.0379 |
| 101 | −6.33 | −2.30 | 4.03 | 2.72 | 3.64 | 0.06 | f = 0.0139 |
| 102 | −6.25 | −2.30 | 3.95 | 2.72 | 3.42 | 1.26 | f = 0.0002 |
| 103 | −5.79 | −2.23 | 3.57 | 2.28 | 3.12 | 1.19 | f = 0.0494 |

(in Table 2, "Eg" indicates a gap between HOMO and LUMO.)

From Table 2, it can be seen that Compounds 1-1 to 8-1 according to one or more embodiments have stronger oscillator strength than TPBi and Compounds 100, 101, 102, and 103. For the dipole value, it can be seen that Compounds 1-1 to 8-1 according to one or more embodiments are more polar than TPBi and Compounds 100, 101, 102, and 103. Therefore, the dipole moments of Compounds 1-1 to 8-1 according to one or more embodiments are expected to be located in the plane forming the molecules. This may be expected to have a more constant (e.g., more uniform) orientation than TPBi and Compounds 100, 102, and 103 in the molecular arrangement during deposition.

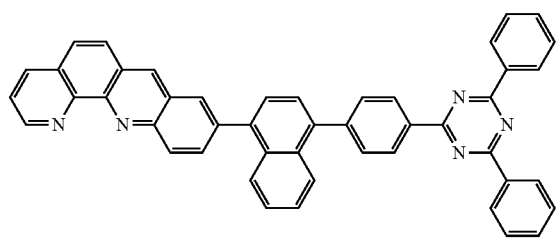

100

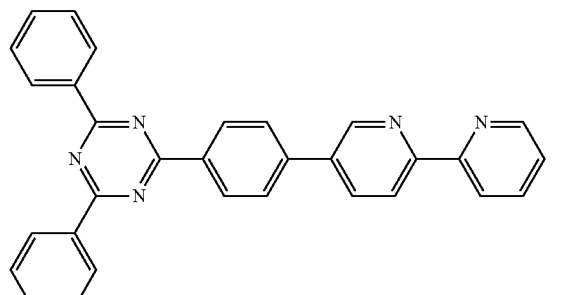

101

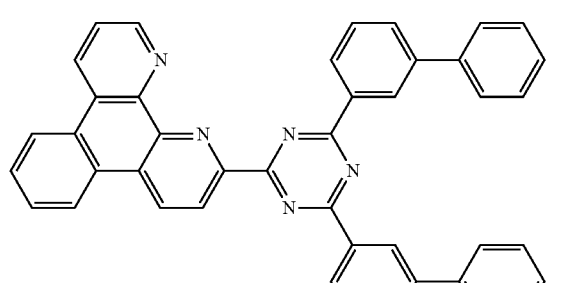

102

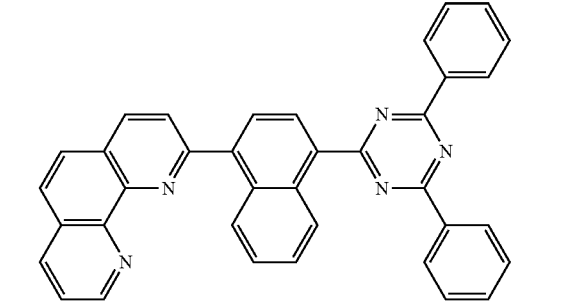

103

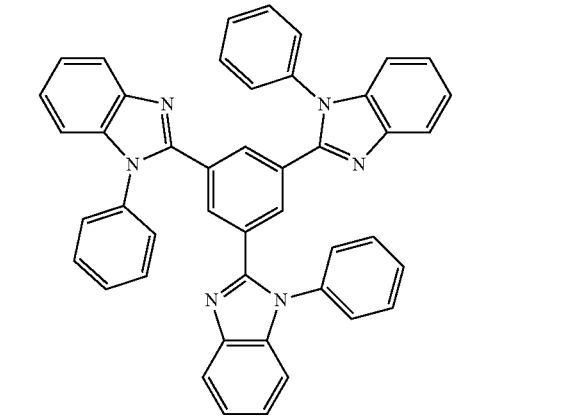

[TPBi]

Manufacture of Organic Light-Emitting Device

Comparative Example 1

As an anode, a Corning 15 Ω/cm² (1,200 Å) ITO glass substrate was cut to a size of 50 mm×50 mm×0.5 mm, sonicated with isopropyl alcohol and pure water each for 5 minutes, and then cleaned by exposure to ultraviolet rays and ozone for 30 minutes. Then, the ITO glass substrate was provided to a vacuum deposition apparatus.

An existing material (HAT-CN) was vacuum-deposited on the ITO glass substrate to form a hole injection layer having a thickness of 100 Å, and a hole transport compound TAPC was vacuum-deposited on the hole injection layer to form a hole transport layer having a thickness of 300 Å.

mCP and TPBe were co-deposited on the hole transport layer at a weight ratio of 94:6 wt % to form an emission layer having a thickness of 300 Å.

T2T was deposited on the emission layer to form a hole blocking layer having a thickness of 100 Å, TPBi was deposited on the hole blocking layer to form an electron transport layer having a thickness of 550 Å.

LiF was deposited on the electron transport layer to form an electron injection layer having a thickness of 8 Å, and Al was deposited on the electron injection layer to form an electrode having a thickness of 1,000 Å.

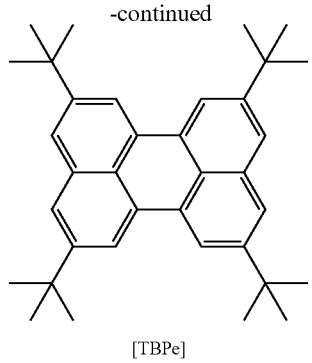

[TBPe]

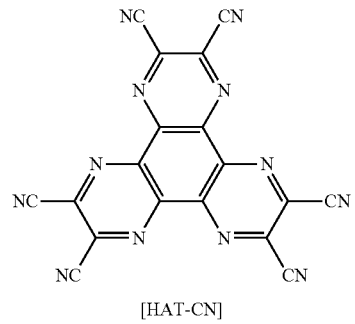

[HAT-CN]

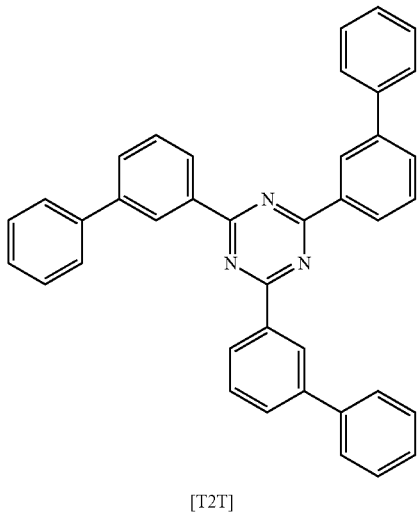

[T2T]

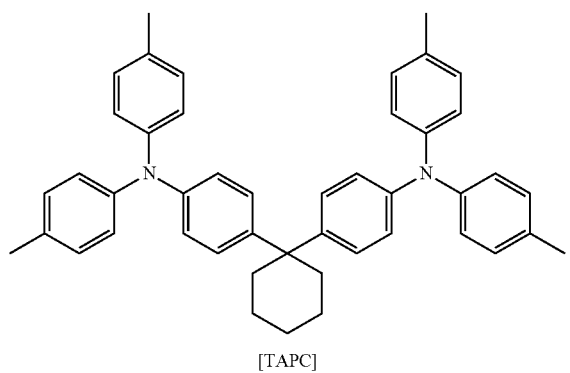

[TAPC]

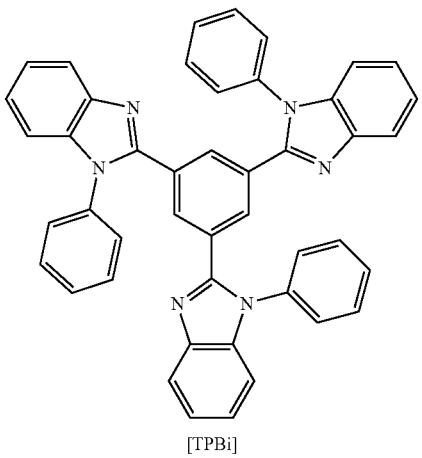

[TPBi]

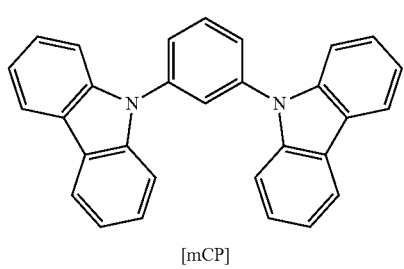

[mCP]

Comparative Example 2

An organic light-emitting device was manufactured in substantially the same manner as in Comparative Example 1, except that Compound 100 was used instead of TPBi in forming an electron transport layer.

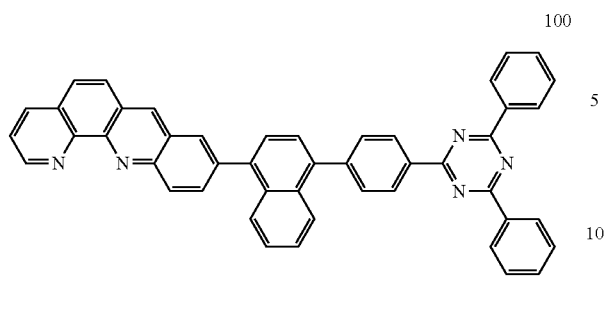

Comparative Example 3

An organic light-emitting device was manufactured in substantially the same manner as in Comparative Example 1, except that Compound 101 was used instead of TPBi in forming an electron transport layer.

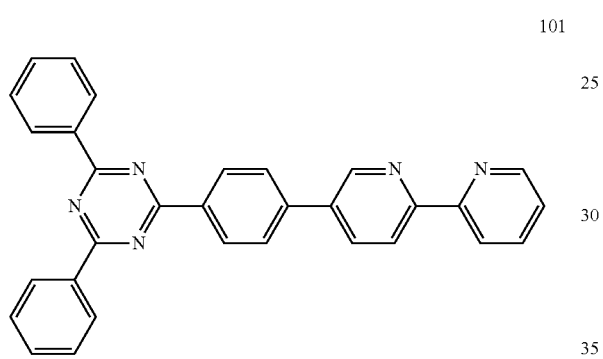

Comparative Example 4

An organic light-emitting device was manufactured in substantially the same manner as in Comparative Example 1, except that Compound 102 was used instead of TPBi in forming an electron transport layer.

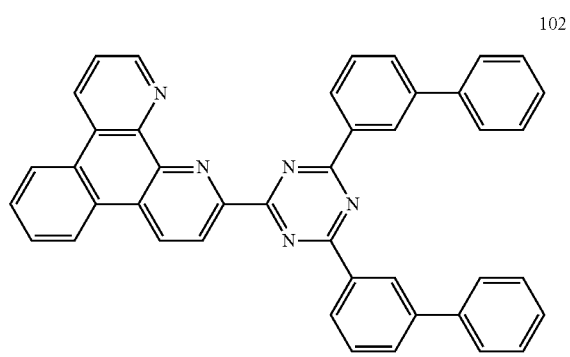 [SMILES: c1ccc(-c2cccc(-c3nc(-c4cccc(-c5ccccc5)c4)nc(-c4ccc5c6ccccc6c6cccnc6c5n4)n3)c2)cc1]

Comparative Example 5

An organic light-emitting device was manufactured in substantially the same manner as in Comparative Example 1, except that Compound 103 was used instead of TPBi in forming an electron transport layer.

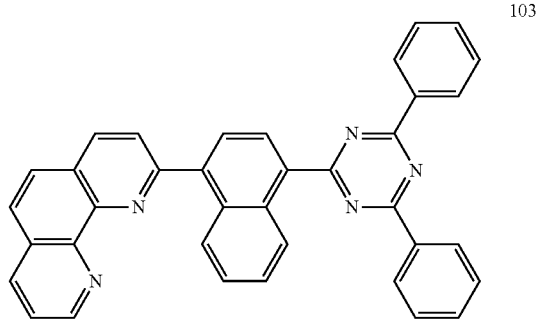 [SMILES: c1ccc(-c2nc(-c3ccccc3)nc(-c3ccc(-c4ccc5ccc6cccnc6c5n4)c4ccccc34)n2)cc1]

Example 1

An organic light-emitting device was manufactured in substantially the same manner as in Comparative Example 1, except that Compound 1-4 was used instead of TPBi in forming an electron transport layer.

Example 2

An organic light-emitting device was manufactured in substantially the same manner as in Comparative Example 1, except that Compound 2-3 was used instead of TPBi in forming an electron transport layer.

Example 3

An organic light-emitting device was manufactured in substantially the same manner as in Comparative Example 1, except that Compound 2-7 was used instead of TPBi in forming an electron transport layer.

Example 4

An organic light-emitting device was manufactured in substantially the same manner as in Comparative Example 1, except that Compound 6-1 was used instead of TPBi in forming an electron transport layer.

Example 5

An organic light-emitting device was manufactured in substantially the same manner as in Comparative Example 1, except that Compound 7-10 was used instead of TPBi in forming an electron transport layer.

Example 6

An organic light-emitting device was manufactured in substantially the same manner as in Comparative Example 1, except that Compound 2-3 was used instead of TPBi in forming an electron transport layer, and Compound 200-3 was used instead of mCP as a host.

Example 7

An organic light-emitting device was manufactured in substantially the same manner as in Comparative Example 1, except that Compound 2-5 was used instead of TPBi in forming an electron transport layer, and Compound 200-5 was used instead of mCP as a host.

The driving voltage, luminance, external quantum efficiency (EQE), and lifespan of the organic light-emitting devices manufactured according to Examples 1 to 7 and Comparative Examples 1 to 5 were manufactured, and results thereof are shown in Table 3.

TABLE 3

| | Electron transporting material | Host | Driving voltage (V) | EQE(%) | Lifespan T95 (hr) |
|---|---|---|---|---|---|
| Comparative Example 1 | TPBi | mCP | 4.8 | 3.6 | 1 |
| Comparative Example 2 | 100 | mCP | 4.2 | 5.0 | 11 |
| Comparative Example 3 | 101 | mCP | 4.3 | 3.4 | 18 |
| Comparative Example 4 | 102 | mCP | 4.8 | 3.9 | 5 |
| Comparative Example 5 | 103 | mCP | 3.7 | 6.7 | 24 |
| Example 1 | 1-4 | mCP | 3.8 | 6.1 | 25 |
| Example 2 | 2-3 | mCP | 3.3 | 9.4 | 51 |
| Example 3 | 2-7 | mCP | 3.5 | 8.3 | 43 |
| Example 4 | 6-1 | mCP | 3.9 | 5.6 | 13 |
| Example 5 | 7-10 | mCP | 3.9 | 4.3 | 10 |
| Example 6 | 2-3 | 200-3 | 3.2 | 10.2 | 87 |
| Example 7 | 2-5 | 200-5 | 3.4 | 9.9 | 71 |

From Table 3, it can be seen that the organic light-emitting devices of Examples 1 to 7 exhibit excellent results, as compared with the organic light-emitting devices of Comparative Examples 1 to 5. This is consistent with that expected in the simulation results of Table 2.

The organic light-emitting device including the compound represented by Formula 1 may exhibit excellent efficiency and improved lifespan.

It should be understood that embodiments described herein should be considered in a descriptive sense only and not for purposes of limitation. Descriptions of features or aspects within each embodiment should be considered as available for other similar features or aspects in other embodiments.

While one or more embodiments have been described with reference to the figures, it will be understood by those of ordinary skill in the art that various changes in form and details may be made therein without departing from the spirit and scope of the present disclosure as defined by the following claims, and equivalents thereof.

What is claimed is:
1. A compound represented by Formula 1:

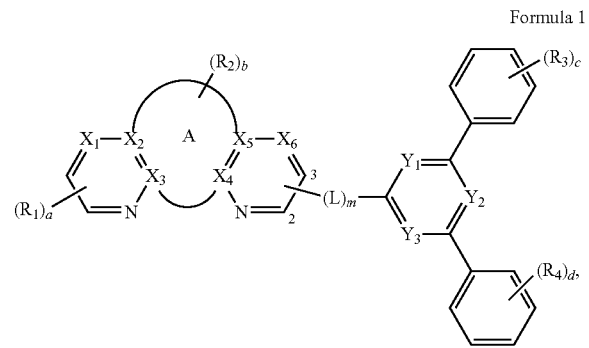

Formula 1 wherein, in Formula 1,
A is a single bond linking $X_3$ with $X_4$, or A is a fused $C_4$-$C_{60}$ carbocyclic group or a fused $C_1$-$C_{60}$ heterocyclic group,
$X_1$ is N, C, or $C(R_{11})$, $X_2$ is N, C, or $C(R_{12})$, $X_3$ is N, C, or $C(R_{13})$, $X_4$ is N, C, or $C(R_{14})$, $X_5$ is N, C, or $C(R_{15})$, and $X_6$ is N, C, or $C(R_{16})$,
$Y_1$ is N or $C(R_{21})$, $Y_2$ is N or $C(R_{22})$, $Y_3$ is N or $C(R_{23})$, and at least one of $Y_1$ to $Y_3$ is N,
$R_1$ to $R_4$, $R_{11}$ to $R_{16}$, and $R_{21}$ to $R_{23}$ are each independently selected from hydrogen, deuterium, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $-Si(Q_1)(Q_2)(Q_3)$, $-N(Q_1)(Q_2)$, $-B(Q_1)(Q_2)$, $-P(Q_1)(Q_2)$, $-C(=O)(Q_1)$, $-S(=O)_2(Q_1)$, and $-P(=O)(Q_1)(Q_2)$,
two neighboring substituents selected from $R_1$ to $R_4$, $R_{11}$ to $R_{16}$, and $R_{21}$ to $R_{23}$ are linked with each other to form a ring,
wherein when A is a single bond linking $X_3$ with $X_4$, each of $X_1$, $X_2$, $X_5$, and $X_6$ is CH, and each of $X_3$ and $X_4$ is C, $R_1$ is selected from deuterium, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $-Si(Q_1)(Q_2)(Q_3)$, $-N(Q_1)(Q_2)$, $-B(Q_1)(Q_2)$, $-P(Q_1)(Q_2)$, $-C(=O)(Q_1)$, $-S(=O)_2(Q_1)$, and $-P(=O)(Q_1)(Q_2)$, and at least one of $Y_1$ to $Y_3$ is $C(R_{21})$, $C(R_{22})$, or $C(R_{23})$, respectively,
L is selected from a substituted or unsubstituted $C_4$-$C_{60}$ carbocyclic group and a substituted or unsubstituted $C_1$-$C_{60}$ heterocyclic group,
when A is benzene, L or a moiety comprising $Y_1$ to $Y_3$ is linked with a carbon of position 3 (numerals 2 and 3 are carbon positions where L; or the moiety comprising $Y_1$ to $Y_3$ is linked to the moiety including A),
m is an integer from 0 to 3,
a is 1 or 2,
b is an integer from 1 to 4,
c and d are each independently an integer from 1 to 5,
at least one substituent of the substituted $C_1$-$C_6$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ arylene group, the substituted $C_6$-$C_{60}$ aryloxy group, the substituted $C_6$-$C_{60}$ arylthio group, the substituted $C_1$-$C_{60}$ heteroaryl group, the substituted $C_1$-$C_{60}$ heteroarylene group, the substituted monovalent non-aromatic condensed polycyclic group, the substituted monovalent non-aromatic condensed heteropolycyclic group, the substituted $C_4$-$C_{60}$ carbocyclic group, and the substituted $C_1$-$C_{60}$ heterocyclic group is selected from:

deuterium (-D), —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_1$ to $Q_3$, $Q_{11}$ to $Q_{13}$, $Q_{21}$ to $Q_{23}$, and $Q_{31}$ to $Q_{33}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_6$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_6$ heteroaryl group, a monovalent non-aromatic condensed polycyclic group, a monovalent non-aromatic condensed heteropolycyclic group, a biphenyl group, and a terphenyl group.

2. The compound of claim 1, wherein $X_1$ is C or C($R_{11}$), $X_2$ is C or C($R_{12}$), $X_3$ is C or C($R_{13}$), $X_4$ is C or C($R_{14}$), $X_5$ is C or C($R_{15}$), and $X_6$ is C or C($R_{16}$).

3. The compound of claim 1, wherein $X_2$ is C or C($R_{12}$), $X_5$ is C or C($R_{15}$), and each of $X_1$ and $X_6$ is N.

4. The compound of claim 1, wherein each of $X_2$ and $X_5$ is N, $X_1$ is C or C($R_{11}$), and $X_6$ is C or C($R_{16}$).

5. The compound of claim 1, wherein A is a single bond linking $X_3$ with $X_4$, or indicates a fused cyclopentane, a fused benzene, a fused naphthalene, or a fused quinoxaline.

6. The compound of claim 1, wherein each of $R_2$ to $R_4$ is hydrogen or deuterium.

7. The compound of claim 1, wherein L is selected from a phenylene group, a naphthylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group.

8. The compound of claim 1, wherein Formula 1 is represented by one of Formulae 1-1 to 1-7:

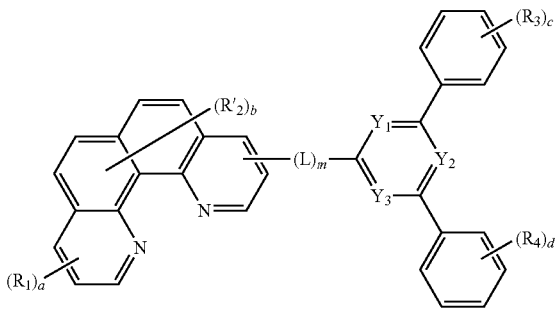

Formula 1-1

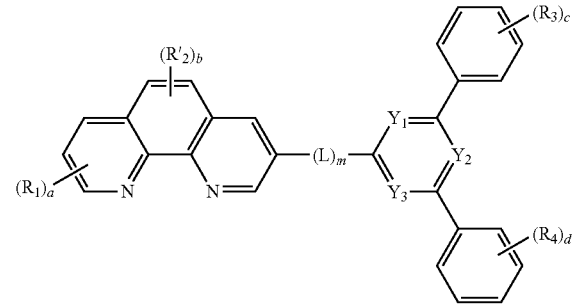

Formula 1-2

Formula 1-3

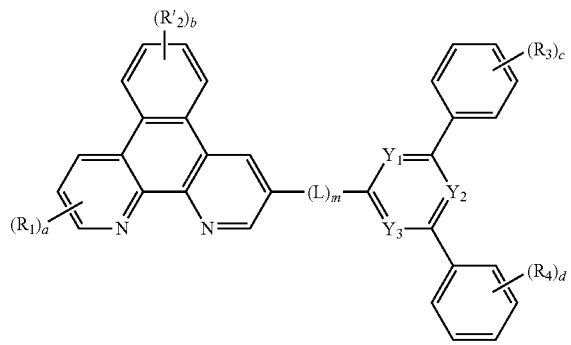

Formula 1-4

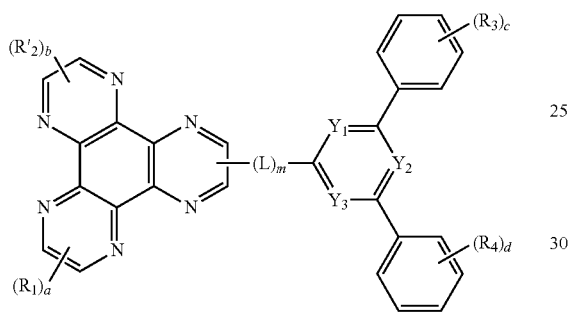

Formula 1-5

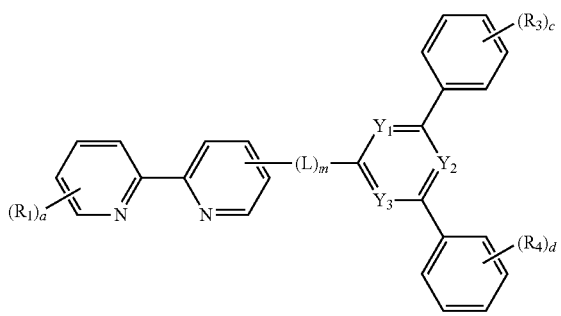

Formula 1-6

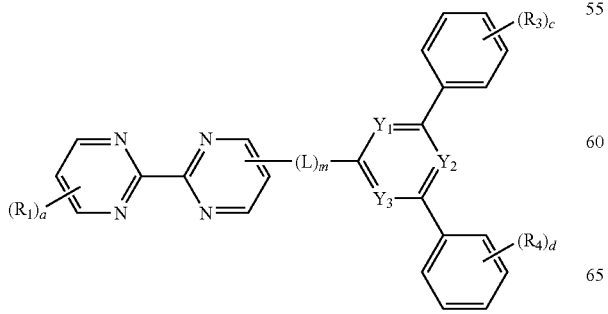

Formula 1-7

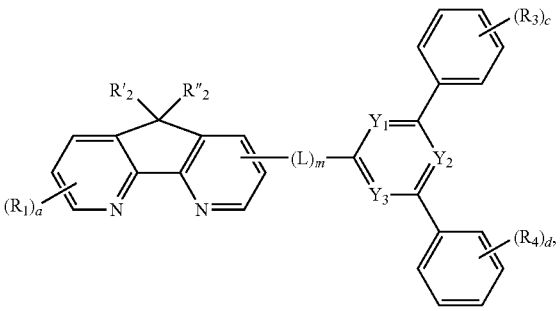

wherein, in Formulae 1-1 to 1-4 and 1-7, $R'_2$ and $R''_2$ are each independently the same as defined in connection with $R_2$ in Formula 1, and in Formula 1-5, $R_1$ is selected from deuterium, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —P($Q_1$)($Q_2$), —C(=O)($Q_1$), —S(=O)$_2$($Q_1$), and —P(=O)($Q_1$)($Q_2$).

9. The compound of claim 1, wherein $R_1$ is selected from hydrogen, deuterium, a phenyl group, a biphenyl group, a terphenyl group, a naphthyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a benzofuropyridyl group, a dibenzofuranyl group, a dibenzothiophenyl group, a triazinyl group, a benzimidazolyl group, and a phenanthrolinyl group.

10. The compound of claim 1, wherein $R_1$ is represented by hydrogen, deuterium, or a group represented by one of Formulae 2a and 2b:

2a

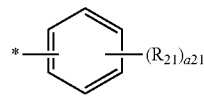

2b

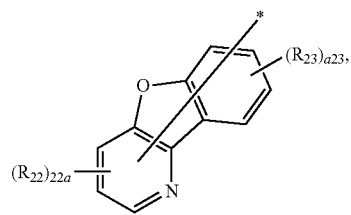

wherein, in Formulae 2a and 2b, $R_{21}$ to $R_{23}$ are each independently selected from hydrogen, deuterium, —F, —Cl, —Br, —I, a hydroxyl group, a cyano group, a nitro group, an amino group, an amidino group, a hydrazino group, a hydrazono group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a dibenzofuranyl group, a dibenzothiophenyl group, a triazinyl group, a benzimidazolyl group, and a phenanthrolinyl group, a21 is an integer from 1 to 4, a22 is 1 or 2, a23 is an integer from 1 to 3, and

* indicates a binding site to a neighboring atom.

11. The compound of claim 1, wherein the compound represented by Formula 1 is one of the following compounds:

[1-1]

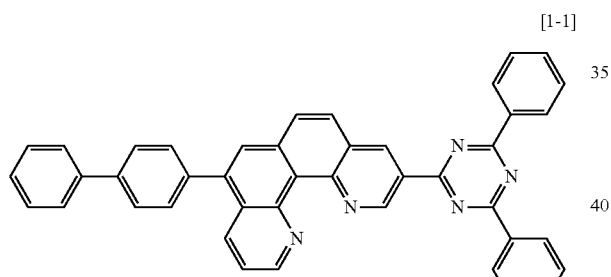

[1-2]

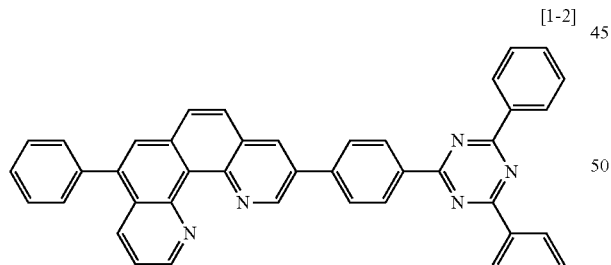

[1-3]

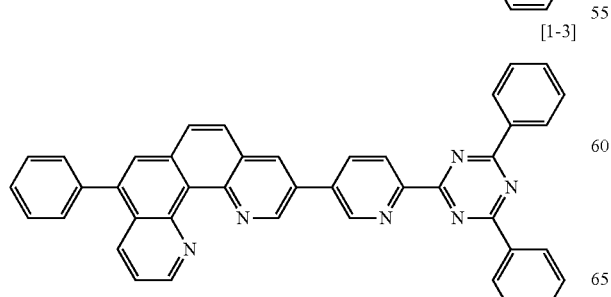

[1-4]

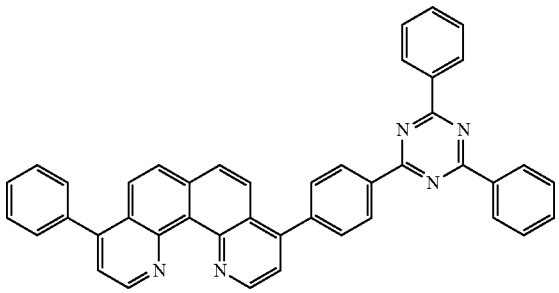

[2-1]

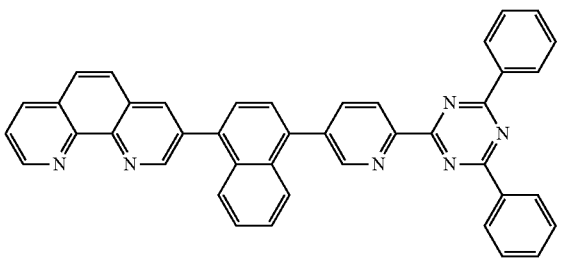

[2-2]

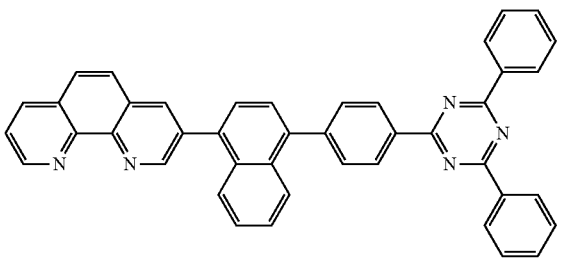

[2-3]

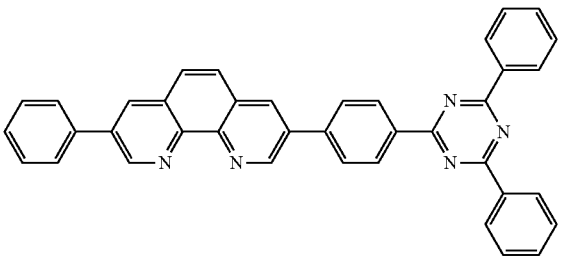

[2-4]

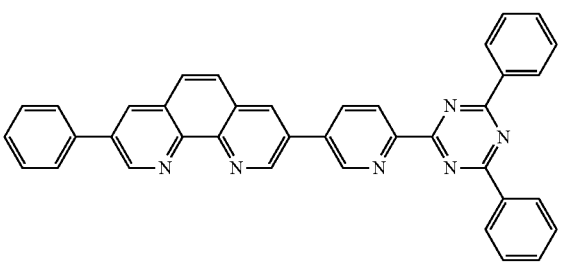

[2-5]
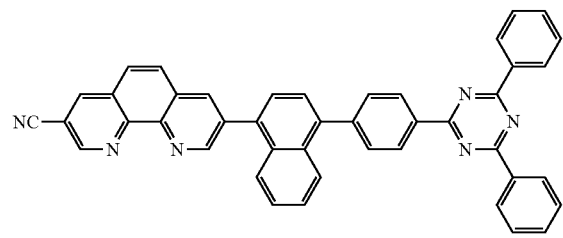
[2-6]
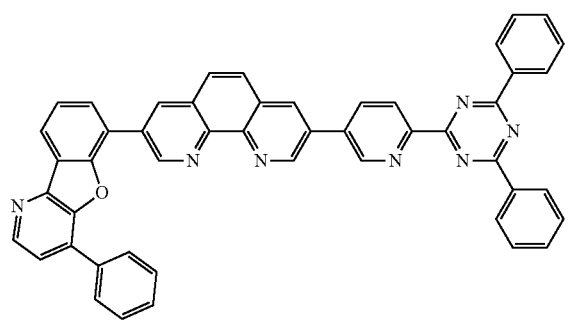
[2-7]
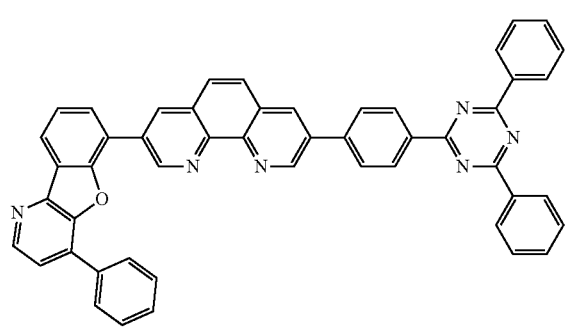
[3-1]
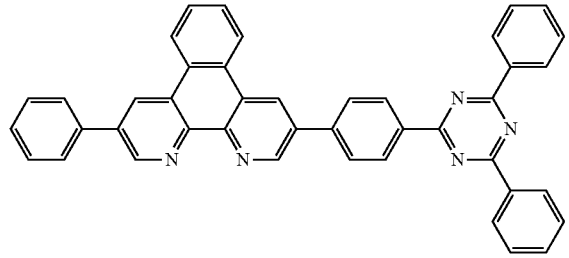
[3-2]
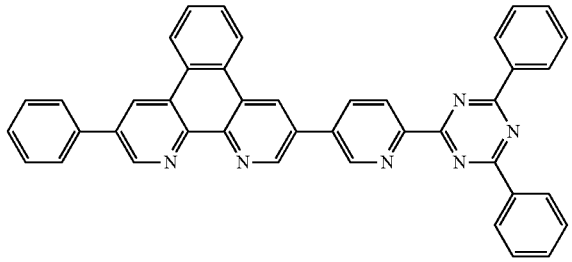
[4-1]
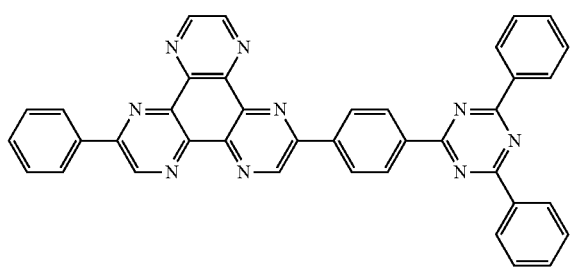
[4-2]
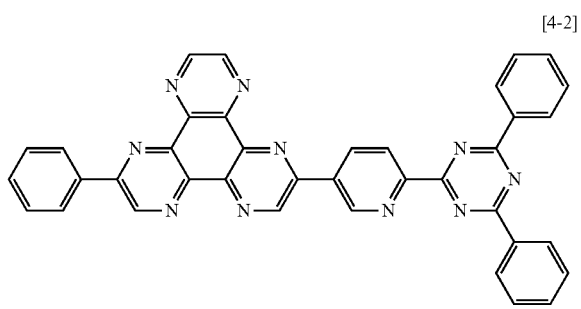
[6-1]
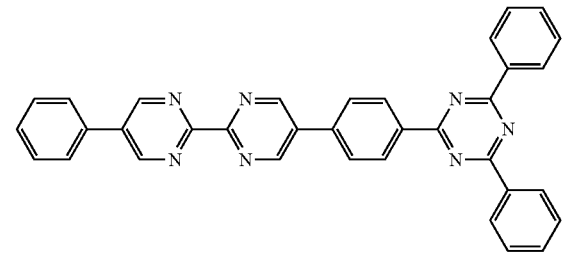
[6-2]
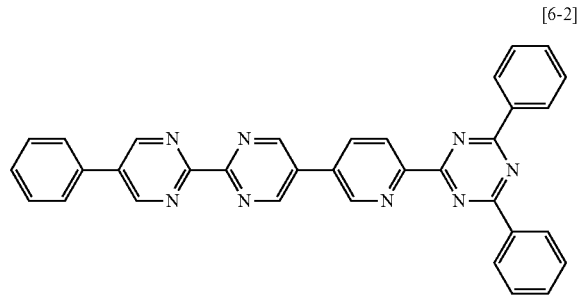
[7-1]
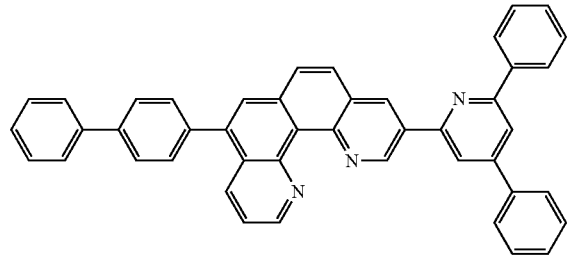

[7-2]
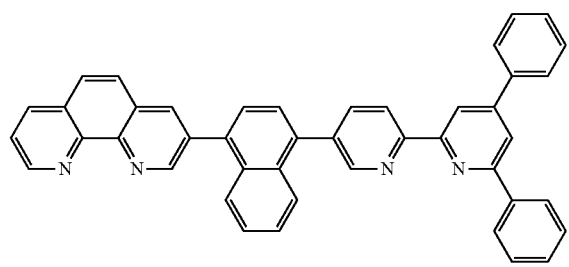
[7-3]
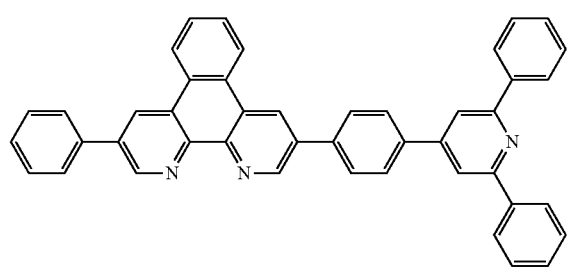
[7-4]
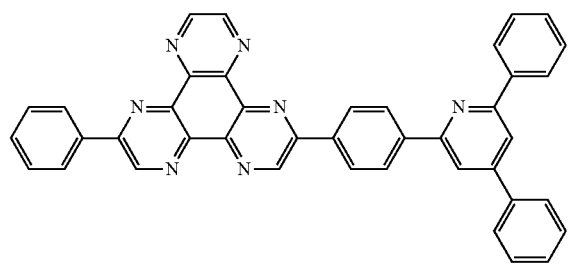
[7-5]
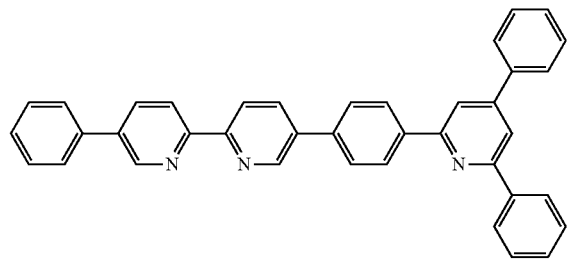
[7-6]
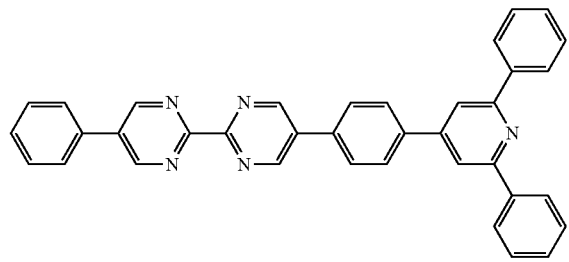
[7-7]
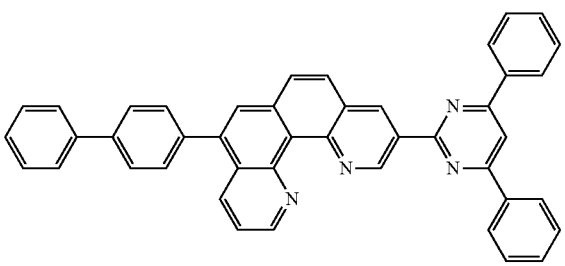
[7-8]
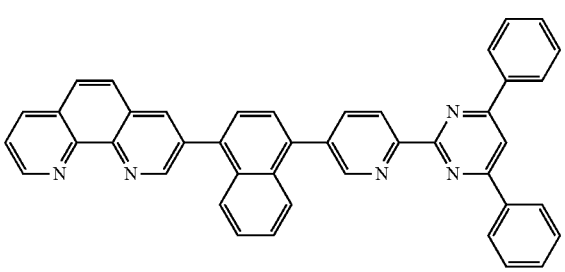
[7-9]
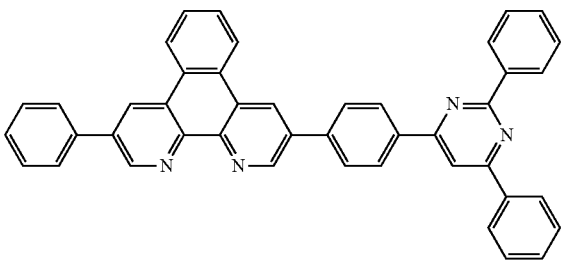
[7-10]
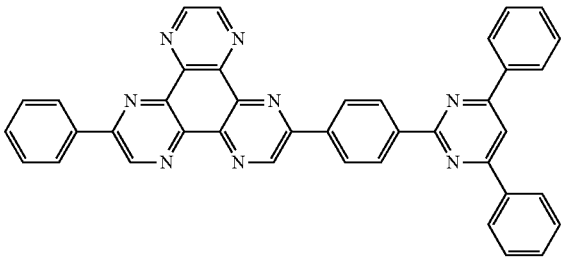
[7-11]
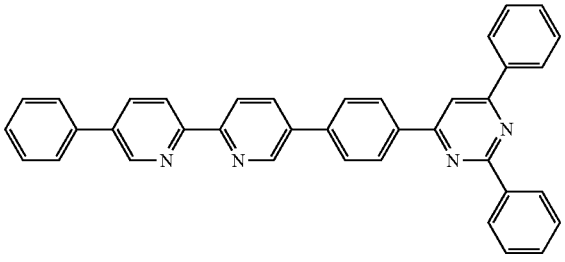

-continued

[7-12]

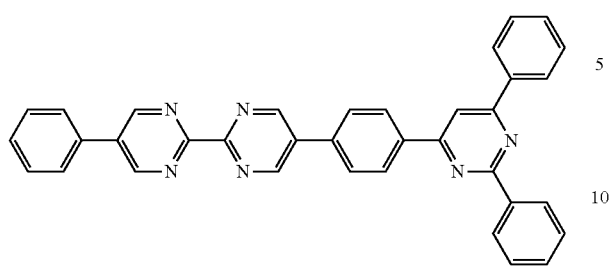

[8-1]

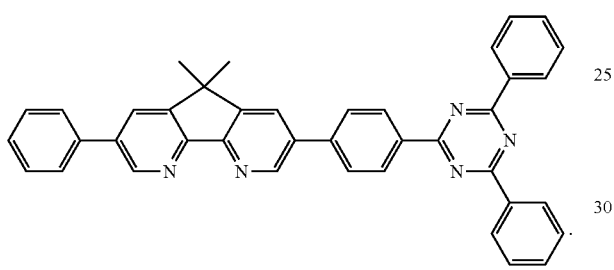

12. An organic light-emitting device comprising:
a first electrode;
a second electrode facing the first electrode; and
an organic layer between the first electrode and the second electrode and comprising an emission layer,
wherein the organic layer comprises the compound of claim 1.

13. The organic light-emitting device of claim 12, wherein the first electrode is an anode,
the second electrode is a cathode,
the organic layer between the first electrode and the second electrode and comprising the emission layer further comprises i) a hole transport region between the first electrode and the emission layer and comprising a hole injection layer, a hole transport layer, a buffer layer, an electron blocking layer, or any combination thereof and ii) an electron transport region between the emission layer and the second electrode and comprising a hole blocking layer, an electron transport layer, an electron injection layer, or any combination thereof.

14. The organic light-emitting device of claim 13, wherein the electron transport region comprises the compound represented by Formula 1.

15. The organic light-emitting device of claim 13, wherein the electron transport layer comprises the compound represented by Formula 1.

16. The organic light-emitting device of claim 13, wherein the compound chelates a metal compound migrating from the cathode.

17. The organic light-emitting device of claim 12, wherein,
the emission layer comprises a host, and the host comprises a compound represented by Formula 2:

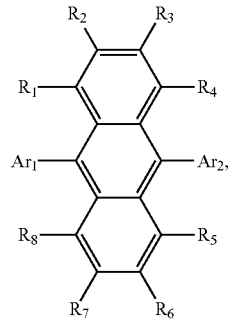

Formula 2 wherein, in Formula 2,
$Ar_1$ and $Ar_2$ are each independently selected from a substituted or unsubstituted $C_6$-$C_{60}$ aryl group and a substituted or unsubstituted $C_1$-$C_6$ heteroaryl group,
$R_1$ to $R_7$ are each independently selected from hydrogen, deuterium, a substituted or unsubstituted $C_1$-$C_{60}$ alkyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group,
at least one substituent of the substituted $C_1$-$C_6$ alkyl group, the substituted $C_6$-$C_{60}$ aryl group, the substituted $C_1$-$C_{60}$ heteroaryl group, the substituted monovalent non-aromatic condensed polycyclic group, and the substituted monovalent non-aromatic condensed heteropolycyclic group is selected from:
deuterium (-D), —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;
a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);
a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;
a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_1$ to $Q_3$, $Q_{11}$ to $Q_{13}$, $Q_{21}$ to $Q_{23}$, and $Q_{31}$ to $Q_{33}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_6$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_6$ heteroaryl group, a monovalent non-aromatic condensed polycyclic group, a monovalent non-aromatic condensed heteropolycyclic group, a biphenyl group, and a terphenyl group.

18. The organic light-emitting device of claim 17, wherein the compound represented by Formula 2 is selected from the following compounds:

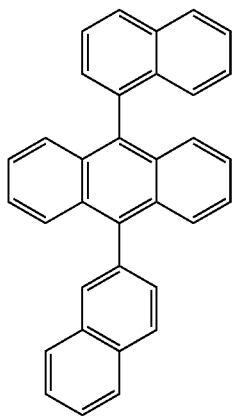

200-1

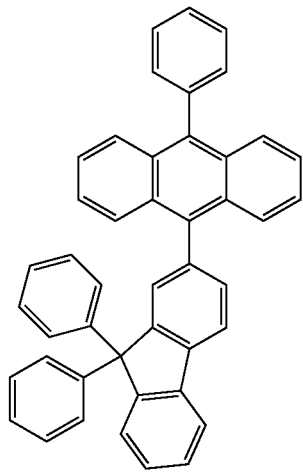

200-2

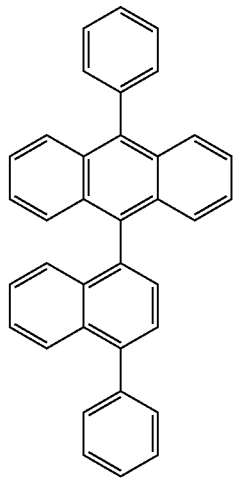

200-3

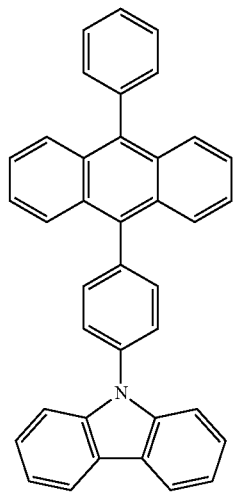

200-4

200-5
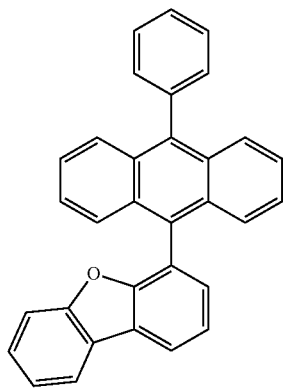
200-6
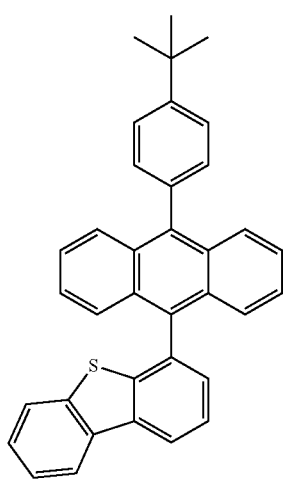
200-7
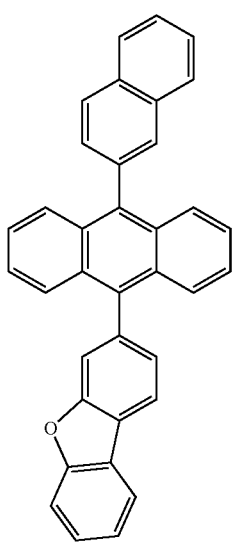
200-8
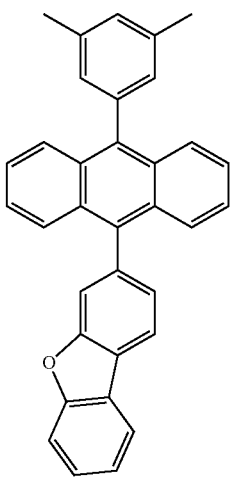
200-9
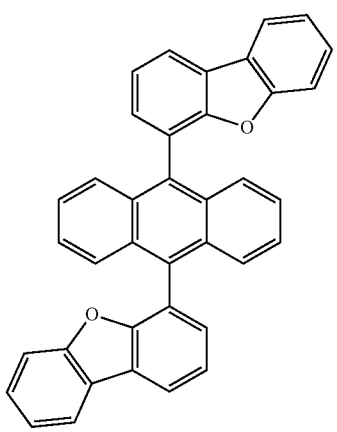
200-10
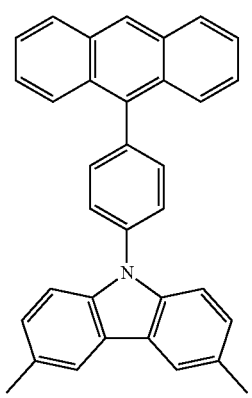

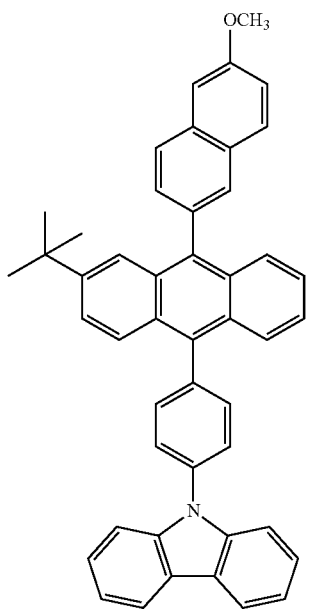

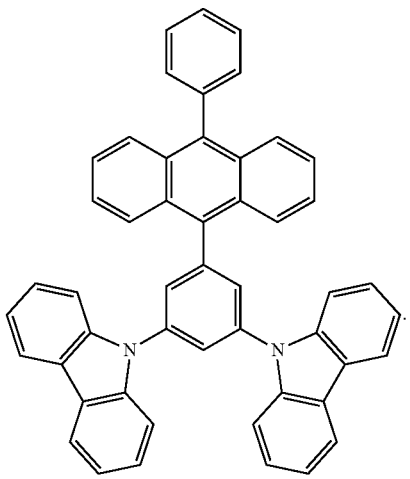

19. The organic light-emitting device of claim 12, wherein the emission layer comprises quantum dots.

20. An electronic apparatus comprising:
a thin-film transistor; and
the organic light-emitting device of claim 12,
wherein the thin-film transistor comprises a source electrode, a drain electrode, an activation layer, and a gate electrode, and
the first electrode of the organic light-emitting device is in electrical contact with one of the source electrode and the drain electrode of the thin-film transistor.

* * * * *